(12) United States Patent
Phan et al.

(10) Patent No.: US 10,822,607 B2
(45) Date of Patent: Nov. 3, 2020

(54) SITE-SPECIFIC INDUCTION OF BIMOLECULAR QUADRUPLEX-DUPLEX HYBRIDS AND METHODS OF USING THE SAME

(71) Applicant: Nanyang Technological University, Singapore (SG)

(72) Inventors: Anh Tuan Phan, Singapore (SG); Kah Wai Lim, Singapore (SG)

(73) Assignee: Nanyang Technological University, Singapore (SG)

( * ) Notice: Subject to any disclaimer, the term of this patent is extended or adjusted under 35 U.S.C. 154(b) by 55 days.

(21) Appl. No.: 14/654,361

(22) PCT Filed: Dec. 20, 2013

(86) PCT No.: PCT/SG2013/000544
§ 371 (c)(1),
(2) Date: Jun. 19, 2015

(87) PCT Pub. No.: WO2014/098773
PCT Pub. Date: Jun. 26, 2014

(65) Prior Publication Data
US 2016/0046932 A1 Feb. 18, 2016

Related U.S. Application Data

(60) Provisional application No. 61/745,009, filed on Dec. 21, 2012.

(51) Int. Cl.
| | | |
|---|---|---|
| *C12Q 1/68* | (2018.01) | |
| *C07H 21/00* | (2006.01) | |
| *C12N 15/113* | (2010.01) | |
| *C12N 15/11* | (2006.01) | |
| *C12Q 1/6876* | (2018.01) | |

(52) U.S. Cl.
CPC .......... *C12N 15/113* (2013.01); *C12N 15/111* (2013.01); *C12Q 1/6876* (2013.01); *C12N 2310/11* (2013.01); *C12N 2310/14* (2013.01); *C12N 2320/50* (2013.01); *C12N 2330/30* (2013.01)

(58) Field of Classification Search
CPC ................................. C07H 21/00; C12P 19/34
See application file for complete search history.

(56) References Cited

U.S. PATENT DOCUMENTS

| | | | | |
|---|---|---|---|---|
| 5,424,413 A * | 6/1995 | Hogan | ............... | C12N 15/1068 435/6.1 |
| 5,449,616 A * | 9/1995 | Campbell | .......... | C07K 14/4707 435/252.3 |
| 5,472,841 A * | 12/1995 | Jayasena | ............... | A61K 47/549 435/6.13 |
| 5,582,979 A * | 12/1996 | Weber | .................. | C12Q 1/6858 435/6.11 |
| 5,658,738 A * | 8/1997 | Nadeau | ............... | C12N 15/1137 435/6.1 |
| 5,948,897 A * | 9/1999 | Sen | ......................... | C12N 15/10 435/6.12 |
| 6,361,947 B1 * | 3/2002 | Dong | ................... | C12Q 1/6837 435/6.12 |
| 2001/0053519 A1 * | 12/2001 | Fodor | .................. | B01J 19/0046 435/6.11 |
| 2002/0110814 A1 * | 8/2002 | Rernacle | ............... | C12Q 1/6837 435/6.14 |
| 2003/0017137 A1 * | 1/2003 | Alfieri | ..................... | C07K 14/55 424/93.1 |
| 2003/0077596 A1 * | 4/2003 | Sundrehagen | ....... | G01N 33/542 435/6.12 |
| 2005/0287548 A1 * | 12/2005 | Bao | .......................... | B82Y 5/00 435/6.11 |
| 2010/0003682 A1 * | 1/2010 | Veiby | ................... | C12Q 1/6886 435/6.14 |
| 2012/0315642 A1 * | 12/2012 | Kankia | ................ | C12Q 1/6816 435/6.12 |

FOREIGN PATENT DOCUMENTS

WO 96/11010 A1 4/1996

OTHER PUBLICATIONS

Ge et al. Agnew.Chem. Int. Ed. 49 :9965 (2010).*
Tian et al., Chem. Euro J. 19 :92-95 (published online Dec. 7, 2012).*
Braasch et al., Chemistry & Biology 8 :1-7 (Year: 2001).*
Vester et al.,LNA (Locked Nucleic Acid): High-Affinity Targeting of ComplementaryRNA and DNA. Biochemistry 43(42) : 13324. (Year: 2004).*

(Continued)

*Primary Examiner* — Ethan C Whisenant
(74) *Attorney, Agent, or Firm* — Seed IP Law Group LLP

(57) ABSTRACT

A method for the generation of a G-quadruplex structure on a target nucleic acid sequence is presented. The approach combines the specificity of Watson-Crick base pair with the stability associated with a robust G-quadruplex scaffold. The induction of such bimolecular quadruplex-duplex hybrids can be applied within the antigene or antisense context for enhanced steric blockage to the transcriptional or translational machinery. In addition, such structures provide unique features for ligand design. This approach also allows the site-specific generation of G-quadruplex structures within nucleic acid nanoarchitectures.

20 Claims, 33 Drawing Sheets

Specification includes a Sequence Listing.

(56) References Cited

OTHER PUBLICATIONS

Ambrus et al., "Solution Structure of the Biologically Relevant G-Quadruplex Element in the Human c-MYC Promoter. Implications for G-Quadruplex Stabilization," *Biochemistry* 44:2048-2058, 2005.
Balasubramanian et al., "G-quadruplex nucleic acids as therapeutic targets," *Current Opinion in Chemical Biology* 13:345-353, 2009.
Balasubramanian et al., "Targeting G-quadruplexes in gene promoters: a novel anticancer strategy?," *Nature Reviews: Drug Discovery* 10:261-273, Apr. 2011.
Balkwill et al., "Folding Topology of a Bimolecular DNA Quadruplex Containing a Stable Mini-hairpin Motif within the Diagonal Loop," *J. Mol. Biol.* 385:1600-1615, 2009.
Blackburn, "Structure and Function of Telomeres," *Nature* 350:569-573, Apr. 1991.
Bourdoncle et al., "Quadruplex-Based Molecular Beacons as Tunable DNA Probes," *J. Am. Chem. Soc.* 128:11094-11105, 2006.
Breaker, "DNA aptamers and DNA enzymes," *Current Opinion in Chemical Biology* 1:26-31, 1997.
Bugaut et al., "A Sequence-Independent Study of the Influence of Short Loop Lengths on the Stability and Topology of Intramolecular DNA G-Quadruplexes," *Biochemistry* 47:689-697, 2008.
Burge et al., "Quadruplex DNA: sequence, topology and structure," *Nucleic Acids Research* 34(19):5402-5415, 2006.
Cahoon et al., "An Alternative DNA Structure Is Necessary for Pilin Antigenic Variation in *Neisseria gonorrhoeae,*" *Science* 325:764-768, Aug. 2009.
Cantor et al., "Oligonucleotide Interactions. III. Circular Dichroism Studies of the Conformation of Deoxyoligonucleotides," *Biopolymers* 9:1059-1077, 1970.
Cogoi et al., "G-quadruplex formation within the promoter of the KRAS proto-oncogene and its effect on transcription," *Nucleic Acids Research* 34(9): 2536-2549, 2006.
Dai et al., "NMR solution structure of the major G-quadruplex structure formed in the human BCL2 promoter region," *Nucleic Acids Research* 34(18):5133-5144, 2006.
Davis, "G-Quartets 40 Years Later: From 5'-GMP to Molecular Biology and Supramolecular Chemistry," *Angew. Chem. Int. Ed.* 43:668-698, 2004.
Do et al., "Stacking of G-quadruplexes: NMR structure of a G-rich oligonucleotide with potential anti-HIV and anticancer activity," *Nucleic Acids Research* 39(21):9448-9457, Aug. 2011.
Dutta et al., "Development of new functional nanostructures consisting of both DNA duplex and quadruplex," *Chem. Commun.* 46:7772-7774, 2010.
Eddy et al., "Gene function correlates with potential for G4 DNA formation in the human genome," *Nucleic Acids Research* 34(14):3887-3896, 2006.
Egholm et al., "PNA hybridizes to complementary oligonucleotides obeying the Watson-Crick hydrogen-bonding rules," *Nature* 365:566-568, Oct. 1993.
Felsenfeld et al., "Formation of a Three-Stranded Polynucleotide Molecule," *J. Am. Chem. Soc.* 79(8):2023-2024, Apr. 1957.
Fernando et al., "A Conserved Quadruplex Motif Located in a Transcription Activation Site of the Human c-kit Oncogene," *Biochemistry* 45:7854-7860, 2006.
Franklin et al., "Molecular Configuration in Sodium Thiocyanate," *Nature* 171:740-741, Apr. 1953.
Ge et al., "A Robust Electronic Switch Made of Immobilized Duplex/Quadruplex DNA," *Angew. Chem. Int. Ed.* 49:9965-9967, 2010.
Gellert et al., "Helix Formation by Guanylic Acid," *PNAS* 48:2013-2018, 1962.
Guédin et al., "Sequence effects in single-base loops for quadruplexes," *Biochimie* 90:686-696.
Guédin et al., "Stability of intramolecular quadruplexes: sequence effects in the central loop," *Nucleic Acids Research* 37(16):5559-5567, 2009.
Guédin et al., "How long is too long? Effects of loop size on G-quadruplex stability," *Nucleic Acids Research* 38(21):7858-7868, 2010.
Gunaratnam et al., "Targeting Human Gastrointestinal Stromal Tumor Cells with a Quadruplex-Binding Small Molecule," *J. Med. Chem.* 52:3774-3783, 2009.
Guo et al., "Formation of Pseudosymmetrical G-Quadruplex and i-Motif Structures in the Proximal Promoter Region of the RET Oncogene," *J. Am. Chem. Soc.* 129:10220-10228, 2007.
Ha et al., "Crystal structure of a junction between B-DNA and Z-DNA reveals two extruded bases," *Nature* 437:1183-1186, Oct. 2005.
Hagihara et al., "Antisense-Induced Guanine Quadruplexes Inhibit Reverse Transcription by HIV-1 Reverse Transcriptase," *J. Am. Chem. Soc.* 132:11171-11178, 2010.
Han et al., "A DNA polymerase stop assay for G-quadruplex-interactive compounds," *Nucleic Acids Research* 27(2):537-542, 1999.
Hazel et al., "Loop-Length-Dependent Folding of G-Quadruplexes," *J. Am. Chem. Soc.* 126:16405-16415, 2004.
Hélène et al., "Specific regulation of gene expression by antisense, sense and antigene nucleic acids," *Biochimica et Biophysica Acta* 1049:99-125, 1990.
Holliday, "A mechanism for gene conversion in fungi," *Genet. Res., Camb.* 5:282-304, 1964.
Hoogsteen, "The Crystal and Molecular Structure of a Hydrogen-Bonded Complex Between 1-Methylthymine and 9-Methyladenine," *Acta Cryst.* 16:907-916, 1963.
Hsu et al., "A G-Rich Sequence within the *c-kit* Oncogene Promoter Forms a Parallel G-Quadruplex Having Asymmetric G-Tetrad Dynamics," *J. Am. Chem. Soc.* 131:13399-13409, 2009.
Huang et al., "A Contractile Electronic Switch Made of DNA," *J. Am. Chem. Soc.* 132:2663-2671, 2010.
Huppert et al., "Prevalence of quadruplexes in the human genome," *Nucleic Acids Research* 33(9):2908-2916, 2005.
Huppert et al., "G-quadruplexes in promoters throughout the human genome," *Nucleic Acids Research* 35(2):406-413, 2007.
Jaeger et al., "The architectonics of programmable RNA and DNA nanostructures," *Current Opinion in Structural Biology* 16:531-543, 2006.
Koshkin et al., "LNA (Locked Nucleic Acids): Synthesis of the Adenine, Cytosine, Guanine, 5-Methylcytosine, Thymine, and Uracil Bicyclonnucleoside Monomers, Oligomerisation, and Unprecedented Nucleic Acid Recognition," *Tetrahedron* 54:3607-3630, 1998.
Kuryavyi et al., "Solution structures of all parallel-stranded monomeric and dimeric G-quadruplex scaffolds of the human *c-kit2* promoter," *Nucleic Acids Research* 38(19):6757-6773, 2010.
Lilley, "Structures of helical junctions in nucleic acids," *Quarterly Reviews of Biophysics* 33(2):109-159, 2000.
Lim et al., "Structure of the Human Telomere in K.$^+$Solution: A Stable Basket-Type G-Quadruplex with Only Two G-Tetrad Layers," *J. Am. Chem. Soc.* 131:4301-4309, 2009.
Lim et al., "Coexistence of Two Distinct G-Quadruplex Conformations in the hTERT Promoter," *J. Am. Chem. Soc.* 132:12331-12342, 2010.
Lim et al., "Sequence variant $(CTAGGG)_n$ in the human telomere favors a G-quadruplex structure containing a G•C•G•C tetrad," *Nucleic Acids Research* 37(18):6239-6248, 2009.
Liu et al., "Aptamer-Directed Self-Assembly of Protein Arrays on a DNA Nanostructure," *Angew. Chem.* 117:4407-4412, 2005.
Liu et al., "Functional Nucleic Acid Sensors," *Chem. Rev.* 109:1948-1998, 2009.
Lopes et al., "G-quadruplex-induced instability during leading-strand replication," *The EMBO Journal* 30:4033-4046, 2011.
Micheli et al., "Self-organization of G-quadruplex structures in the hTERT core promoter stabilized by polyaminic side chain perylene derivatives," *Biophysical Chemistry* 153:43-53, 2010.
Mitani et al., "A GGCAGG Motif in Minisatellites Affecting Their Germline Instability," *The Journal of Biological Chemistry* 265(25):15203-15210, 1990.
Moser et al., "Sequence-Specific Cleavage of Double Helical DNA by Triple Helix Formation," *Science* 238(4827):645-650, Oct. 1987.

(56) References Cited

OTHER PUBLICATIONS

Nielsen et al., "Sequence-Selective Recognition of DNA by Strand Displacement with a Thymine-Substituted Polyamide," *Science* 254(5037):1497-1500, Dec. 1991.
Obika et al., "Synthesis of 2'O,4'-C-Methylneuridine and -cytidine, Novel Bicyclic Nucleosides Having a Fixed $C_3$,—endo Sugar Puckering," *Tetrahedron Letters* 38(50):8735-8738, 1997.
Paeschke et al., "DNA Replication through G-Quadruplex Motifs Is Promoted by the *Saccharomyces cerevisiae* Pif1 DNA Helicase," *Cell* 145:678-691, May 2011.
Palumbo et al., "Formation of a Unique End-to-End Stacked Pair of G-Quadruplexes in the hTERT Core Promoter with Implications for Inhibition of Telomerase by G-Quadruplex-Interactive Ligands," *J. Am. Chem. Soc.* 131:10878-10891, 2009.
Patel et al., "Human telomere, oncogenic promoter and 5'-UTR G-quadruplexes: diverse higher order DNA and RNA targets for cancer therapeutics," *Nucleic Acids Research* 35(22):7429-7455, 2007.
Phan et al., "Propeller-Type Parallel-Stranded G-Quadraplexes in the Human *c-myc* Promoter," *J. Am. Chem. Soc.* 126:8710-8716, 2004.
Phan et al., "Structure of an Unprecedented G-Quadruplex Scaffold in the Human *c-kit* Promoter," *J. Am. Chem. Soc.* 129:4386-4392, 2007.
Phan et al., "Small-molecule interaction with a five-guanine-tract G-quadruplex structure from the human *MYC* promoter," *Nature Chemical Biology* 1(3):167-173, 2005.
Phan et al., "Structure-function studies of FMRP RGG peptide recognition of an RNA duplex-quadruplex junction," *Nature Structural & Molecular Biology* 18(7):796-804, 2011.
Phan et al., "An interlocked dimeric parallel-stranded DNA quadruplex: A potent inhibitor of HIV-1 integrase," *PNAS* 102(3):634-639, Jan. 2005.
Rachwal et al. "Sequence effects of single base loops in intramolecular quadruplex DNA," *FEBS Letters* 581:1657-1660, 2007.
Rachwal et al., "Intramolecular DNA quadruplexes with different arrangements of short and long loops," *Nucleic Acids Research* 35(12):4214-4222, 2007.
Rankin et al., "Putative DNA Quadruplex Formation within the Human *c-kit* Oncogene," *J. Am. Chem. Soc.* 127:10584-10589, 2005.
Risitano et al., "Influence of loop size on the stability of intramolecular DNA quadruplexes," *Nucleic Acids Research* 32(8):2598-2606, 2004.
Schultze et al., "Three-dimensional Solution Structure of the Thrombin-binding DNA Aptamer d(GGTTGGTGTGGTTGG)," *J. Mol. Biol.* 235:1532-1547, 1994.
Seeman, "Nanomaterials Based on DNA," *Annu. Rev. Biochem.* 79:65-87, 2010.
Sen et al., "Formation of parallel four-stranded complexes by guanine-rich motifs in DNA and its implications for meiosis," *Nature* 334:364-366, 1988.
Shimizu et al., "Immunoglobulin Class Switching," *Cell* 36:801-803, 1984.
Siddiqui-Jain et al., "Direct evidence for a G-quadruplex in a promoter region and its targeting with a small molecule to repress *c-MYC* transcription," *PNAS* 99(18):11593-11598, 2002.
Simonsson, "G-Quadruplex DNA Structures—Variations on a Theme," *Biol. Chem.* 382:621-628, Apr. 2001.
Simonsson et al., "DNA tetraplex formation in the control region of *c-myc*," *Nucleic Acids Research* 26(5):1167-1172, 1998.
Summers et al., "Nuclear magnetic resonance and circular dichroism studies of a duplex—single-stranded hairpin loop equilibrium for the oligodeoxyribonucleotide sequence d(CGCGATTCGCG)," *Nucleic Acids Research* 13(17):6375-6386, 1985.
Sun et al., "Sequence-specific intercalating agents: Intercalation at specific sequences on duplex DNA via major groove recognition by oligonucleotide-intercalator conjugates," *Proc. Natl. Acad. Sci. USA* 86:9198-9202, Dec. 1989.
Sundquist et al., "Telomeric DNA dimerizes by formation of guanine tetrads between hairpin loops," *Nature* 342:825-829, Dec. 1989.
Todd et al., "Highly prevalent putative quadruplex sequence motifs in human DNA," *Nucleic Acids Research* 33(9):2901-2907, 2005.
Tong et al., "Solution structure of all parallel G-quadruplex formed by the oncogene RET promoter sequence," *Nucleic Acids Research* 39(15):6753-6763, 2011.
Uhlmann et al., "Antisense Oligonucleotides: A New Therapeutic Principle," *Chemical Reviews* 90(4):544-584, Jun. 1990.
Venczel et al., "Synapsable DNA," *J. Mol. Biol.* 257:219-224, 1996.
Watson et al., "Molecular Structure of Nucleic Acids," *Nature* 171(4356):737-738, Apr. 1953.
Wei et al., "Crystal structure of a *c-kit* promoter quadruplex reveals the structural role of metal ions and water molecules in maintaining loop conformation," *Nucleic Acids Research* 40(10):4691-4700, 2012.
Weitzmann et al., "The Development and Use of a DNA Polymerase Arrest Assay for the Evaluation of Parameters Affecting Intrastrand Tetraplex Formation," *The Journal of Biological Chemistry* 271(34):20958-20964, Aug. 1996.
Westhof, "Westhof's Rule," *Nature* 358:459-460, Aug. 1992.
Wilkins et al., "Molecular Structure of Deoxypentose Nucleic Acids," *Nature* 171(4356):738-740, Apr. 1953.
Williamson et al., "Monovalent Cation-Induced Structure of Telomeric DNA: The G-Quartet Model," *Cell* 59:871-880, Dec. 1989.
Yurke et al., "A DNA-fuelled molecular machine made of DNA," *Nature* 406:605-608, Aug. 2010.
Zhu et al., "Structure of a single-cytidine hairpin loop formed by the DNA triplet GCA," *Nature Structural Biology* 2(11):1012-1017, Nov. 1995.
Sun et al., "The proximal promoter region of the human vascular endothelial growth factor gene has a G-quadruplex structure that can be targeted by G-quadruplex-interactive agents," *Mol Cancer Ther.* 7(4):880-889 (Apr. 2008).

\* cited by examiner k l m

SEQUENCE LISTING

```
<160> NUMBER OF SEQ ID NOS: 17

<210> SEQ ID NO 1
<211> LENGTH: 1
<212> TYPE: DNA
<213> ORGANISM: Artificial Sequence
<220> FEATURE:
<223> OTHER INFORMATION: 1 G-rich segment
<220> FEATURE:
<221> NAME/KEY: repeat_unit
<222> LOCATION: (1)..(1)
<223> OTHER INFORMATION: repeated 1-6 times

<400> SEQUENCE: 1 g                                                                       1

<210> SEQ ID NO 2
<211> LENGTH: 3
<212> TYPE: DNA
<213> ORGANISM: Artificial Sequence
<220> FEATURE:
<223> OTHER INFORMATION: 2 G-rich segments
<220> FEATURE:
<221> NAME/KEY: repeat_unit
<222> LOCATION: (1)..(1)
<223> OTHER INFORMATION: repeated 1-6 times
<220> FEATURE:
<221> NAME/KEY: repeat_unit
<222> LOCATION: (2)..(2)
<223> OTHER INFORMATION: repeated 0-50 times
<220> FEATURE:
<221> NAME/KEY: misc_feature
<222> LOCATION: (2)..(2)
<223> OTHER INFORMATION: n is a, c, g, t or u
<220> FEATURE:
<221> NAME/KEY: repeat_unit
<222> LOCATION: (3)..(3)
```

-continued

```
<223> OTHER INFORMATION: repeated 1-6 times

<400> SEQUENCE: 2 gng                                                                          3

<210> SEQ ID NO 3
<211> LENGTH: 5
<212> TYPE: DNA
<213> ORGANISM: Artificial Sequence
<220> FEATURE:
<223> OTHER INFORMATION: 3 G-Rich segments
<220> FEATURE:
<221> NAME/KEY: repeat_unit
<222> LOCATION: (1)..(1)
<223> OTHER INFORMATION: repeated 1-6 times
<220> FEATURE:
<221> NAME/KEY: repeat_unit
<222> LOCATION: (2)..(2)
<223> OTHER INFORMATION: repeated 0-50 times
<220> FEATURE:
<221> NAME/KEY: misc_feature
<222> LOCATION: (2)..(2)
<223> OTHER INFORMATION: n is a, c, g, t or u
<220> FEATURE:
<221> NAME/KEY: repeat_unit
<222> LOCATION: (3)..(3)
<223> OTHER INFORMATION: repeated 1-6 times
<220> FEATURE:
<221> NAME/KEY: repeat_unit
<222> LOCATION: (4)..(4)
<223> OTHER INFORMATION: repeated 0-50 times
<220> FEATURE:
<221> NAME/KEY: misc_feature
<222> LOCATION: (4)..(4)
<223> OTHER INFORMATION: n is a, c, g, t or u
<220> FEATURE:
<221> NAME/KEY: repeat_unit
<222> LOCATION: (5)..(5)
<223> OTHER INFORMATION: repeated 1-6 times

<400> SEQUENCE: 3 gngng                                                                        5

<210> SEQ ID NO 4
<211> LENGTH: 7
<212> TYPE: DNA
<213> ORGANISM: Artificial Sequence
<220> FEATURE:
<223> OTHER INFORMATION: 4 G-rich segments or partial G-rich segments
<220> FEATURE:
<221> NAME/KEY: repeat_unit
<222> LOCATION: (1)..(1)
<223> OTHER INFORMATION: repeated 1-6 times
<220> FEATURE:
<221> NAME/KEY: repeat_unit
<222> LOCATION: (2)..(2)
<223> OTHER INFORMATION: repeated 0-50 times
<220> FEATURE:
<221> NAME/KEY: misc_feature
<222> LOCATION: (2)..(2)
<223> OTHER INFORMATION: n is a, c, g, t or u
<220> FEATURE:
<221> NAME/KEY: repeat_unit
<222> LOCATION: (3)..(3)
<223> OTHER INFORMATION: repeated 1-6 times
<220> FEATURE:
<221> NAME/KEY: repeat_unit
<222> LOCATION: (4)..(4)
<223> OTHER INFORMATION: repeated 0-50 times
<220> FEATURE:
<221> NAME/KEY: misc_feature
<222> LOCATION: (4)..(4)
<223> OTHER INFORMATION: n is a, c, g, t or u
<220> FEATURE:
<221> NAME/KEY: repeat_unit
```

```
<222> LOCATION: (5)..(5)
<223> OTHER INFORMATION: repeated 1-6 times
<220> FEATURE:
<221> NAME/KEY: repeat_unit
<222> LOCATION: (6)..(6)
<223> OTHER INFORMATION: repeated 0-50 times
<220> FEATURE:
<221> NAME/KEY: misc_feature
<222> LOCATION: (6)..(6)
<223> OTHER INFORMATION: n is a, c, g, t or u
<220> FEATURE:
<221> NAME/KEY: repeat_unit
<222> LOCATION: (7)..(7)
<223> OTHER INFORMATION: repeated 1-6 times

<400> SEQUENCE: 4 gngngng                                                                    7

<210> SEQ ID NO 5
<211> LENGTH: 3
<212> TYPE: DNA
<213> ORGANISM: Artificial Sequence
<220> FEATURE:
<223> OTHER INFORMATION: 1 G-rich segment
<220> FEATURE:
<221> NAME/KEY: repeat_unit
<222> LOCATION: (1)..(1)
<223> OTHER INFORMATION: repeated 0-50 times
<220> FEATURE:
<221> NAME/KEY: misc_feature
<222> LOCATION: (1)..(1)
<223> OTHER INFORMATION: n is a, c, g, t or u
<220> FEATURE:
<221> NAME/KEY: repeat_unit
<222> LOCATION: (2)..(2)
<223> OTHER INFORMATION: repeated 1 - 6 times
<220> FEATURE:
<221> NAME/KEY: repeat_unit
<222> LOCATION: (3)..(3)
<223> OTHER INFORMATION: repeated 0-50 times
<220> FEATURE:
<221> NAME/KEY: misc_feature
<222> LOCATION: (3)..(3)
<223> OTHER INFORMATION: n is a, c, g, t or u

<400> SEQUENCE: 5 ngn                                                                        3

<210> SEQ ID NO 6
<211> LENGTH: 5
<212> TYPE: DNA
<213> ORGANISM: Artificial Sequence
<220> FEATURE:
<223> OTHER INFORMATION: 2 G-rich segments
<220> FEATURE:
<221> NAME/KEY: repeat_unit
<222> LOCATION: (1)..(1)
<223> OTHER INFORMATION: repeated 0-50 times
<220> FEATURE:
<221> NAME/KEY: misc_feature
<222> LOCATION: (1)..(1)
<223> OTHER INFORMATION: n is a, c, g, t or u
<220> FEATURE:
<221> NAME/KEY: repeat_unit
<222> LOCATION: (2)..(2)
<223> OTHER INFORMATION: repeated 1-6 times
<220> FEATURE:
<221> NAME/KEY: repeat_unit
<222> LOCATION: (3)..(3)
<223> OTHER INFORMATION: repeated 0-50 times
<220> FEATURE:
<221> NAME/KEY: misc_feature
<222> LOCATION: (3)..(3)
<223> OTHER INFORMATION: n is a, c, g, t or u
<220> FEATURE:
```

```
<221> NAME/KEY: repeat_unit
<222> LOCATION: (4)..(4)
<223> OTHER INFORMATION: repeated 1-6 times
<220> FEATURE:
<221> NAME/KEY: repeat_unit
<222> LOCATION: (5)..(5)
<223> OTHER INFORMATION: repeated 0-50 times
<220> FEATURE:
<221> NAME/KEY: misc_feature
<222> LOCATION: (5)..(5)
<223> OTHER INFORMATION: n is a, c, g, t or u

<400> SEQUENCE: 6 ngngn                                                                5

<210> SEQ ID NO 7
<211> LENGTH: 7
<212> TYPE: DNA
<213> ORGANISM: Artificial Sequence
<220> FEATURE:
<223> OTHER INFORMATION: 3 G-rich segments
<220> FEATURE:
<221> NAME/KEY: repeat_unit
<222> LOCATION: (1)..(1)
<223> OTHER INFORMATION: repeated 0-50 times
<220> FEATURE:
<221> NAME/KEY: misc_feature
<222> LOCATION: (1)..(1)
<223> OTHER INFORMATION: n is a, c, g, t or u
<220> FEATURE:
<221> NAME/KEY: repeat_unit
<222> LOCATION: (2)..(2)
<223> OTHER INFORMATION: repeated 1-6 times
<220> FEATURE:
<221> NAME/KEY: repeat_unit
<222> LOCATION: (3)..(3)
<223> OTHER INFORMATION: repeated 0-50 times
<220> FEATURE:
<221> NAME/KEY: misc_feature
<222> LOCATION: (3)..(3)
<223> OTHER INFORMATION: n is a, c, g, t or u
<220> FEATURE:
<221> NAME/KEY: repeat_unit
<222> LOCATION: (4)..(4)
<223> OTHER INFORMATION: repeated 1-6 times
<220> FEATURE:
<221> NAME/KEY: repeat_unit
<222> LOCATION: (5)..(5)
<223> OTHER INFORMATION: repeated 0-50 times
<220> FEATURE:
<221> NAME/KEY: misc_feature
<222> LOCATION: (5)..(5)
<223> OTHER INFORMATION: n is a, c, g, t or u
<220> FEATURE:
<221> NAME/KEY: repeat_unit
<222> LOCATION: (6)..(6)
<223> OTHER INFORMATION: repeated 1-6 times
<220> FEATURE:
<221> NAME/KEY: repeat_unit
<222> LOCATION: (7)..(7)
<223> OTHER INFORMATION: repeated 0-50 times
<220> FEATURE:
<221> NAME/KEY: misc_feature
<222> LOCATION: (7)..(7)
<223> OTHER INFORMATION: n is a, c, g, t or u

<400> SEQUENCE: 7 ngngngn                                                              7

<210> SEQ ID NO 8
<211> LENGTH: 9
<212> TYPE: DNA
<213> ORGANISM: Artificial Sequence
<220> FEATURE:
<223> OTHER INFORMATION: 4 G-rich segments or partial G-rich segments
```

```
<220> FEATURE:
<221> NAME/KEY: repeat_unit
<222> LOCATION: (1)..(1)
<223> OTHER INFORMATION: repeated 0-50 times
<220> FEATURE:
<221> NAME/KEY: misc_feature
<222> LOCATION: (1)..(1)
<223> OTHER INFORMATION: n is a, c, g, t or u
<220> FEATURE:
<221> NAME/KEY: repeat_unit
<222> LOCATION: (2)..(2)
<223> OTHER INFORMATION: repeated 1-6 times
<220> FEATURE:
<221> NAME/KEY: repeat_unit
<222> LOCATION: (3)..(3)
<223> OTHER INFORMATION: repeated 0-50 times
<220> FEATURE:
<221> NAME/KEY: misc_feature
<222> LOCATION: (3)..(3)
<223> OTHER INFORMATION: n is a, c, g, t or u
<220> FEATURE:
<221> NAME/KEY: repeat_unit
<222> LOCATION: (4)..(4)
<223> OTHER INFORMATION: repeated 1-6 times
<220> FEATURE:
<221> NAME/KEY: repeat_unit
<222> LOCATION: (5)..(5)
<223> OTHER INFORMATION: repeated 0-50 times
<220> FEATURE:
<221> NAME/KEY: misc_feature
<222> LOCATION: (5)..(5)
<223> OTHER INFORMATION: n is a, c, g, t or u
<220> FEATURE:
<221> NAME/KEY: repeat_unit
<222> LOCATION: (6)..(6)
<223> OTHER INFORMATION: repeated 1-6 times
<220> FEATURE:
<221> NAME/KEY: repeat_unit
<222> LOCATION: (7)..(7)
<223> OTHER INFORMATION: repeated 0-50 times
<220> FEATURE:
<221> NAME/KEY: misc_feature
<222> LOCATION: (7)..(7)
<223> OTHER INFORMATION: n is a, c, g, t or u
<220> FEATURE:
<221> NAME/KEY: repeat_unit
<222> LOCATION: (8)..(8)
<223> OTHER INFORMATION: repeated 1-6 times
<220> FEATURE:
<221> NAME/KEY: repeat_unit
<222> LOCATION: (9)..(9)
<223> OTHER INFORMATION: repeated 0-50 times
<220> FEATURE:
<221> NAME/KEY: misc_feature
<222> LOCATION: (9)..(9)
<223> OTHER INFORMATION: n is a, c, g, t or u

<400> SEQUENCE: 8 ngngngngn                                                                 9

<210> SEQ ID NO 9
<211> LENGTH: 3
<212> TYPE: DNA
<213> ORGANISM: Artificial Sequence
<220> FEATURE:
<223> OTHER INFORMATION: Exemplary 2 G-rich segments
<220> FEATURE:
<221> NAME/KEY: repeat_unit
<222> LOCATION: (1)..(1)
<223> OTHER INFORMATION: repeated 2-6 times
<220> FEATURE:
<221> NAME/KEY: repeat_unit
<222> LOCATION: (2)..(2)
<223> OTHER INFORMATION: repeated 1-3 times
<220> FEATURE:
<221> NAME/KEY: repeat_unit
<222> LOCATION: (3)..(3)
```

```
<223> OTHER INFORMATION: repeated 2-6 times

<400> SEQUENCE: 9 gtg                                                                        3

<210> SEQ ID NO 10
<211> LENGTH: 5
<212> TYPE: DNA
<213> ORGANISM: Artificial Sequence
<220> FEATURE:
<223> OTHER INFORMATION: Exemplary 3 G-rich segments
<220> FEATURE:
<221> NAME/KEY: repeat_unit
<222> LOCATION: (1)..(1)
<223> OTHER INFORMATION: repeated 2-6 times
<220> FEATURE:
<221> NAME/KEY: repeat_unit
<222> LOCATION: (2)..(2)
<223> OTHER INFORMATION: repeated 1-3 times
<220> FEATURE:
<221> NAME/KEY: repeat_unit
<222> LOCATION: (3)..(3)
<223> OTHER INFORMATION: repeated 2-6 times
<220> FEATURE:
<221> NAME/KEY: repeat_unit
<222> LOCATION: (4)..(4)
<223> OTHER INFORMATION: repeated 1-3 times
<220> FEATURE:
<221> NAME/KEY: repeat_unit
<222> LOCATION: (5)..(5)
<223> OTHER INFORMATION: repeated 2-6 times

<400> SEQUENCE: 10 gtgtg                                                                      5

<210> SEQ ID NO 11
<211> LENGTH: 25
<212> TYPE: DNA
<213> ORGANISM: Artificial Sequence
<220> FEATURE:
<223> OTHER INFORMATION: oligonucleotide with G-rich segments

<400> SEQUENCE: 11
tctcgtgaca gcgtcattgt acgtc                                               25

<210> SEQ ID NO 12
<211> LENGTH: 61
<212> TYPE: DNA
<213> ORGANISM: Artificial Sequence
<220> FEATURE:
<223> OTHER INFORMATION: oligonucleotide with G-rich segments

<400> SEQUENCE: 12
ctctaatcga aagtagggtg ggtgggtggg tagtaagacg tacaatgatg ctgtcacgag         60
a                                                                         61

<210> SEQ ID NO 13
<211> LENGTH: 60
<212> TYPE: DNA
<213> ORGANISM: Artificial Sequence
<220> FEATURE:
<223> OTHER INFORMATION: oligonucleotide with G-rich segments

<400> SEQUENCE: 13
tcgctctaat cgaaagtagg gtgggtgggt agtaagacgt acaatgatgc tgtcacgaga         60

<210> SEQ ID NO 14
<211> LENGTH: 22
```

```
<212> TYPE: DNA
<213> ORGANISM: Artificial Sequence
<220> FEATURE:
<223> OTHER INFORMATION: oligonucleotide with G-rich segment

<400> SEQUENCE: 14
tgggtacttt cgattagagc ga                                              22

<210> SEQ ID NO 15
<211> LENGTH: 21
<212> TYPE: DNA
<213> ORGANISM: Artificial Sequence
<220> FEATURE:
<223> OTHER INFORMATION: control sequence

<400> SEQUENCE: 15
ccctactttc gattagagcg a                                               21

<210> SEQ ID NO 16
<211> LENGTH: 11
<212> TYPE: DNA
<213> ORGANISM: Artificial Sequence
<220> FEATURE:
<223> OTHER INFORMATION: Second nucleotide sequence

<400> SEQUENCE: 16
gggtgggtgg g                                                          11

<210> SEQ ID NO 17
<211> LENGTH: 18
<212> TYPE: DNA
<213> ORGANISM: Artificial Sequence
<220> FEATURE:
<223> OTHER INFORMATION: Isolated oligonucleotide targeting 3R comprises
      the first nucleotide sequence

<400> SEQUENCE: 17
tactttcgat tagagcga                                                   18
```

SITE-SPECIFIC INDUCTION OF BIMOLECULAR QUADRUPLEX-DUPLEX HYBRIDS AND METHODS OF USING THE SAME

STATEMENT REGARDING SEQUENCE LISTING

The Sequence Listing associated with this application is provided in text format in lieu of a paper copy, and is hereby incorporated by reference into the specification. The name of the text file containing the Sequence Listing is 690148 487USPC_SEQUENCE_LISTING.txt. The text file is 8.7 KB, was created on Jun. 18, 2015, and is being submitted electronically via EFS-Web.

FIELD OF THE INVENTION

The present invention relates to methods for controlling nucleic acid structures.

BACKGROUND OF THE INVENTION

Specific modulation of gene expression is an important goal in molecular biology and medicine. To this end, anti-gene and antisense oligonucleotide targeting represents an attractive strategy through the complementarity provided by the targeting oligonucleotide, typically ~15-30 nucleotides long.

The antigene approach involves specific binding of a DNA segment with hybridisable oligonucleotides for transcriptional regulation of the target gene (Hélène, C.; Toulme, J. J. Biochim. Biophys. Acta 1990, 1049, 99.). This could occur through formation of triple helix (Felsenfeld, G.; Davies, D. R.; Rich, A. J. Am. Chem. Soc. 1957, 79, 2023. and Moser, H. E.; Dervan, P. B. Science 1987, 238, 645) or through strand displacement, (Nielsen, P. E.; Egholm, M.; Berg, R. H.; Buchardt, O. Science 1991, 254, 1497.) in which the antigene oligonucleotide exhibits stronger affinity for the target strand as compared to its native counterpart.

The antisense approach, on the other hand, involves targeting of single-stranded mRNAs with complementary oligonucleotides for gene regulation at the translational level (Uhlmann, E.; Peyman, A. Chem Rev 1990, 90, 543.). Upon binding its target mRNA, the antisense oligonucleotide either triggers degradation of the mRNA by RNase H-dependent mechanism, or inhibits the translational machinery by acting as a steric block.

Binding affinity, stability, and effectiveness of antigene and antisense oligonucleotides can be enhanced with the use of modified nucleotides such as peptide nucleic acids (Nielsen et al.) (PNAs) and locked nucleic acids (Obika, S.; Nanbu, D.; Hari, Y.; Morio, K.; In, Y.; Ishida, T.; Imanishi, T. Tetrahedron Lett. 1997, 38, 8735. and Koshkin, A. A.; Singh, S. K.; Nielsen, P.; Rajwanshi, V. K.; Kumar, R.; Meldgaard, M.; Olsen, C. E.; Wengel, J. Tetrahedron 1998, 54, 3607.) (LNAs), or through the conjugation of strong nucleic acid binders such as intercalators (Sun, J. S.; Francois, J. C.; Montenaygarestier, T.; Saisonbehmoaras, T.; Roig, V.; Thuong, N. T.; Hélène, C. Proc. Natl. Acad. Sci. USA 1989, 86, 9198.).

Aside from the canonical B-form double helix (Watson, J. D.; Crick, F. H. C. Nature 1953, 171, 737.; Wilkins, M. H. F.; Stokes, A. R.; Wilson, H. R. Nature 1953, 171, 738. and Franklin, R. E.; Gosling, R. G. Nature 1953, 171, 740.) (or duplex), DNA can also adopt alternative structures such as G-quadruplex. (Simonsson, T. Biol. Chem. 2001, 382, 621.; Davis, J. T. Angew. Chem. Int. Edn. Engl. 2004, 43, 668.; Burge, S.; Parkinson, G. N.; Hazel, P.; Todd, A. K.; Neidle, S. Nucleic Acids Res. 2006, 34, 5402. and Patel, D. J.; Phan, A. T.; Kuryavyi, V. Nucleic Acids Res. 2007, 35, 7429.) The G-quadruplex is a four-stranded helical assembly made up of multiple stacked G•G•G•G tetrads, (M. Gellert, M. N. Lipsett, D. R. Davies, Proc. Natl. Acad. Sci. USA 1962, 48, 2013-2018.) with a diverse range of possible topologies. The G-quadruplex first rose into prominence with the findings that G-rich sequences could adopt such structures under physiological conditions (Sen, D.; Gilbert, W. Nature 1988, 334, 364.; Sundquist, W. I.; Klug, A. Nature 1989, 342, 825. and Williamson, J. R.; Raghuraman, M. K.; Cech, T. R. Cell 1989, 59, 871). It has since been shown that putative quadruplex sequences of the generic form $G_{3+}N_{1-7}G_{3+}N_{1-7}G_{3+}N_{1-7}G_{3+}$ are prevalent in the human genome (Todd, A. K.; Johnston, M.; Neidle, S. Nucleic Acids Res. 2005, 33, 2901. and Huppert, J. L.; Balasubramanian, S. Nucleic Acids Res. 2005, 33, 2908.). They have been identified in various genomic locations including telomere, (Blackburn, E. H. Nature 1991, 350, 569.) gene promoter, (Eddy, J.; Maizels, N. Nucleic Acids Res. 2006, 34, 3887. and Huppert, J. L.; Balasubramanian, S. Nucleic. Acids Res. 2007, 35, 406.) minisatellite, (Mitani, K.; Takahashi, Y.; Kominami, R. J. Biol. Chem. 1990, 265, 15203.) and immunoglobulin class switch region (Shimizu, A.; Honjo, T. Cell 1984, 36, 801.). A number of recent studies implicated the involvement of G-quadruplexes in cellular processes such as recombination (Cahoon, L. A.; Seifert, H. S. Science 2009, 325, 764) and replication, (Paeschke, K.; Capra, J. A.; Zakian, V. A. Cell 2011, 145, 678. and Lopes, J.; Piazza, A.; Bermejo, R.; Kriegsman, B.; Colosio, A.; Teulade-Fichou, M. P.; Foiani, M.; Nicolas, A. EMBO J. 2011, 30, 4033.) corroborating their biological relevance.

It has been proposed that promoter quadruplexes may be directly involved in transcriptional regulation (Huppert, J. L.; Balasubramanian, S. Nucleic Acids Res. 2007, 35, 406.). The first evidence came from studies on quadruplex formations in the promoter region of the oncogene c-myc; (Simonsson, T.; Pecinka, P.; Kubista, M. Nucleic Acids Res. 1998, 26, 1167.; Phan, A. T.; Modi, Y. S.; Patel, D. J. J. Am. Chem. Soc. 2004, 126, 8710.; Ambrus, A.; Chen, D.; Dai, J. X.; Jones, R. A.; Yang, D. Z. Biochemistry 2005, 44, 2048. and Phan, A. T.; Kuryavyi, V.; Gaw, H. Y.; Patel, D. J. Nat. Chem. Biol. 2005, 1, 167.) stabilization of the c-myc promoter quadruplex by the quadruplex-selective small molecule TMPyP4 led to a down-regulation of c-myc transcription (Siddiqui-Jain, A.; Grand, C. L.; Bearss, D. J.; Hurley, L. H. Proc. Natl. Acad. Sci. USA 2002, 99, 11593.). G-rich sequences in other promoters were subsequently identified and their quadruplex structures have been characterized. These include c-kit, (Rankin, S.; Reszka, A. P.; Huppert, J.; Zloh, M.; Parkinson, G. N.; Todd, A. K.; Ladame, S.; Balasubramanian, S.; Neidle, S. J. Am. Chem. Soc. 2005, 127, 10584.; Fernando, H.; Reszka, A. P.; Huppert, J.; Ladame, S.; Rankin, S.; Venkitaraman, A. R.; Neidle, S.; Balasubramanian, S. Biochemistry 2006, 45, 7854.; Phan, A. T.; Kuryavyi, V.; Burge, S.; Neidle, S.; Patel, D. J. J. Am. Chem. Soc. 2007, 129, 4386.; Gunaratnam, M.; Swank, S.; Haider, S. M.; Galesa, K.; Reszka, A. P.; Beltran, M.; Cuenca, F.; Fletcher, J. A.; Neidle, S. J. Med. Chem. 2009, 52, 3774.; Hsu, S. T. D.; Varnai, P.; Bugaut, A.; Reszka, A. P.; Neidle, S.; Balasubramanian, S. J. Am. Chem. Soc. 2009, 131, 13399.; Kuryavyi, V.; Phan, A. T.; Patel, D. J. Nucleic Acids Res. 2010, 38, 6757. and Wei, D. G.; Parkinson, G. N.; Reszka, A. P.; Neidle, S. Nucleic Acids Res. 2012, 40, 4691.) BCL-2, (Dai, J. X.; Chen; D.; Jones, R. A.; Hurley, L. H.;

Yang, D. Z. *Nucleic Acids Res.* 2006, 34, 5133). KRAS, (Cogoi, S.; Xodo, L. E. *Nucleic Acids Res.* 2006, 34, 2536.) RET, (Guo, K.; Pourpak, A.; Beetz-Rogers, K.; Gokhale, V.; Sun, D.; Hurley, L. H. *J. Am. Chem. Soc.* 2007, 129, 10220. and Tong, X. T.; Lan, W. X.; Zhang, X.; Wu, H. M.; Liu, M. L.; Cao, C. Y. *Nucleic Acids Res.* 2011, 39, 6753.) and hTERT (Palumbo, S. L.; Ebbinghaus, S. W.; Hurley, L. H. *J. Am. Chem. Soc.* 2009, 131, 10878.; Lim, K. W.; Lacroix, L.; Yue, D. J. E.; Lim, J. K. C.; Um, J. M. W.; Phan, A. T. *J. Am. Chem. Soc.* 2010, 132, 12331. and Micheli, E.; Martufi, M.; Cacchione, S.; De Santis, P.; Savino, M. *Biophys. Chem.* 2010, 153, 43.) promoter G-quadruplexes. Furthermore, bioinformatics analyses have revealed a high occurrence of these motifs in oncogenic promoters (Eddy, J. and Maizels, N.; and Huppert, J. L. et al.). Development of specific G-quadruplex ligands targeting indigenous quadruplex-forming sequences within oncogenic promoters has thus become an attractive anticancer strategy (Balasubramanian, S.; Neidle, S. *Curr. Opin. Chem. Biol.* 2009, 13, 345. and Balasubramanian, S.; Hurley, L. H.; Neidle, S. *Nat. Rev. Drug Discov.* 2011, 10, 261.).

In canonical B-DNA, right-handed antiparallel polynucleotide chains are held together by Watson-Crick base pairs (FIG. 1*a*). The relative alignment of the two phosphate backbones defines the major and minor grooves, with a strand separation (henceforth defined as the distance between matching pairs of phosphate groups) of ~18 Å. The G-quadruplex, in contrast, is stabilized by Hoogsteen hydrogen bonds and stacking interactions among the tetrad-forming guanine bases (FIG. 1*b*), with coordinating cations running through the middle channel. The diversity of G-quadruplex topologies arises from different relative orientations of the four strands constituting the G-tetrad core (FIG. 1*c*) and various possibilities of connecting them with linkers (known as loops). Each type of core has distinct groove dimensions (a combination of wide, medium or narrow grooves); a wide groove (flanked by antiparallel strands) has a strand separation of ~19 Å, a medium groove (flanked by parallel strands) has a strand separation of ~16 Å, while a narrow groove (flanked by antiparallel strands, arranged in the opposite strand directionalities with respect to the wide groove) has a strand separation of ~12 Å.

SUMMARY OF THE INVENTION

The present invention concerns the induction of a bimolecular quadruplex-duplex hybrid, formed between an isolated oligonucleotide molecule as described herein and a target nucleic acid molecule, based on the direct connectivity between duplex and quadruplex structural elements.

A first aspect of the present invention includes an isolated oligonucleotide molecule comprising or consisting of: (i) a first nucleotide sequence substantially complementary to a segment of target nucleic acid molecule to allow hybridization of the oligonucleotide molecule to said target; and (ii) a second nucleotide sequence comprising 1, 2, 3 or 4 G-rich segment/s or partial G-rich segment/s that complete the formation of a G-tetrad core in conjunction with the target nucleic acid molecule.

Another aspect of the present invention includes a method of controlling the topography of a target nucleic acid molecule comprising the steps of;
 a. contacting the target nucleic acid molecule with an isolated oligonucleotide molecule as described herein; wherein the isolated oligonucleotide molecule and the target nucleic acid molecule each comprises 1, 2, 3 or 4 G-rich segment/s or partial G-rich segment/s that can take part in the formation of a G-tetrad core and wherein the isolated oligonucleotide molecule and the target nucleic acid molecule combined comprise four segments that are capable of forming a G-tetrad core between the isolated oligonucleotide molecule and the target nucleic acid molecule.

Another aspect of the invention includes a method of controlling the structural topology of the quadruplex-duplex hybrid through sequence variation of the G-rich segment/s of the isolated oligonucleotide molecule.

Another aspect of the present invention includes a method of identifying a target nucleic acid sequence that is capable of forming a G-tetrad core in conjunction with an isolated oligonucleotide as described herein comprising the steps of:
 a. Searching for a nucleic acid sequence in a sequence database, wherein said sequence comprises 1, 2, 3 or 4 G-rich segment/s or partial G-rich segment/s that are capable of forming a G-tetrad core in conjunction with the isolated oligonucleotide as described herein;
 b. contacting the isolated oligonucleotide molecule as described herein with the target nucleic acid identified in (a); and
 c. observing whether the nucleic acid molecule identified in (a) is able to form a G-tetrad core in conjunction with the isolated oligonucleotide of (b).

Other aspects of the invention would be apparent to a person skilled in the art with reference to the following drawings and description of various non-limiting embodiments.

BRIEF DESCRIPTION OF THE DRAWINGS

The drawings are not necessarily drawn to scale, emphasis instead generally being placed upon illustrating the principles of various embodiments. In the following description, various embodiments of the invention are described with reference to the following exemplary drawings.

DETAILED DESCRIPTION OF THE INVENTION

In contrast to the conventional approach of ligand-based quadruplex targeting, which aims to selectively stabilize G-quadruplex structures adopted by indigenous quadruplex-forming sequences (FIG. 2a), the present invention involves the targeting of a nucleic acid fragment containing a partial quadruplex-forming sequence (incapable of forming a G-tetrad core by itself) with its complementary oligonucleotide, which harbors guanine/G-tract insert(s), for the specific induction of a bimolecular G-quadruplex structure (FIG. 2b-f).

Figure 3:
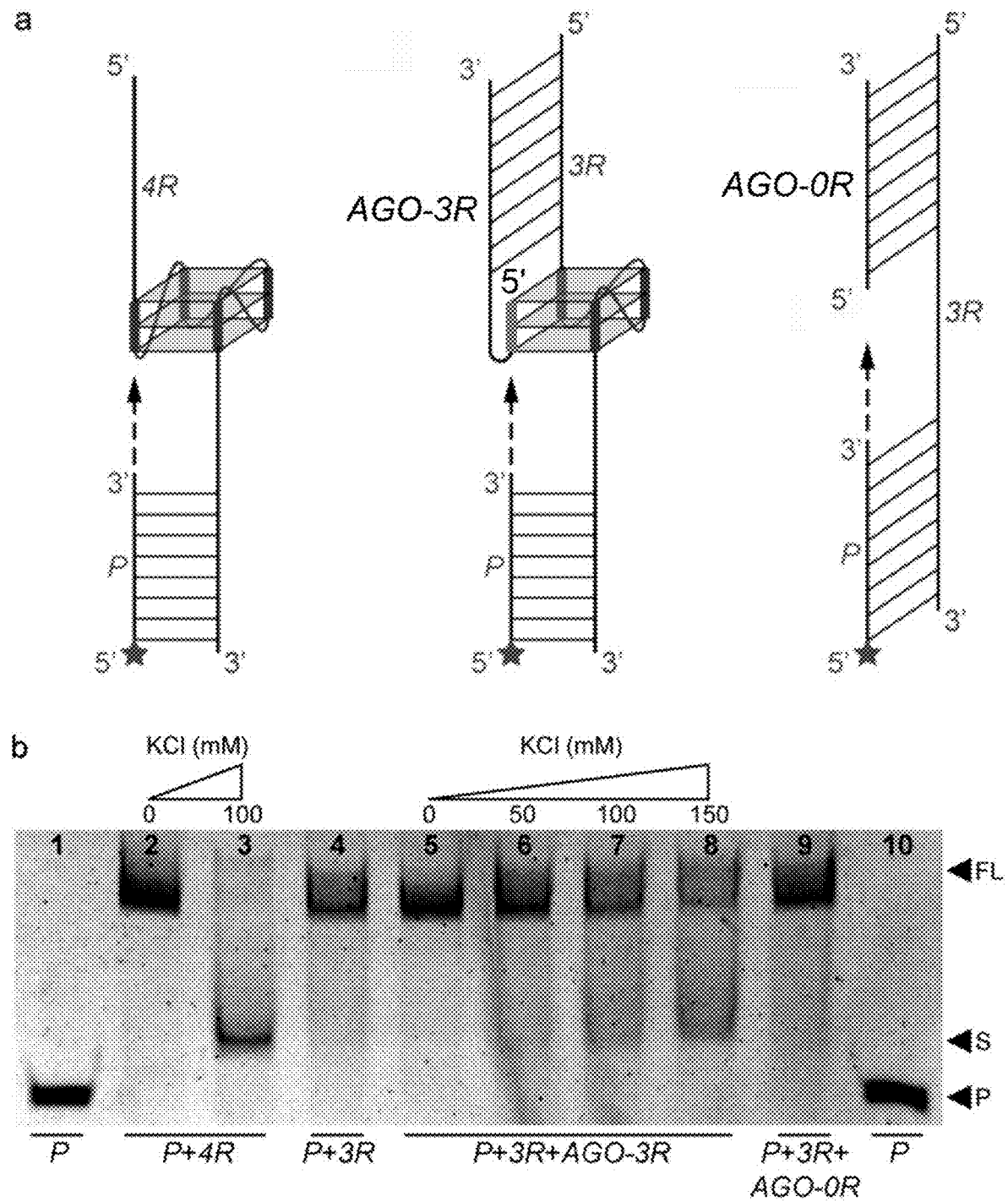
FIG. 3: DNA polymerase stop assays. a, Schematic diagram illustrating the experimental set-up. Color-coded as in FIG. 2. The primer contains a 6-FAM label (red star) at the 5'-end. Primer extension proceeds in the direction as shown. b, Denaturing polyacrylamide gel electrophoresis (PAGE) of primer extension products from 4R and 3R templates. In the case of 3R, extensions were carried out with the addition of AGO-3R or AGO-OR as well. Experiments were conducted either in the presence of 100 mM KCl (Lane 4 and 9) or with increasing concentrations of KCl as indicated (Lane 2-3 and 5-8). Lane 1 and 10 contain the non-extended primer. The bands corresponding to the primer (P), stop site (S), and full-length product (FL) are indicated with arrows.

The resulting complex can stall the progress of DNA polymerase (FIG. 3), allowing it to act as a steric block to replication.

This targeting strategy, when applied under the antigene/antisense context, could offer a direct route towards the selective modulation of gene expression. Binding of template DNA strand (antigene) or mRNA (antisense) by the targeting oligonucleotide and the subsequent induction of a quadruplex structure can lead to enhanced steric blockage of the transcriptional or translational machinery.

The present invention couples the specificity of Watson-Crick base pairing with the stability provided by a robust G-quadruplex scaffold. A comprehensive knowledge of the connectivity and stability associated with different types of quadruplex-duplex junction should help with the design of targeting oligonucleotides that tailor to different genomic sequences for G-quadruplex induction.

Accordingly, a first aspect of the invention includes an isolated oligonucleotide molecule comprising or consisting of: (i) a first nucleotide sequence substantially complementary to a segment of target nucleic acid molecule to allow hybridization of the oligonucleotide molecule to said target; and (ii) a second nucleotide sequence comprising 1, 2, 3 or 4 G-rich segment/s or partial G-rich segment/s that complete the formation of a G-tetrad core in conjunction with the target nucleic acid molecule.

The term "isolated oligonucleotide" as used herein refers to any nucleic acid molecule in any possible configuration, including single-stranded, double-stranded or a combination thereof. Isolated oligonucleotides include for instance DNA molecules, RNA molecules and analogues of DNA or RNA comprising modified backbones, internucleotide linkages, sugars or bases. DNA or RNA may be of genomic or synthetic origin. Such nucleic acids include but are not limited to mRNA, cRNA, synthetic RNA, genomic DNA, cDNA, synthetic DNA and DNA/RNA hybrid. Isolated oligonucleotides are either synthetic constructs or nucleic acids separated from other cellular components with which it may naturally occur including cellular debris or are synthesized using known methods. The resulting nucleic acids are preferably 70, 80 or 90% pure, preferably at least 95 or 98% pure nucleic acid containing less than 30% contaminants, preferably less than 20 or 10% and most preferably less than 5 or 2% contaminants that cannot be identified as the nucleic acid as described herein.

Various nucleotide analogues are known and can be incorporated as part of, or replaced in its entirety, the isolated oligonucleotide of the present invention. A nucleotide analogue as defined herein is a nucleotide modified at the backbone, internucleotide linkage, sugar or base moiety. Modifications at the backbone or internucleotide linkage moiety include peptide nucleic acid (PNA) and substitution of the phosphate group by phosphorothioate. Modifications at the sugar moiety include locked nucleic acid (LNA) and substitution of the 2'-OH group. Modifications at the base moiety include alterations to A, T/U, G and C, as well as various purine/pyrimidine or non-purine/pyrimidine bases. Modifications of these different moieties can be applied on the same nucleotide in concert. Incorporation of nucleotide analogues within the isolated oligonucleotide can lead to stronger binding affinity for the target nucleic acid or improved nuclease. resistance. For example, substitution of 2'-OH group of an siRNA with —F, —O—Me or —H was shown to improve its in vivo stability.

The term "complementary" refers to a sequence that is alignable against its counterpart within the antiparallel double helical context. Each nucleotide base aligns specifically with its complement base following the Watson-Crick base pairing. Accordingly, adenine (A) forms a base pair with thymine (T)/uracil (U) while guanine (G) forms a base pair with cytosine (C). The degree of hybridization between two nucleotide strands may vary from a complete 100% complementary match to at least 50% complementary match over a length of nucleotides. The complementary sequence is preferably of 5 to 100 base pairs in length, more preferably 8 to 50 base pairs in length, most preferably 15 to 30 base pairs in length. "Substantially complementary" as described herein indicates that the complementary sequence is preferably 80% complementary, more preferably 90% and most preferably 100% complementary to a segment of equal length on the target sequence. It is possible to design an oligonucleotide with the first nucleotide sequence substantially complementary to the target nucleic acid based on the sequence of the target nucleic acid as complementary bases are known.

The second nucleotide sequence comprising 1,2,3 or 4 G-rich segment/s or partial G-rich segment/s that complete the formation of a G-tetrad core with the target nucleic acid molecule comprises guanine or successive guanine nucleotides. In various embodiments said second nucleotide sequence is not able to form a stable G-tetrad core on its own, said second nucleotide sequence comprises or consists of the sequence $G_x$ (SEQ ID NO:1), $G_xN_yG_x$ (SEQ ID NO:2), $G_xN_yG_xN_yG_x$ (SEQ ID NO. 3) or $G_xN_yG_xN_yG_xN_yG_x$ (SEQ ID NO:4), wherein each x independently is an integer from 1-6 and represents the number of successive guanine nucleotides, and each y independently is an integer from 0-50 and represents the number of nucleotides separating two G-rich segments. In various embodiments said second nucleotide sequence comprises or consists of the nucleic acid sequence $N_yG_xN_y$ (SEQ ID NO:5), $N_yG_xN_yG_xN_y$ (SEQ ID NO:6), $N_yG_xN_yG_xN_yG_xN_y$ (SEQ ID NO:7) or $N_yG_x$-$N_yG_xN_yG_xN_yG_xN_y$ (SEQ ID NO:8). For SEQ ID NOs. 1 and 5 the target sequence includes 3 complete G-rich segments and in some cases 1 incomplete G-rich segment or partial G-rich segment, as illustrated in (e) and (f) of FIG. 2. Similarly, neither SEQ ID NOs 4 nor 8 are able to form a stable G-tetrad core on its own. In various embodiments one or more of the $N_y$ sequence segments in any one of SEQ ID Nos. 1-8, y is 5-50 and said one or more $N_y$ sequence segments are self-complementary and capable of forming a duplex stem-loop structure. In various embodiments one or more of the $N_y$ sequence segments in any one of SEQ ID Nos. 1 to 4, y may be 1-30, or 1-20, or 1-16, or 1-15, or 1-14. In various embodiments said second nucleotide sequence comprises or consists of the sequence $G_xT_yG_x$ (SEQ ID NO:9) or $G_xT_yG_xT_yG_x$ (SEQ ID NO:10), wherein x is an integer of 2-6, and y is 1, 2 or 3 and represents the number of successive thymine nucleotides. In various embodiments said second nucleotide sequence comprises the sequence GGG. In various embodiments said second nucleotide sequence comprises the sequence GGGTGGG. In various embodiments said second nucleotide sequence comprises the sequence GGGTGGGTGGG (SEQ ID NO: 16). In various embodiments said second nucleotide sequence comprises the sequence GGTTGG.

The term "G-quadruplex" refers to a four-stranded helical nucleic acid structure comprising multiple stacked G-tetrads, each of which consists of four guanine bases that associate in a cyclical manner through Hoogsteen hydrogen bonds and are further stabilized through coordination to a cation in the center. The body of stacked G-tetrads, comprising a total of 2-6 layers, is collectively referred to as the G-tetrad core. Each of the four guanine columns constituting the G-tetrad core can arise from a single (continuous column) or two (discontinuous column) separate guanine stretch/es. The term "bimolecular" as used herein refers to a G-tetrad core that is formed by two separate oligonucleotide strands, each of which comprises at least one G-rich segment or partial G-rich segment. In various embodiments the isolated oligonucleotide molecule constitutes 1,2 or 3 column/s of the G-tetrad core and the target oligonucleotide molecule constitutes 3,2 or 1, respectively, of the remaining column/s. In various other embodiments the isolated oligonucleotide molecule or the target nucleic acid molecule constitutes 3 complete columns and 1 incomplete column of the G-tetrad core and the counterpart molecule constitutes the remaining portion of the incomplete column. In this manner, the isolated oligonucleotide can be designed to induce a bimolecular G-quadruplex in conjunction with a wide variety of target sequences, including natural genomic sequences, that would otherwise have been considered incapable of forming G-quadruplex structures by themselves.

Another aspect of the present invention includes a method of controlling the topography of a target nucleic acid molecule comprising the steps of;
  a. contacting the target nucleic acid sequence with an isolated oligonucleotide molecule;
wherein the isolated oligonucleotide molecule and the target nucleic acid molecule each comprises 1, 2, 3 or 4 G-rich segment/s or partial G-rich segment/s that can take part in the formation of a G-tetrad core and wherein the isolated oligonucleotide molecule and the target nucleic acid molecule combined comprise four segments with a total of 8 (2 G-tetrad layers), 12 (3 G-tetrad layers), 16 (4 G-tetrad layers), 20 (5 G-tetrad layers) or 24 (6 G-tetrad layers) guanine bases that are capable of forming a G-tetrad core between the isolated oligonucleotide molecule and the target nucleic acid molecule.

An additional embodiment of the present invention is a method of controlling the structural topology of the quadruplex-duplex hybrid through sequence variation of the G-rich segment/s or partial G-rich segment/s of the isolated oligonucleotide molecule, which would be apparent to a person skilled in the art.

In various embodiments the target nucleic acid molecule comprises deoxyribonucleic acid (DNA), preferably genomic DNA. In various embodiments the method is suitable for modulating transcription of the target nucleic acid molecule. Preferably, the target sequence resides on the template strand of a functional gene coding for a protein of interest, more preferably the target sequence resides within the promoter region of said gene. The induction of a bimolecular G-quadruplex between the isolated oligonucleotide molecule and the target nucleic acid molecule can either prevent the assembly or progression of the transcriptional machinery, thereby resulting in inhibition of transcription of the target nucleic acid molecule.

In various embodiments the target nucleic acid molecule comprises ribonucleic acid (RNA), preferably messenger RNA (mRNA). In various embodiments the method is suitable for modulating translation of the target nucleic acid molecule. The target sequence can reside within the 5'-untranslated region (5'-UTR), 3'-UTR or open reading frame (ORF) of the mRNA. The induction of a bimolecular G-quadruplex between the isolated oligonucleotide molecule and the target nucleic acid molecule can either prevent the assembly or progression of the translational machinery, or trigger degradation of the mRNA through RNase H-dependent mechanism, thereby resulting in inhibition of translation of the target nucleic acid molecule.

In various preferred embodiments the method further comprises the step of adding cationic molecules to the target nucleic acid molecule and the isolated oligonucleotide molecule. Preferably the cationic molecule is potassium or sodium in their various monovalent forms. The cationic molecule is essential for the formation of G-quadruplex structures.

Another aspect of the present invention includes a method of identifying a target nucleic acid sequence that is capable of forming a G-tetrad core in conjunction with an isolated oligonucleotide as described herein comprising the steps of:
  a. Searching for a nucleic acid sequence in a sequence database, wherein said sequence comprises 1, 2, 3 or 4 G-rich segment/s or partial G-rich segment/s that are capable of forming a G-tetrad core in conjunction with the isolated oligonucleotide as described herein;
  b. contacting the isolated oligonucleotide molecule with the target nucleic acid identified in (a); and
  c. observing whether the nucleic acid molecule comprising the sequence identified in (a) is able to form a G-tetrad core in conjunction with the isolated oligonucleotide of (b).

The method allows the formation of stable G-quadruplex structures at genomic sites that would otherwise have been considered incapable of forming such stable structures by themselves, hence extending the modulation of gene expression in transcription or translation through G-quadruplex formation to these sites. In this way target sequences that contain only 1 G-rich segment, 2 G-rich segments or 3 G-rich segments can still form G-quadruplex structures by supplementing the missing G-rich segment/s of the target nucleotide with G-rich segment/s in a designed isolated oligonucleotide. This also applies to target nucleotide sequences that contain four G-rich segments but are incapable of forming a stable G-tetrad core, wherein the designed isolated oligonucleotide supplements the missing guanine nucleotide/s. The resultant G-quadruplex is bimolecular in nature, formed between the target nucleic acid molecule and the isolated oligonucleotide molecule. The target nucleic acid molecule contains 1, 2, 3 or 4 G-rich segment/s or partial G-rich segment/s. In various embodiments said segment/s comprise or consist of the sequence $G_x$ (SEQ ID NO:1), $G_xN_yG_x$ (SEQ ID NO:2), $G_xN_yG_xN_yG_x$ (SEQ ID NO. 3) or $G_xN_yG_xN_yG_xN_yG_x$ (SEQ ID NO:4), wherein each x independently is an integer from 1-6 and represents the number of successive guanine nucleotides, and each y independently is an integer from 0-50 and represents the number of nucleotides separating two G-rich segments. In various embodiments said segment/s comprise or consist of the nucleic acid sequence $N_yG_xN_y$ (SEQ ID NO:5), $N_yG_xN_yG_xN_y$ (SEQ ID NO:6), $N_yG_xN_yG_xN_yG_xN_y$ (SEQ ID NO:7) or $N_yG_xN_yG_xN_yG_xN_yG_xN_y$ (SEQ ID NO:8). In various embodiments one or more of the $N_y$ sequence segments in any one of SEQ ID Nos. 1-8, y is 5-50 and said one or more $N_y$ sequence segments are self-complementary and capable of forming a duplex stem-loop structure. In various embodiments said segment/s comprise or consist of the sequence $G_xT_yG_x$ (SEQ ID NO:9) or $G_xT_yG_xT_yG_x$ (SEQ ID NO:10), wherein x is an integer of 2-6, and y is 1, 2 or 3 and represents the number of successive thymine nucleotides. In various embodiments said segment/s comprise the sequence GGG. In various embodiments said segment/s comprise the sequence GGGTGGG. In various embodiments said segment/s comprise the sequence GGGTGGGTGGG (SEQ ID NO: 16). In various embodiments said segment/s comprise the sequence GGTTGG.

The isolated oligonucleotide can be subjected to further modifications for additional applications. These include but are not limited to the attachment of duplex-/quadruplex-binding ligands or fluorescent dyes to any segment of the molecule.

Formation of the bimolecular quadruplex-duplex hybrids provides unique structural features for the design of small molecules specifically targeting such structures upon their generation.

A nucleic acid nanoarchitecture comprising a G-quadruplex formed between an isolated oligonucleotide molecule and a target nucleic acid molecule can be generated site-specifically for nanotechnological applications.

The present invention is further illustrated by the following examples. However, it should be understood, that the invention is not limited to the exemplified embodiments.

EXAMPLES OF PREFERRED EMBODIMENTS

DNA Sample Preparation

DNA oligonucleotides were chemically synthesized on an ABI 394 DNA/RNA synthesizer using products from Glen Research. The oligonucleotides were de-protected following the manufacturer's protocols and purified using Poly-Pak™ cartridges. Samples were dialyzed successively against water, 20 mM KCl solution, and water again. They were subsequently frozen, lyophilized, and suspended in a buffer containing 20 mM potassium phosphate (pH 7.0) and 20 mM KCl. DNA concentration is expressed in strand molarity using a nearest-neighbor approximation for the absorption coefficients of the unfolded species. Sample concentrations were determined from UV absorbance at 260 nm, based on molar extinction coefficients provided by the online application 'UV Spectrum of DNA Calculator'.

Figure 1:
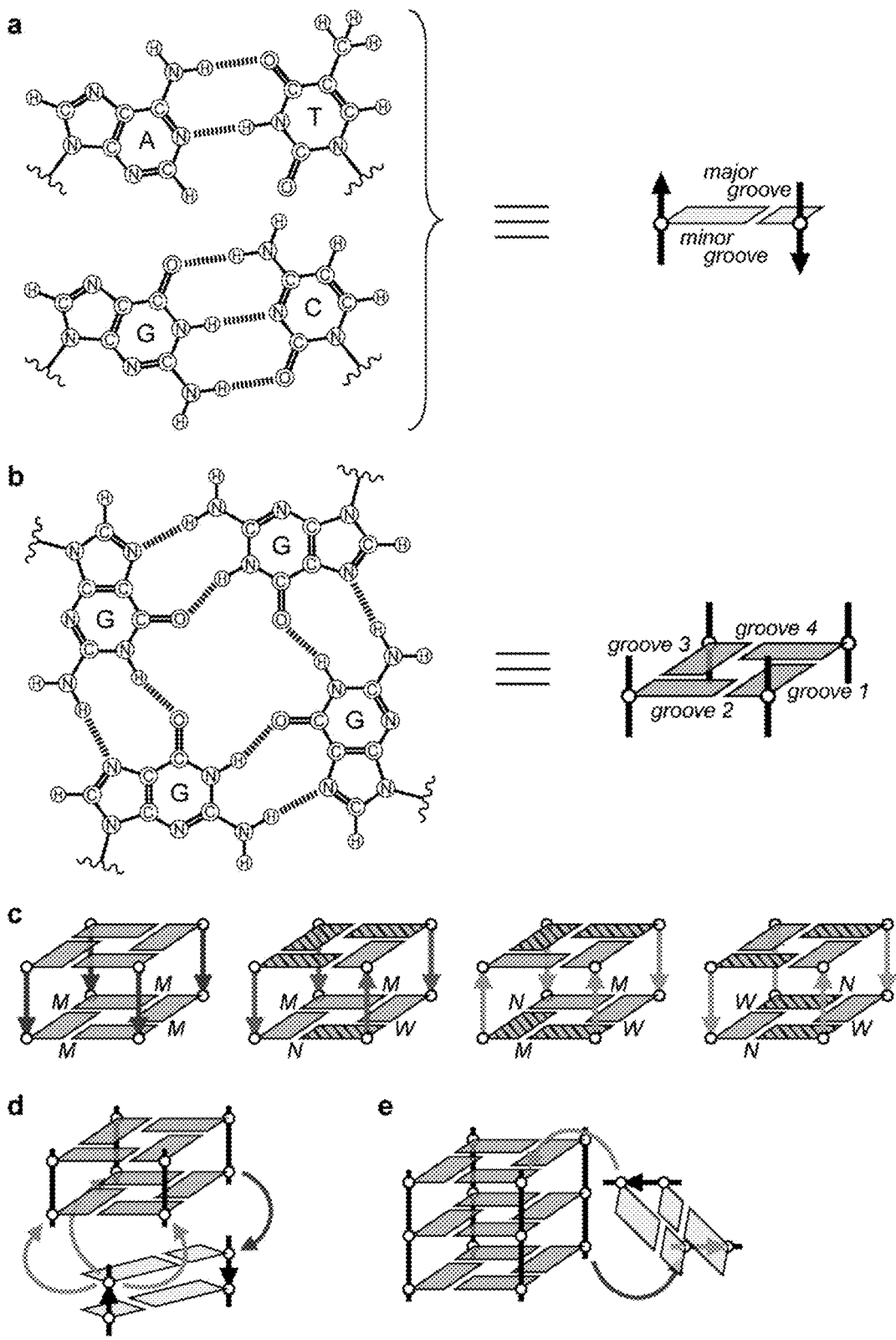
FIG. 1: Geometry of duplex and quadruplex DNA and their juxtaposition. a, Watson-Crick A•T and G•C base pairs. b, The G•G•G•G tetrad. c, Four classical G-quadruplex core topologies, each having a distinct arrangement of groove dimensions (W—wide, M—medium, and N—narrow). Guanine bases in syn conformation are shaded. d,e, Coaxial (d) and orthogonal (e) orientation of duplex and quadruplex helices at the quadruplex-duplex junction, shown here with a static (purple) and a variable (pink) attachment point for the two duplex strands.
Figure 2:
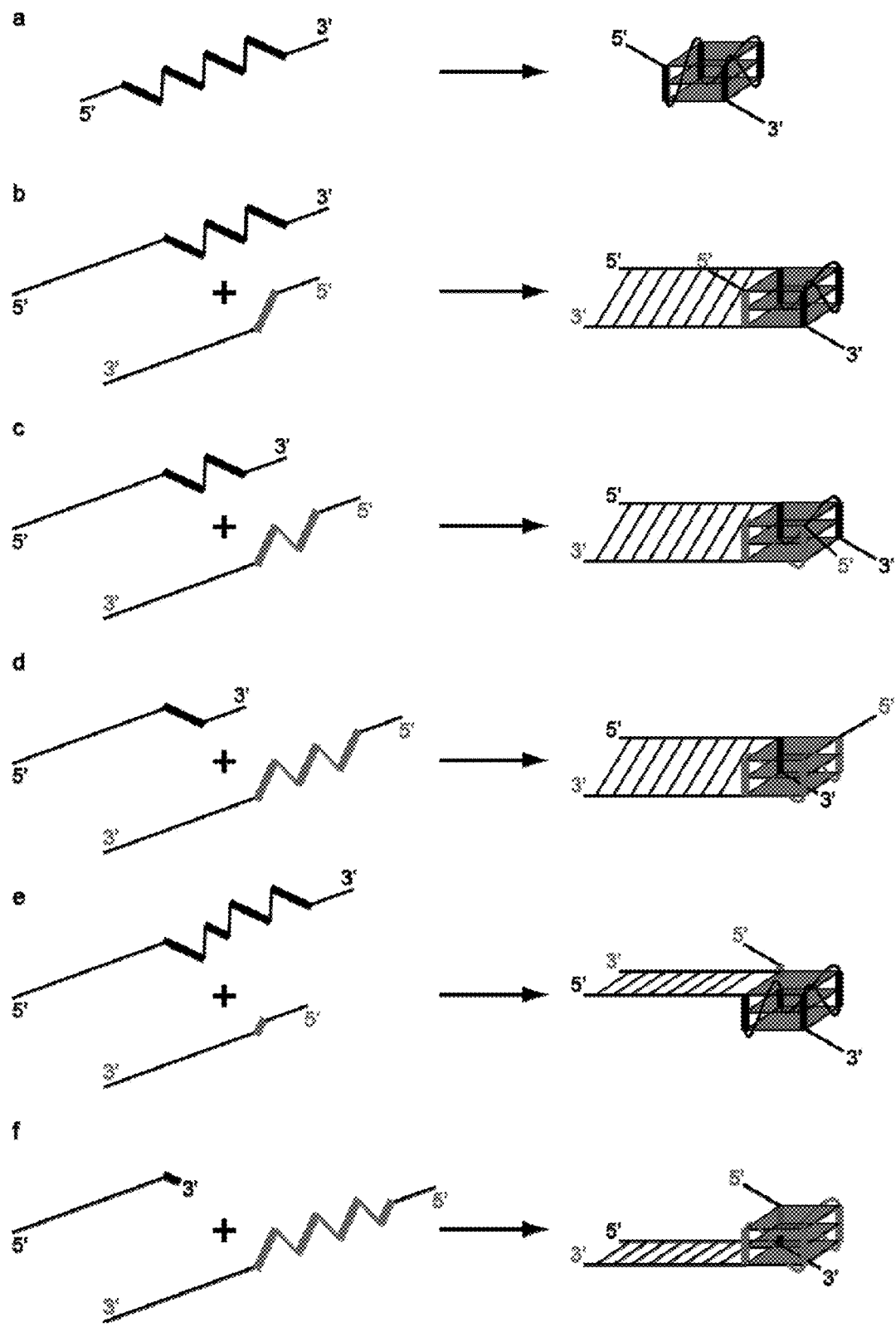
FIG. 2: G-quadruplex formation (a) from an indigenous quadruplex-forming sequence comprising four G-rich segment/s (G-tracts), and (b-f) from a partial quadruplex-forming sequence as induced by the binding of a complementary oligonucleotide containing a G-rich segment/s (or G-tract) insert. G-rich segments (or G-tracts) are depicted as thick lines.

Connectivity of Duplex and Quadruplex Structural Elements in Quadruplex-Duplex Hybrids To address the compatibility between duplex and quadruplex DNA, we explored the incorporation of a duplex hairpin across the various geometries of a quadruplex core. Conceptually, with a duplex strand joint with one strand of a tetrad core, there are at least three possibilities of connection for the second strand that could lead to coaxial orientation of the helices (FIG. 1d). Additionally, orthogonal connectivity of a duplex and a quadruplex (FIG. 1e) could be possible. A stable quadruplex-duplex junction could take form if duplex attachment for that particular arrangement is geometrically feasible and energetically favorable. Out of over twenty quadruplex-duplex constructs examined, we present here the high-resolution NMR structures of five representative constructs, each of which illustrates a disparate principle of connection between a duplex and a quadruplex. In each case, strategic placement of the hairpin and auxiliary structural elements culminated in a unique structure, and rigorous spectral assignment approaches were employed for structural characterization.

Figure 4:
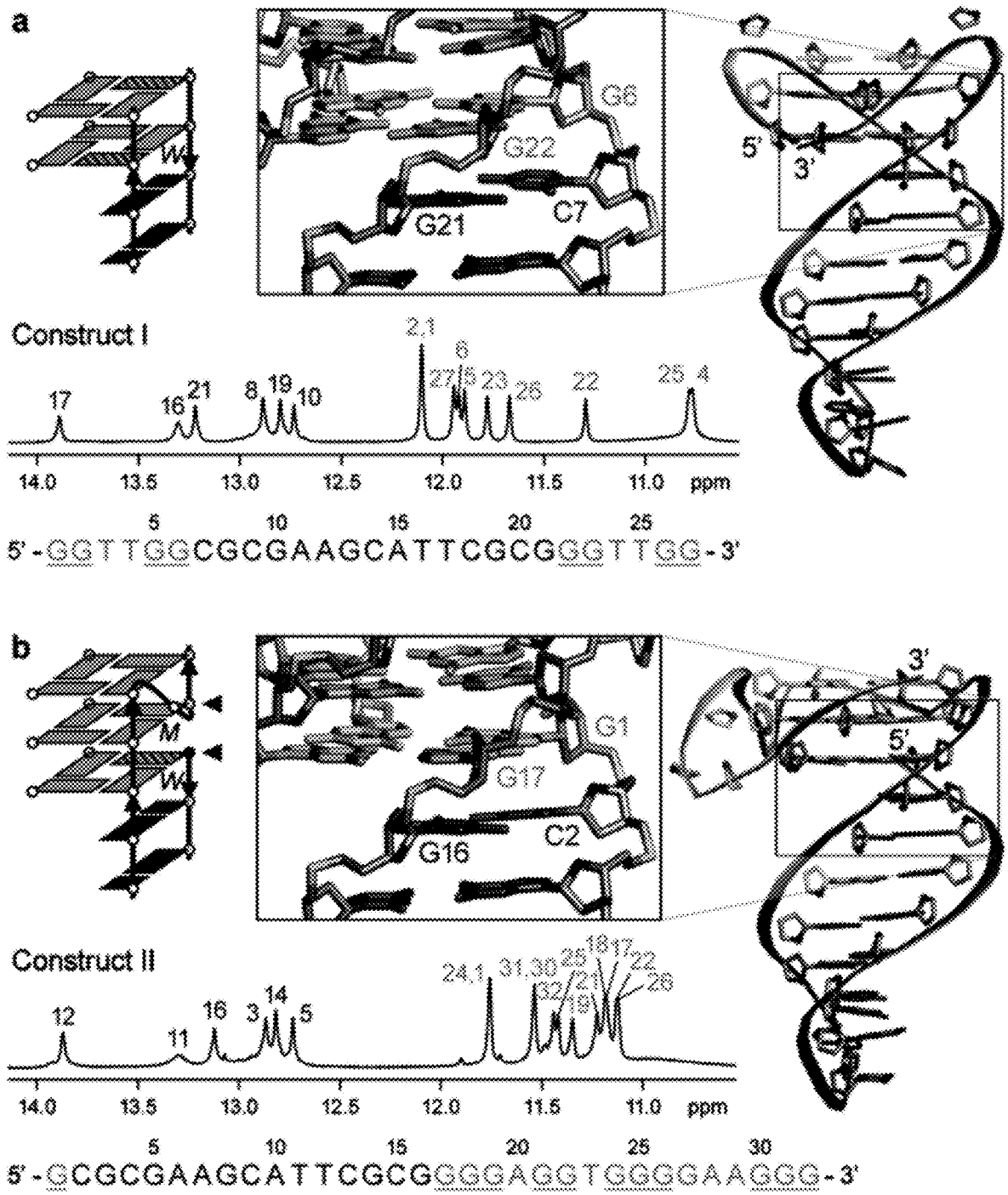
FIG. 4: Structures of quadruplex-hairpin constructs. Different duplex attachment strategies leading to the coaxial (a-d) and orthogonal (e) orientation of duplex and quadruplex helices at the quadruplex-duplex junctions. Ribbon view of a representative structure is shown in each panel together with the sequence (tetrad guanines underlined) and the 1D imino proton NMR spectrum of the construct. Structural details at the junctions are enlarged, accompanied by schematics illustrating the principles of connection. Bases from the quadruplex and duplex segments are colored in cyan and magenta, respectively; G•A Watson-Crick mismatch base pairs, orange; backbone and sugar, silver; O4' atoms, red; phosphorus atoms, yellow. a, A duplex can be extended continuously from the wide groove. b, Introduction of a nick onto a G-tract can accommodate a duplex across the medium-made-wide groove. c, An adaptor G•A base pair can be utilized to bridge a duplex across the diagonal corners of a tetrad. d, The snapback approach can be applied to sidestep the unfavorable connection of a duplex across the narrow groove, instead bridging the duplex across the same edge of the tetrad core through the diagonal corners. e, Sideway connectivity of a duplex, with the disruption of a base pair (highlighted as yellow circles in the schematic) at the junction.
Figure 4:
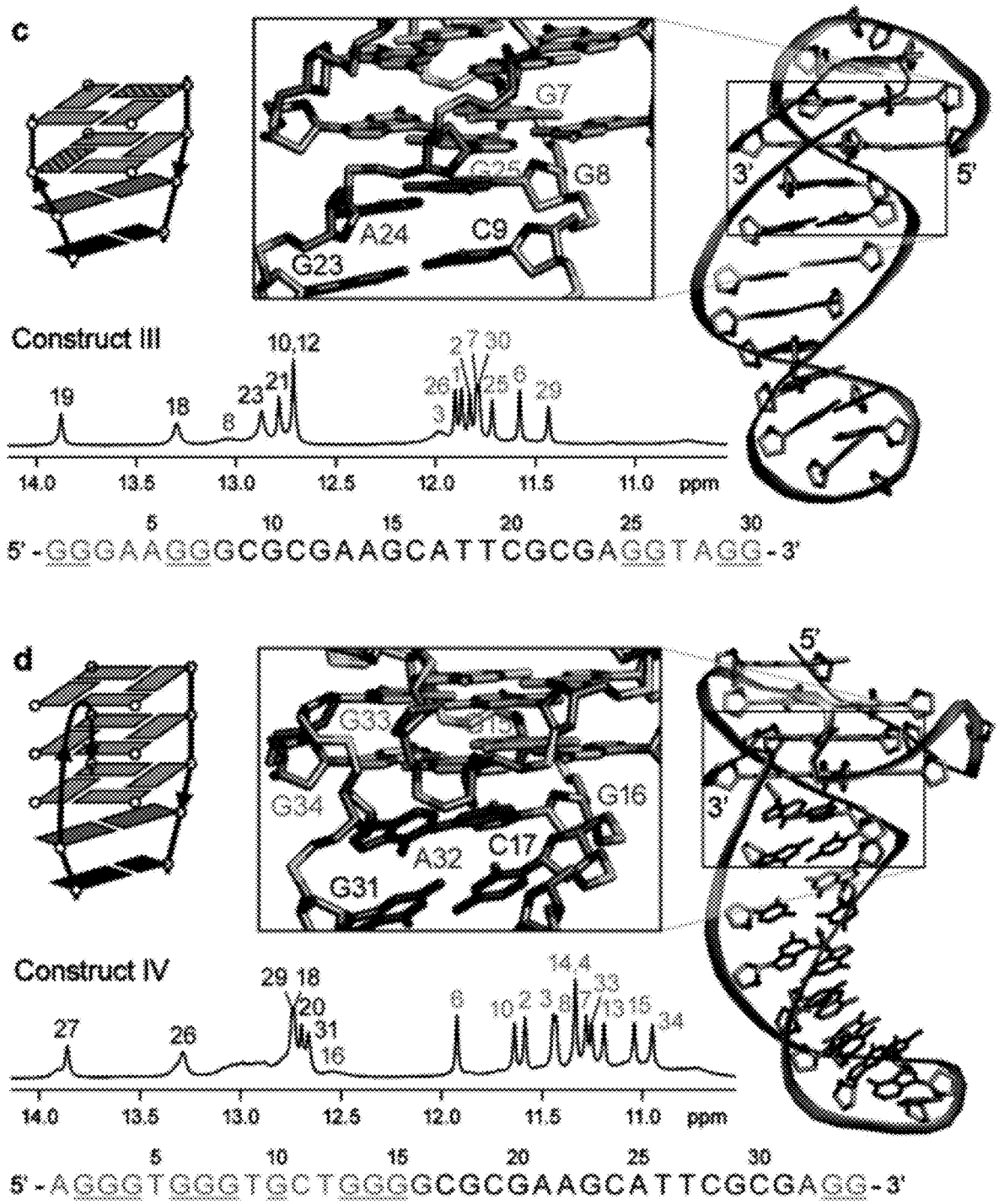
Figure 4:
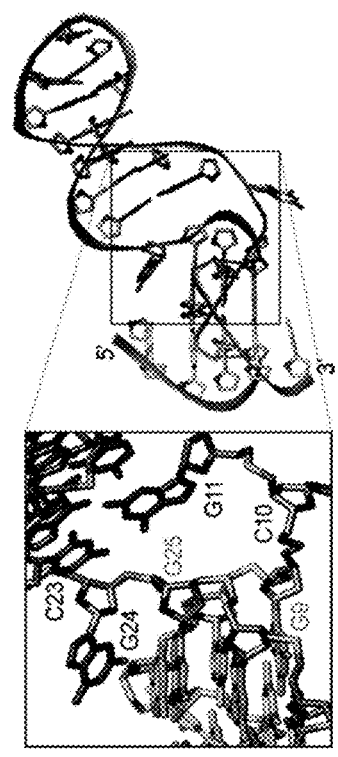
Figure 4:
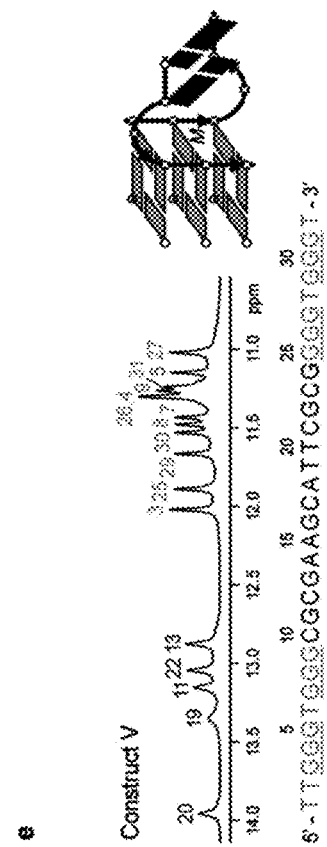
Figure 5:
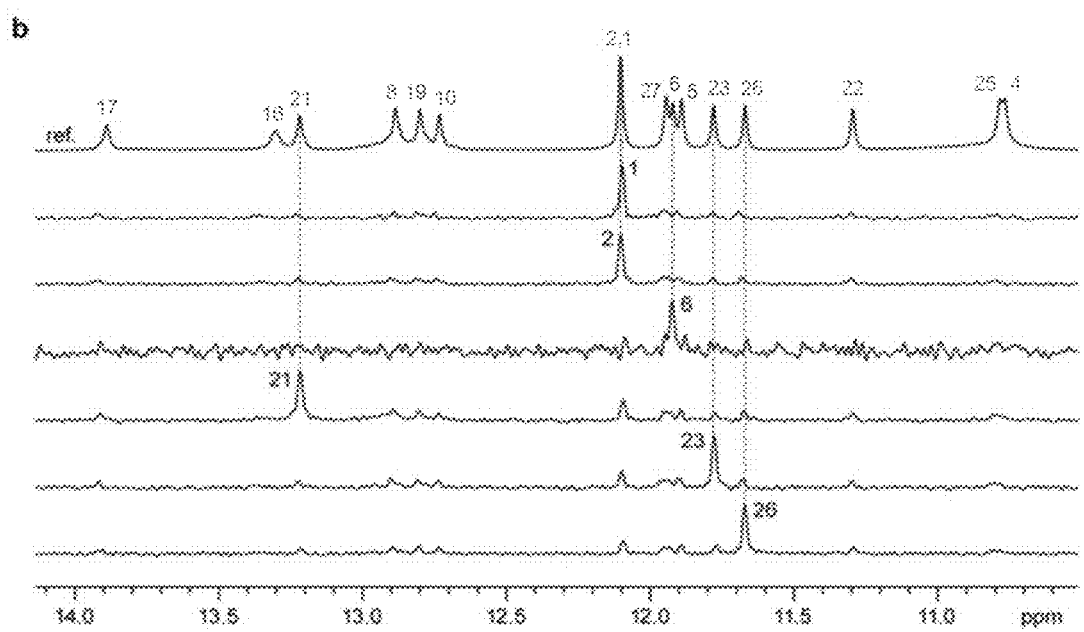
FIG. 5: NMR structural characterization of Construct I. a, Sequence of Construct I. b, Examples of imino proton assignments in $^{15}$N-filtered spectra of samples, 2% $^{15}$N-labeled at the indicated positions. The reference spectrum (ref.) is shown at the top. c, Examples of H8 proton assignments by site-specific $^2$H labeling at the indicated positions. The reference spectrum (ref.) is shown at the top. d, Through-bond correlations between guanine imino and H8 protons via $^{13}$C5 at natural abundance, using long-range J-couplings shown in the inset. Assignments are labeled with residue numbers. Different threshold levels are displayed for the left and right panes. e, NOESY spectrum (mixing time, 200 ms) showing the cross-peaks that identify the arrangement of the two G-tetrads and the Watson-Crick base pairs. Cross-peaks arising from imino-H8 connectivity around the two G-tetrads are framed in cyan and labeled with the residue number of imino proton in the first position and that of H8 proton in the second position. Cross-peaks between thymine imino proton and adenine H2 proton, and between guanine imino proton and cytosine amino protons, are framed in magenta and labeled with the residue number of thymine/guanine in the first position and that of adenine/cytosine in the second position. f, NOESY spectrum (mixing time, 300 ms) showing the H8/H6-H1' connectivity of Construct I. Intraresidue H8/H6-H1' NOE cross-peaks are labeled with residue numbers. g, NOEs from thymine imino proton to adenine H2 proton that establish the A11•T17 and A12•T16 base pairs. h, NOEs from guanine imino proton to cytosine amino protons that establish the G21•C7, G8•C20, G19•C9 and G10•C18 base pairs. i, Characteristic guanine imino-H8 NOE connectivity patterns around a $G_\alpha$•$G_\beta$•$G_\gamma$•$G_\delta$ tetrad as indicated with arrows, with the connectivities observed for the G2•G26•G23•G5 and G1•G6•G22•G27 tetrads shown below. j, Schematic diagram of Construct I. Quadruplex and hairpin segments are colored in cyan and magenta, respectively. The 5'- and 3'-termini are shown as red circles. Non-canonical base pairs are shown as dotted lines. k,l, Stereo views of ten superimposed refined structures (k) and a representative structure in ribbon representation (l). Structures are aligned based on the tetrad core.
Figure 5:
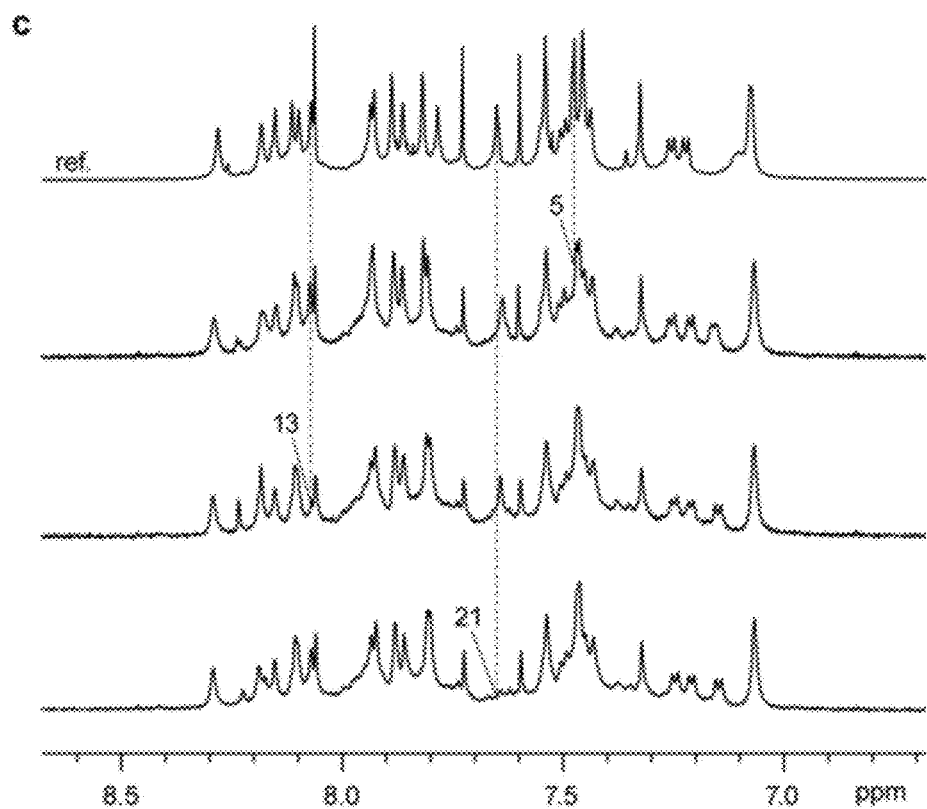
Figure 5:
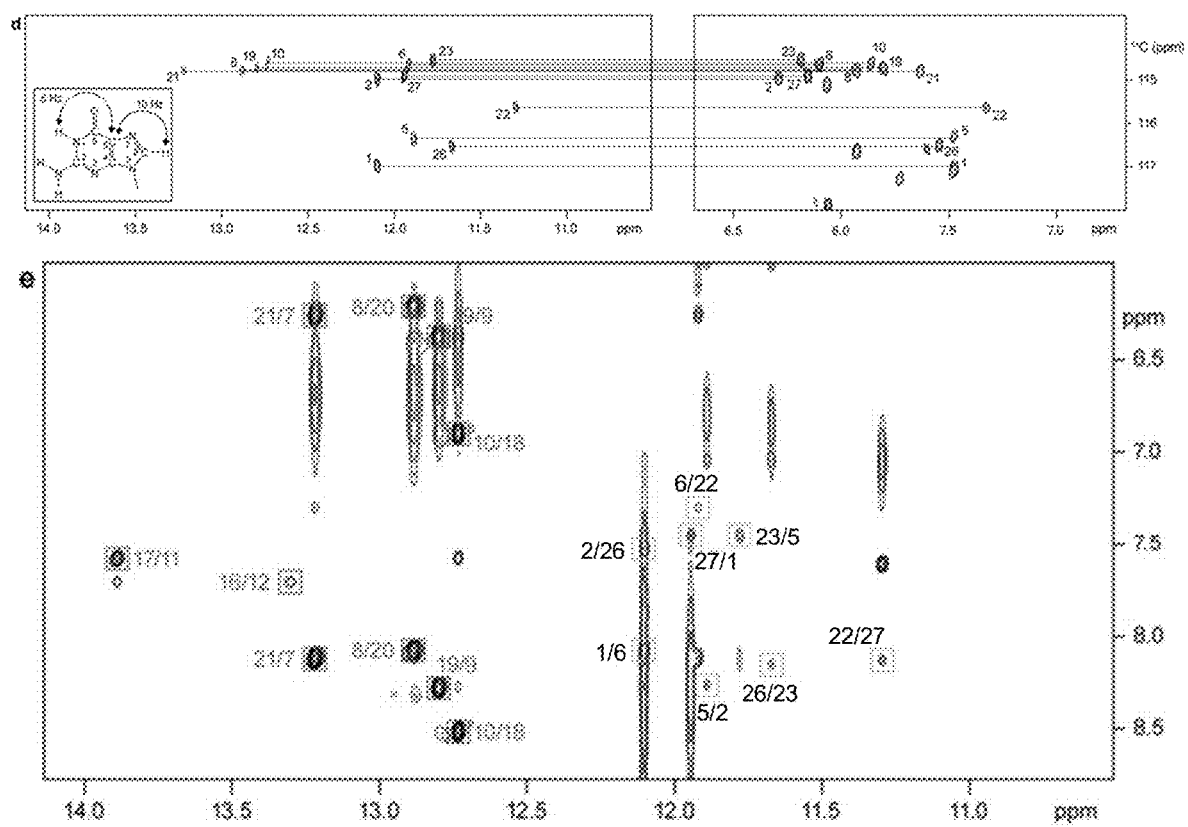
Figure 5:
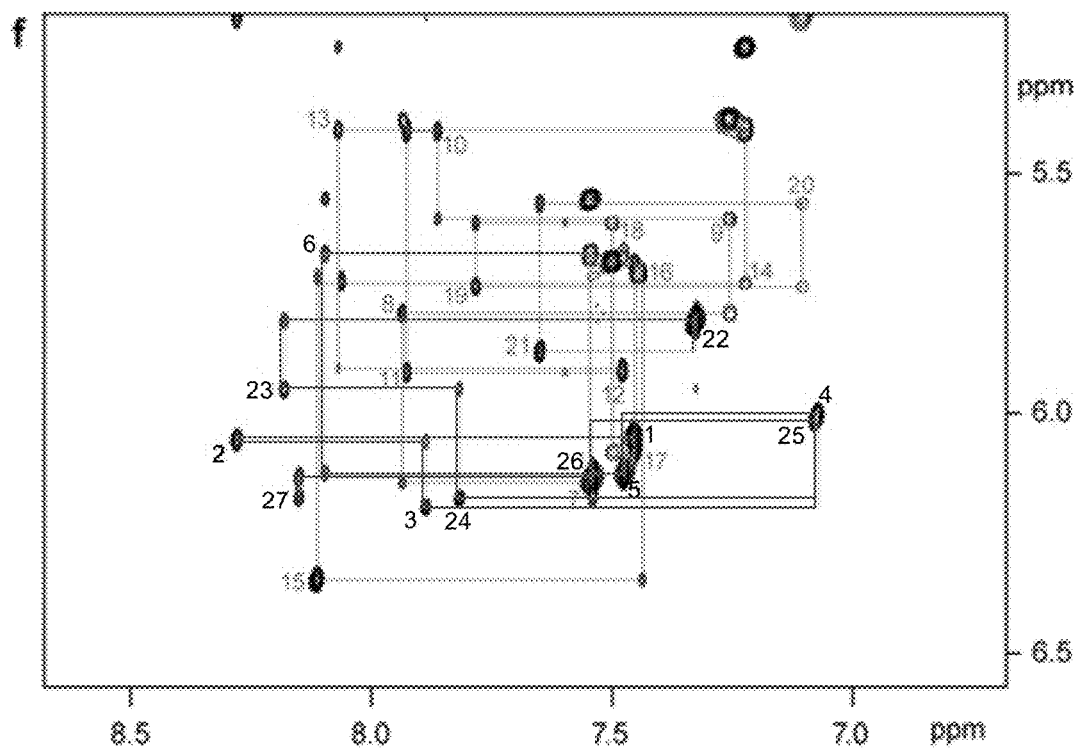
Figure 5:
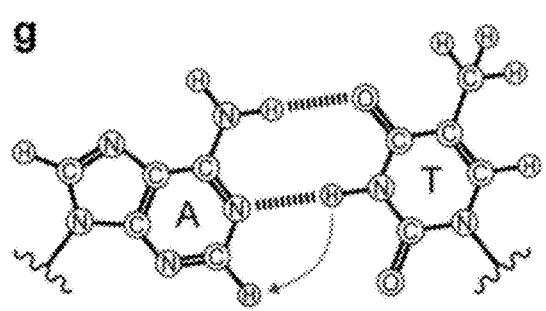
Figure 5:
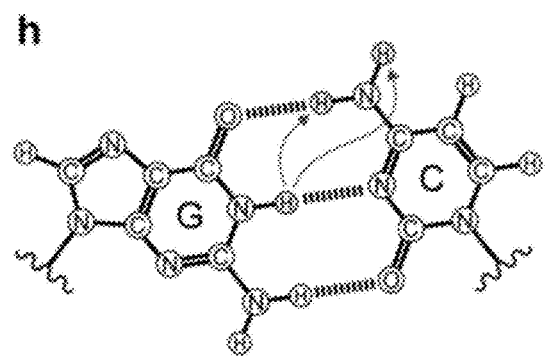
Figure 5:
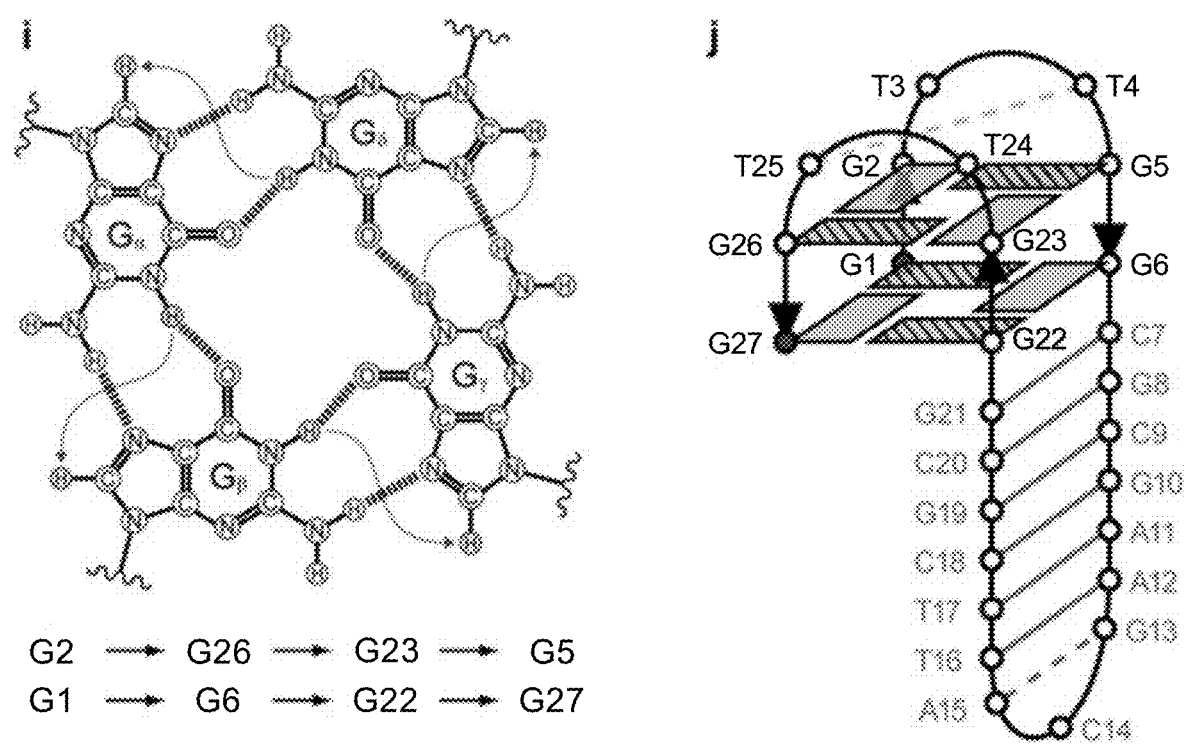
Figure 5:
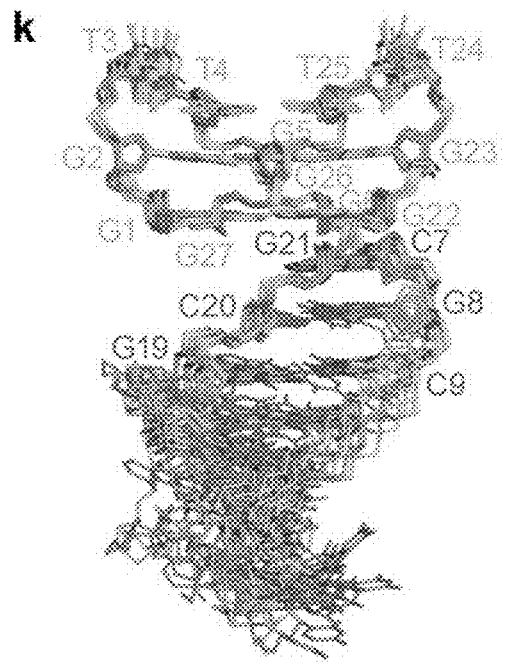
Figure 5:
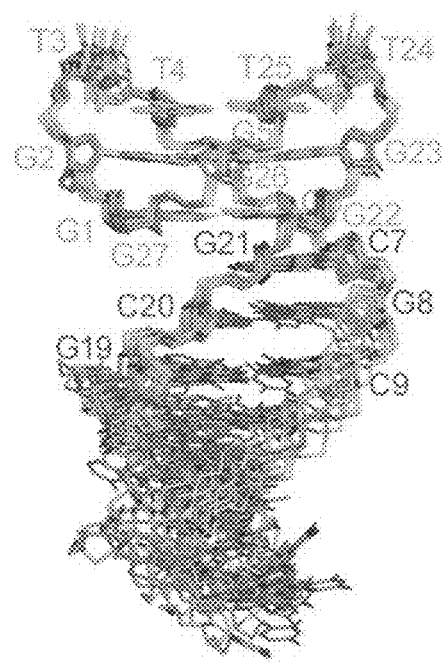
Figure 5:
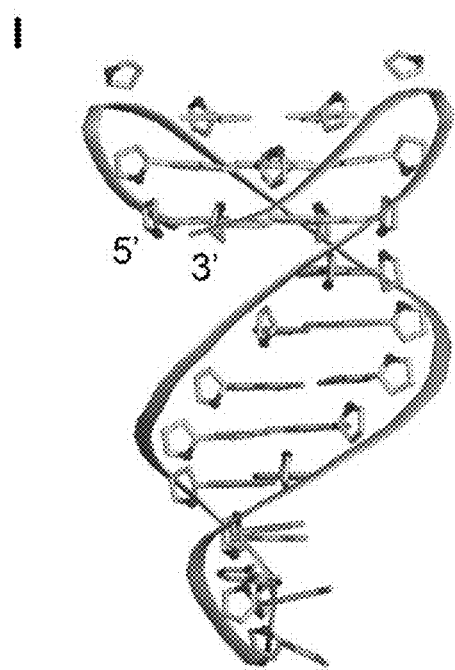
Figure 5:
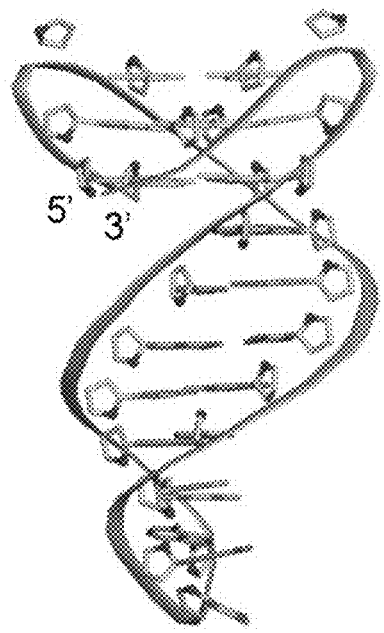
Figure 6:
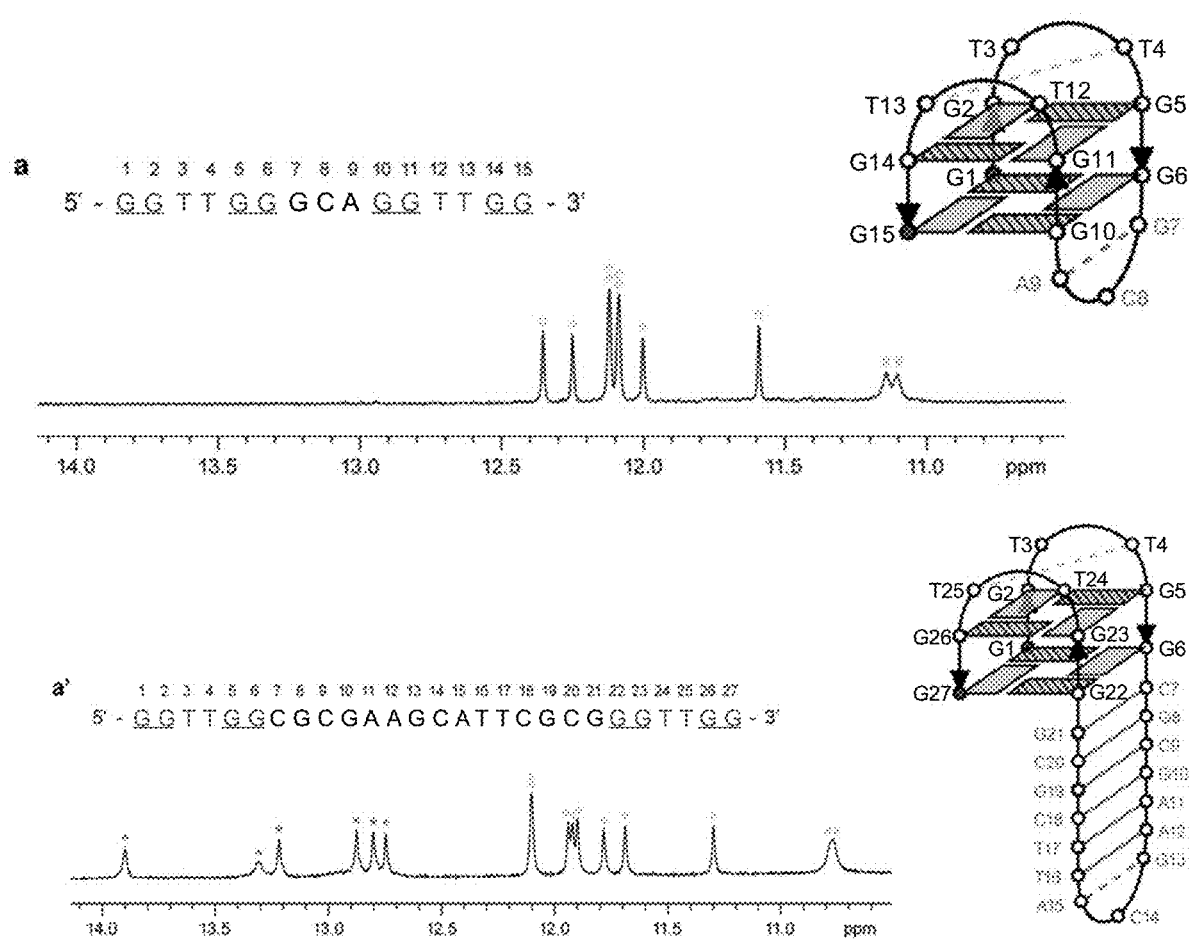
FIG. 6: Compatibility of duplex across the wide groove of G-quadruplexes. a-c, A duplex can be extended continuously from the wide groove of chair (a), basket (b) and (3+1) (c) G-tetrad cores to generate the corresponding quadruplex-duplex constructs (a', b' and c', respectively). In each panel, the sequence and 1D imino proton spectrum of the oligonucleotide are shown together with the schematic diagram for the putative fold adopted by the oligonucleotide. Proton peaks from tetrads are labeled with circles, proton peaks from Watson-Crick base pairs are labeled with asterisks, while proton peaks from non-canonical base pairs are labeled with hash signs. Quadruplex segments are colored in cyan, whereas hairpin segments and 3-nt GCA loops spanning the wide grooves are colored in magenta. The 5'- and 3'-termini are shown as red circles. Non-canonical base pairs are shown as dotted lines.
Figure 6:
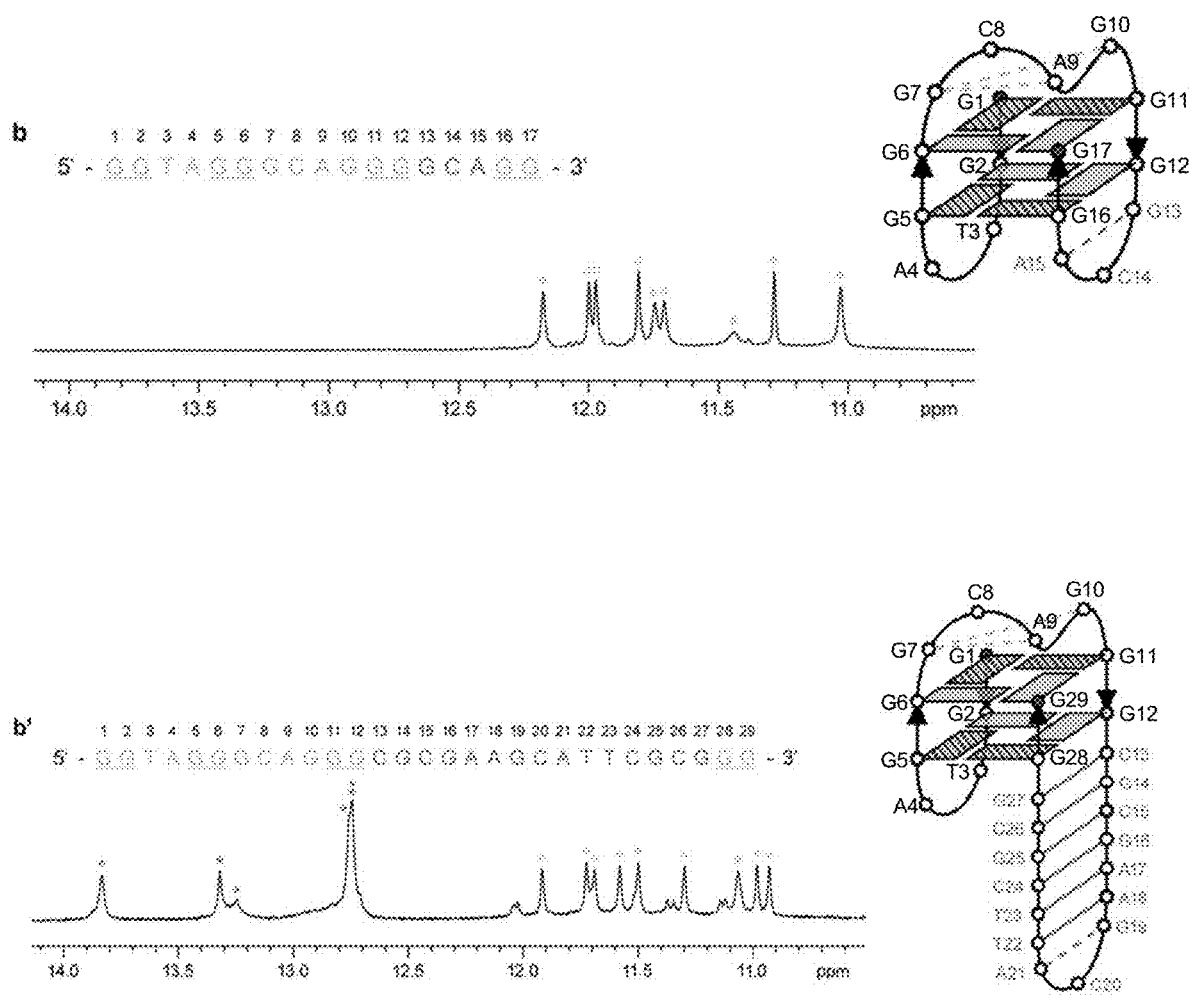
Figure 6:
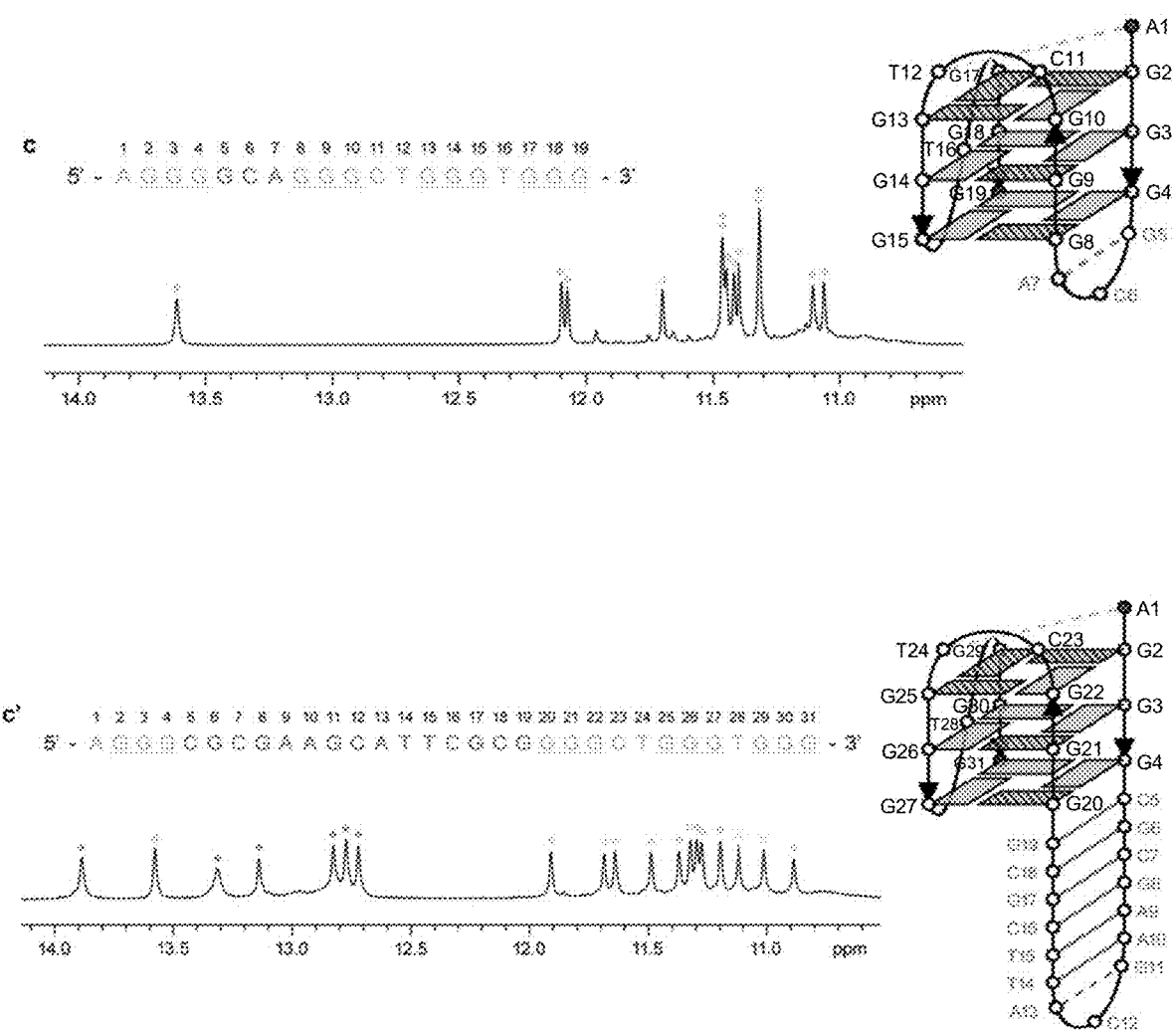

We first demonstrated that a duplex can be extended seamlessly across the wide groove of an antiparallel G-quadruplex (Construct I, "JWC"—junction across wide groove with two, continuous strands; FIG. 4a and FIG. 5). There is a gradual transition between the minor groove of the duplex and the wide groove of the quadruplex (strand separation expanding from ~18 Å to ~19 Å), and this compatibility was shown to apply universally across wide grooves of different G-quadruplexes (FIG. 6). Continual stacking of bases over the duplex and quadruplex segments contributes towards the overall stability of the structure.

Figure 7:
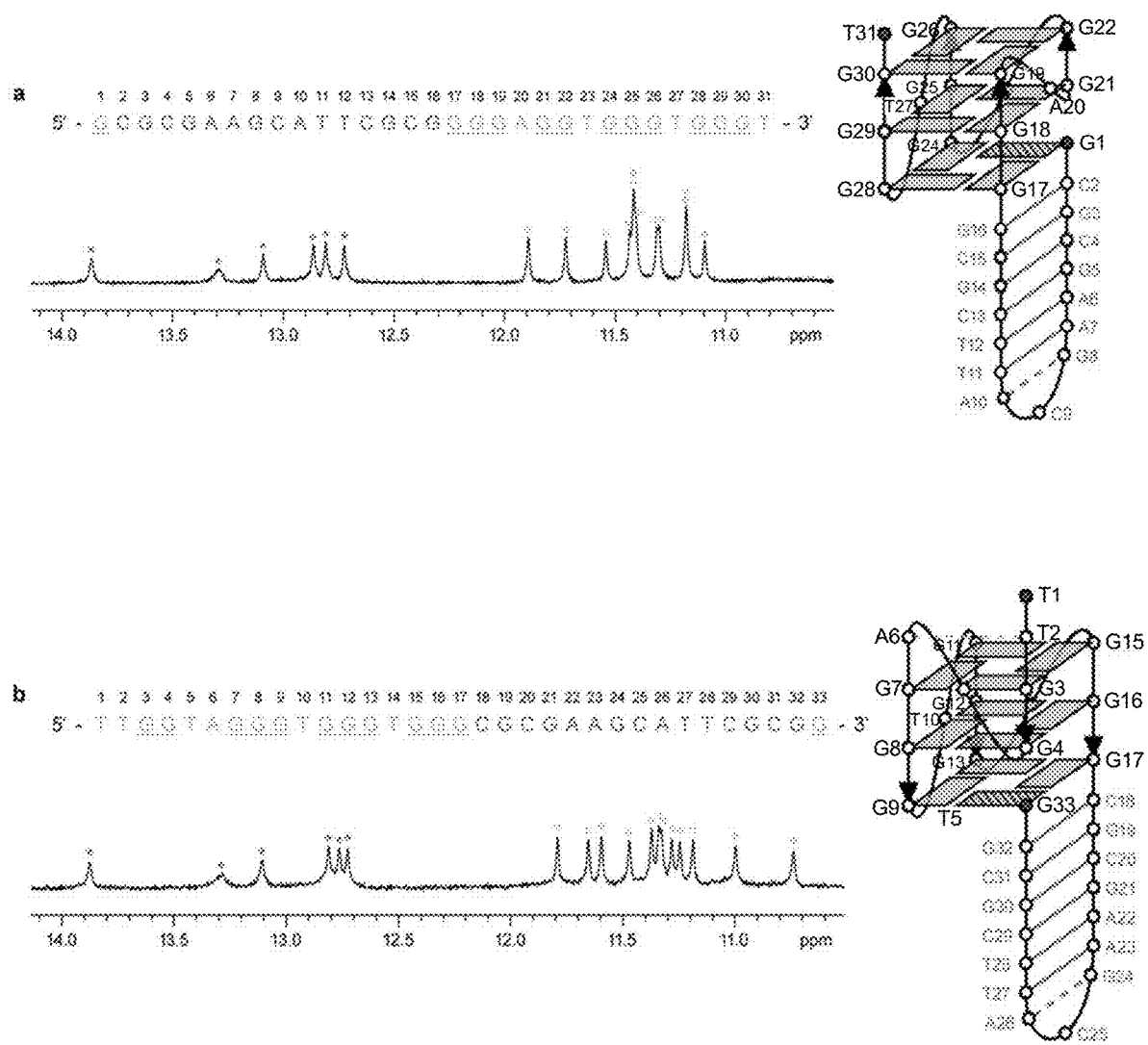
FIG. 7: Introduction of a nick on a G-tract can accommodate the insertion of a loose duplex strand onto the terminal G-tetrad. a,b, The terminal G-tetrad of a quadruplex can serve as a foothold for the 5'-(a) and 3'-(b) termini of a loose duplex strand. In each panel, the sequence and 1D imino proton spectrum of the oligonucleotide are shown together with the schematic diagram for the putative fold adopted by the oligonucleotide. Proton peaks from tetrads are labeled with circles while proton peaks from Watson-Crick base pairs are labeled with asterisks. Quadruplex and hairpin segments are colored in cyan and magenta, respectively. The 5'- and 3'-termini are shown as red circles. Non-canonical base pairs are shown as dotted lines.
Figure 8:
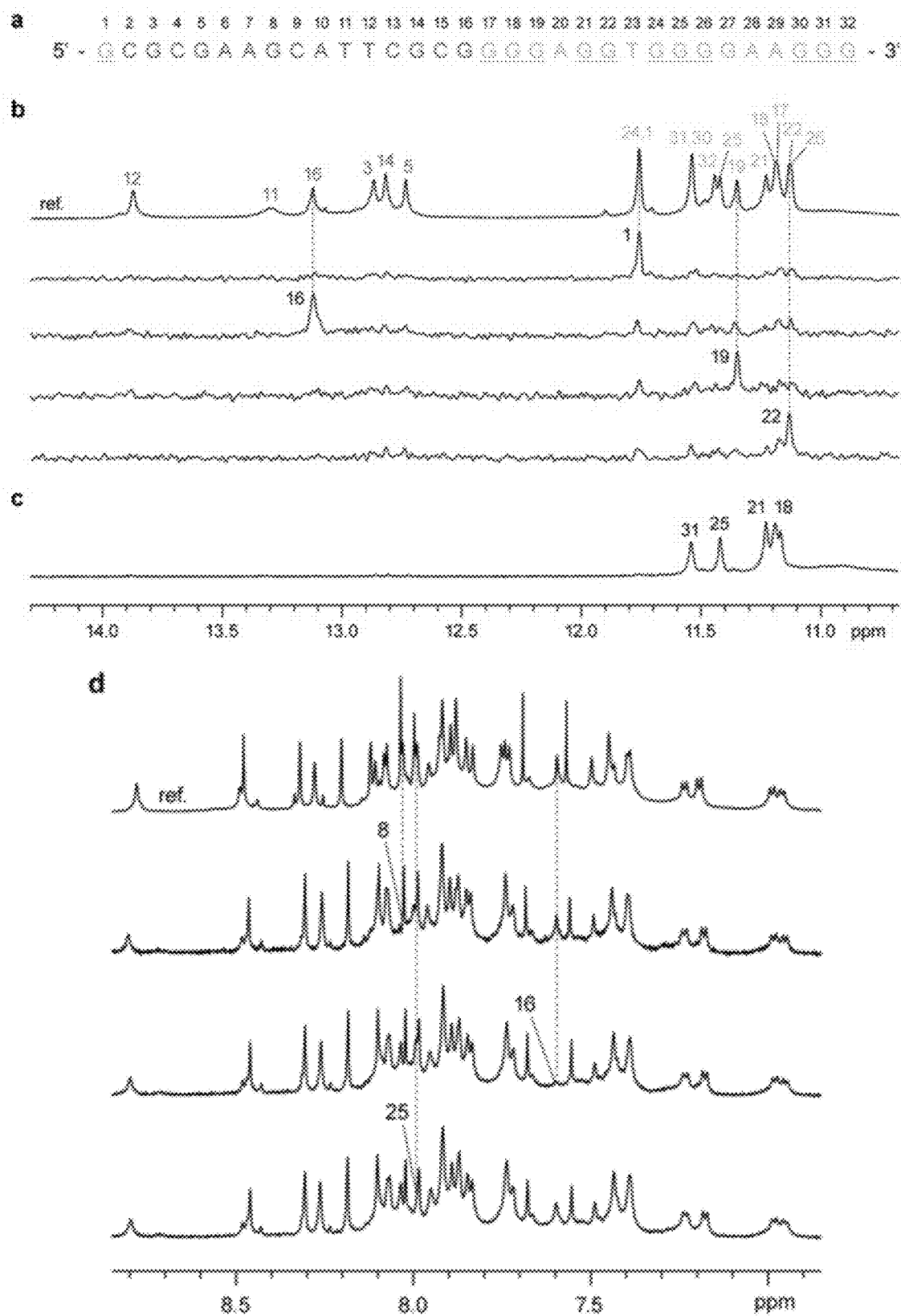
FIG. 8: NMR structural characterization of Construct II. a, Sequence of Construct II. b, Examples of imino proton assignments in $^{15}$N-filtered spectra of samples, 2% $^{15}$N-labeled at the indicated positions. The reference spectrum (ref.) is shown at the top. c, Imino proton spectrum after 2 h in $D_2O$ at 25° C. d, Examples of H8 proton assignments by site-specific $^2$H labeling at the indicated positions. The reference spectrum (ref.) is shown at the top. e, Through-bond correlations between guanine imino and H8 protons via $^{13}$C5 at natural abundance, using long-range J-couplings shown in the inset. Assignments are labeled with residue numbers. Different threshold levels are displayed for the left and right panes. f, NOESY spectrum (mixing time, 200 ms) showing the cross-peaks that identify the arrangement of the three G-tetrads and the Watson-Crick base pairs. Cross-peaks arising from imino-H8 connectivity around the three G-tetrads are framed in cyan and labeled with the residue number of imino proton in the first position and that of H8 proton in the second position. Cross-peaks between thymine imino proton and adenine H2 proton, and between guanine imino proton and cytosine amino protons, are framed in magenta and labeled with the residue number of thymine/guanine in the first position and that of adenine/cytosine in the second position. Weak peaks are marked with asterisks. g, NOESY spectrum (mixing time, 300 ms) showing the H8/H6-H1' connectivity of Construct II. Intraresidue H8/H6-H1' NOE cross-peaks are labeled with residue numbers. h, NOEs from thymine imino proton to adenine H2 proton that establish the A6•T12 and A7•T11 base pairs. i, NOEs from guanine imino proton to cytosine amino protons that establish the G16•C2, G3•C15, G14•C4 and G5•C13 base pairs. j, Characteristic guanine imino-H8 NOE connectivity patterns around a $G_\alpha$•$G_\beta$•$G_\gamma$•$G_\delta$ tetrad as indicated with arrows, with the connectivities observed for the G19•G22•G26•G32, G18•G21•G25•G31 and G17•G1•G24•G30 tetrads shown below. k, Schematic diagram of Construct II. Quadruplex and hairpin segments are colored in cyan and magenta, respectively. The 5'- and 3'-termini are shown as red circles. Non-canonical base pairs are shown as dotted lines. l,m, Stereo views of ten superimposed refined structures (l) and a representative structure in ribbon representation (m). Structures are aligned based on the tetrad core.
Figure 8:
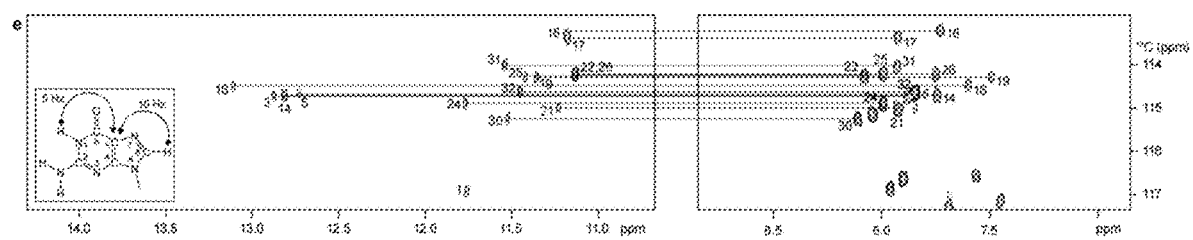
Figure 8:
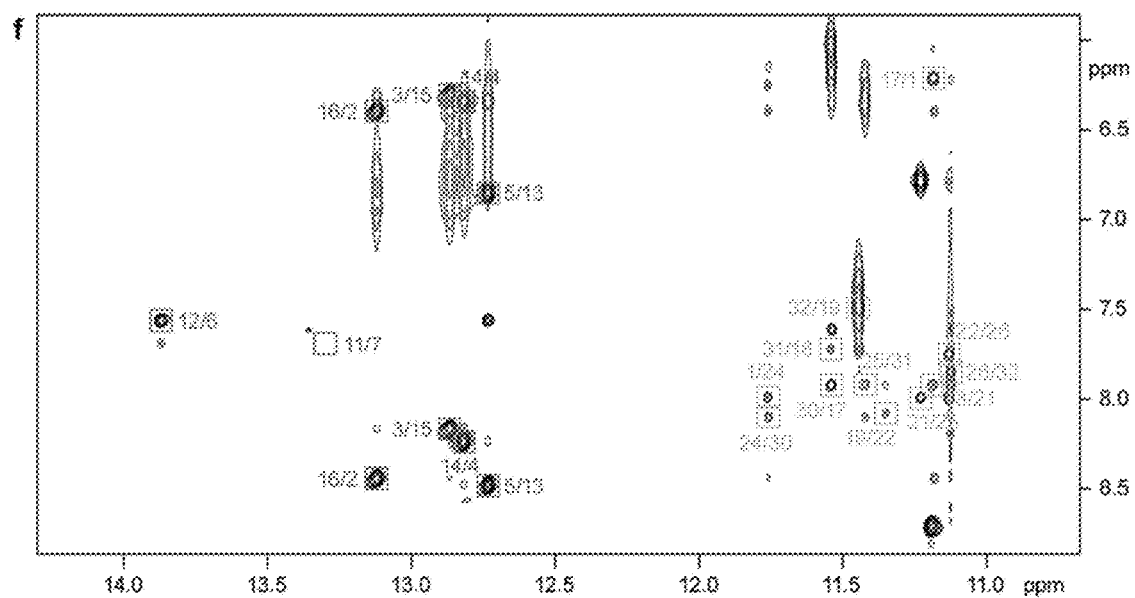
Figure 8:
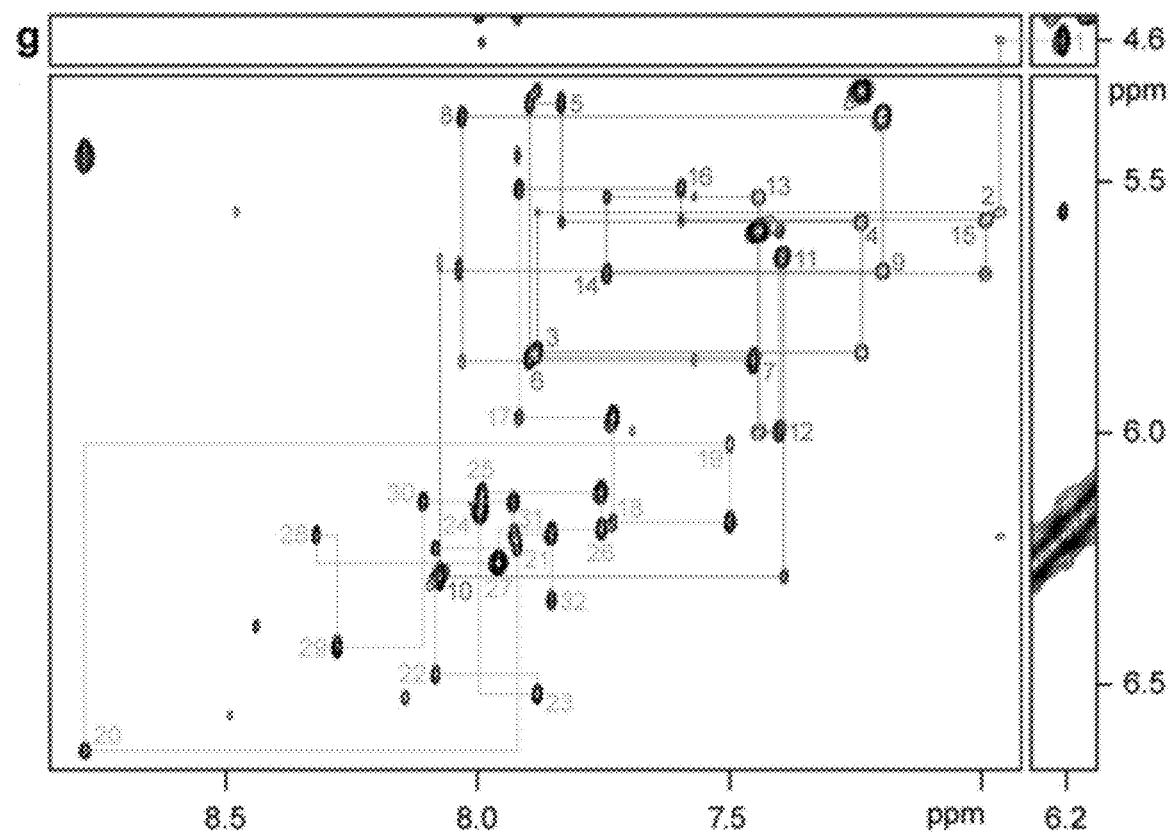
Figure 8:
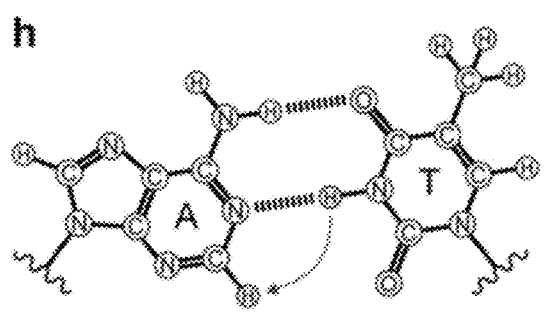
Figure 8:
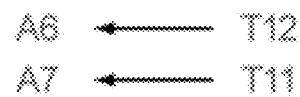
Figure 8:
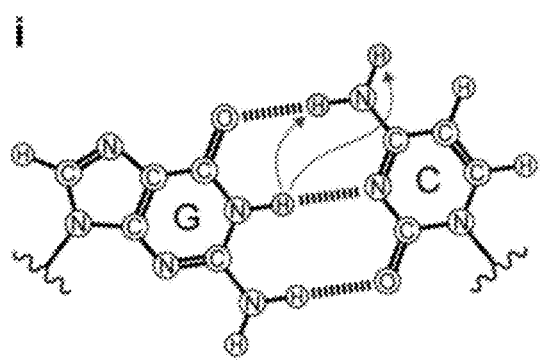
Figure 8:
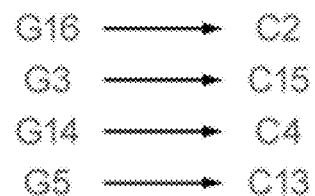
Figure 8:
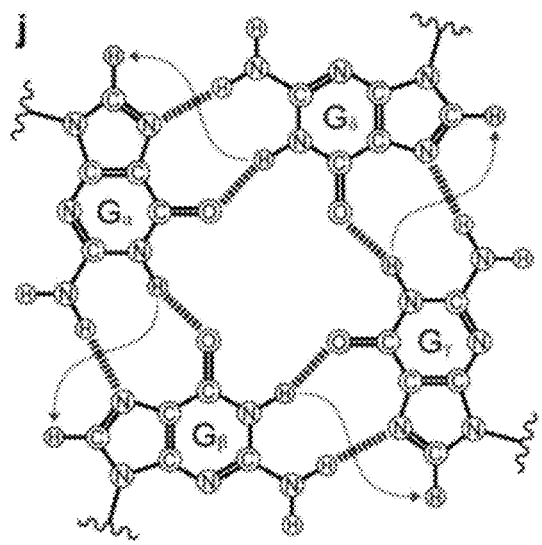
Figure 8:
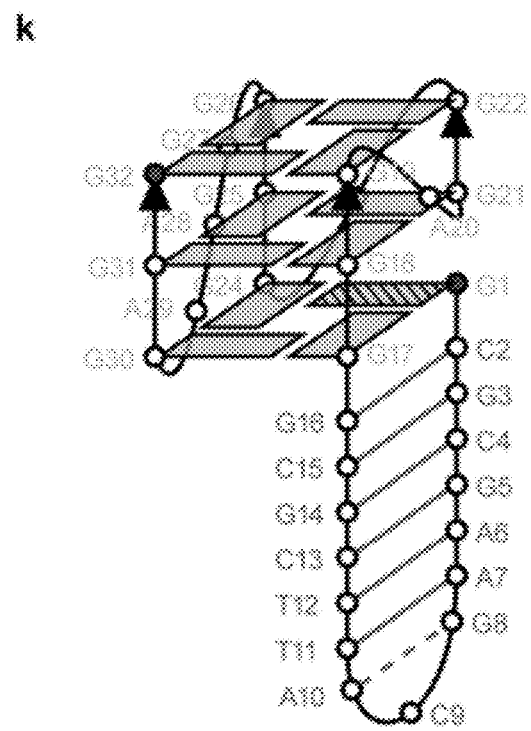
Figure 8:
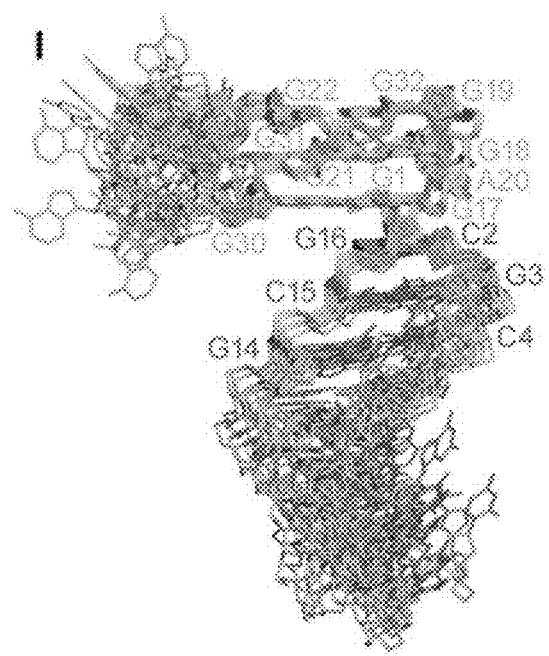
Figure 8:
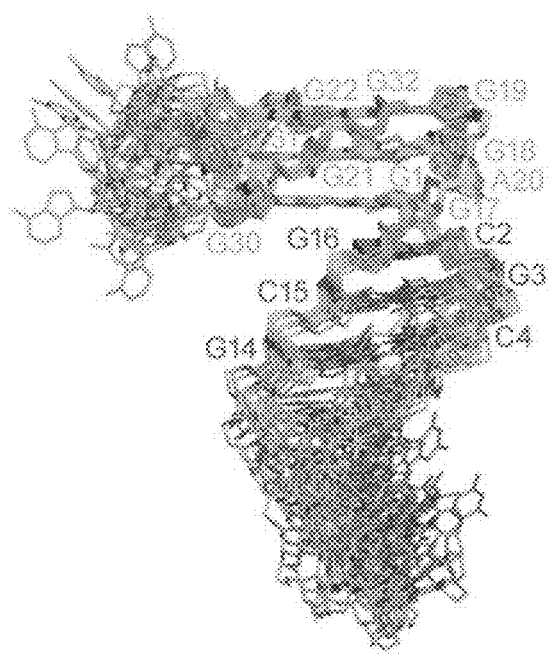
Figure 8:
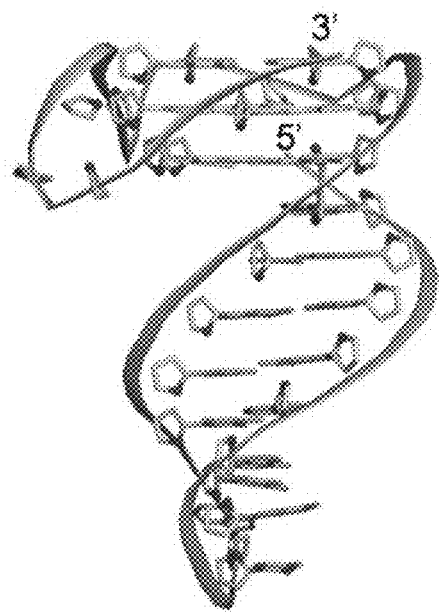
Figure 8:
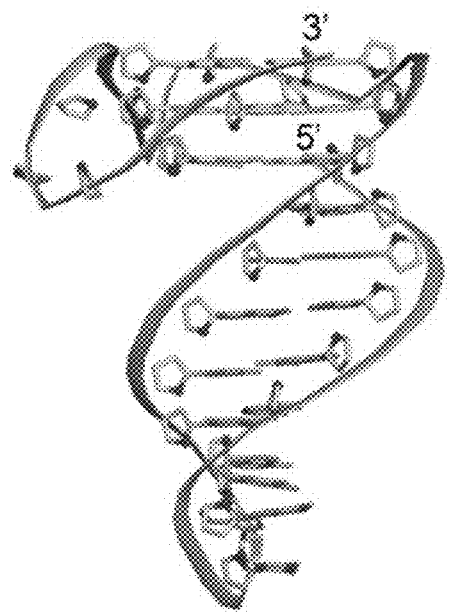

A nick can be introduced within the G-tract bordering the quadruplex-duplex junction such that the terminal G-tetrad now serves as a foothold for the loose strand, which could be anchored at the 5'- or 3'-end (FIG. 7). The resulting strand discontinuity permits the local accommodation of a wide groove across the medium groove edge of a quadruplex (Construct II, "$JW_MD$"—junction across medium-made-wide groove with a discontinuous strand; FIG. 4b and FIG. 8), effectively widening the strand separation from ~16 Å to ~18-19 Å at the anchor point. This approach removes the need to maintain the strict antiparallel strand orientation of the two G-columns mediating the duplex.

Figure 9:
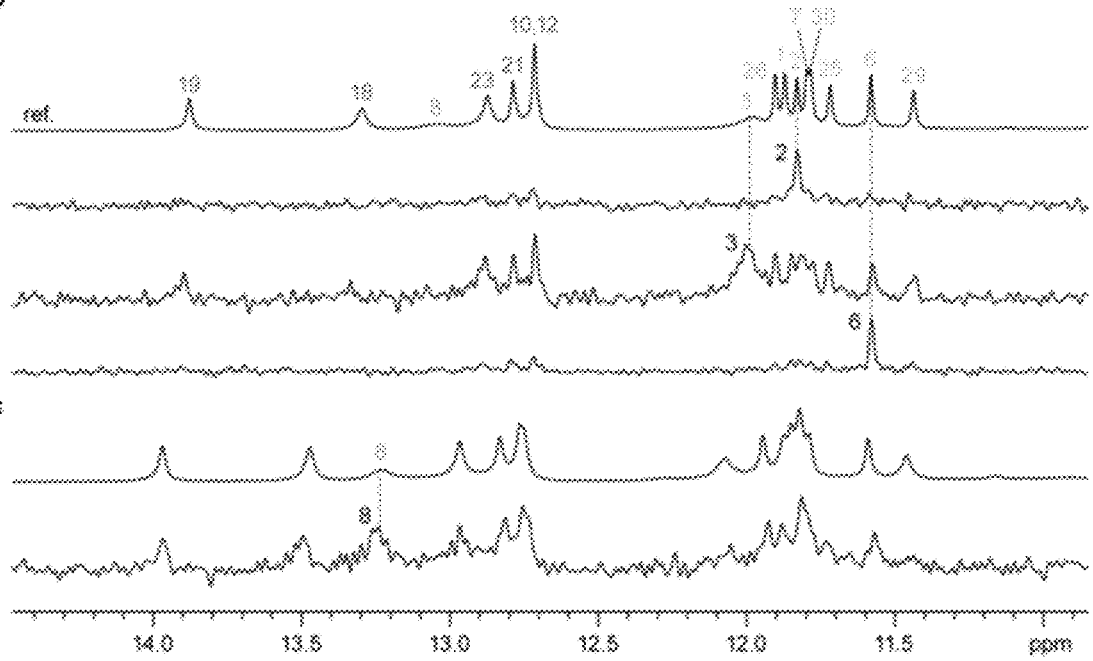
FIG. 9: NMR structural characterization of Construct III. a, Sequence of Construct III. b,c, Examples of imino proton assignments in $^{15}$N-filtered spectra of samples, 2% $^{15}$N-labeled at the indicated positions, at 25° C. (b) and 5° C. (c). The reference spectra (ref.) are shown at the top. d, Examples of H8 proton assignments by site-specific $^2$H labeling at the indicated positions. The reference spectrum (ref.) is shown at the top. Note the presence of peaks from minor compounds. e, Through-bond correlations between guanine imino and H8 protons via $^{13}$C5 at natural abundance, using long-range J-couplings shown in the inset. Assignments are labeled with residue numbers. Different threshold levels are displayed for the left and right panes. f, NOESY spectrum (mixing time, 200 ms) showing the cross-peaks that identify the arrangement of the two G-tetrads and the Watson-Crick base pairs. Cross-peaks arising from imino-H8 connectivity around the two G-tetrads are framed in cyan and labeled with the residue number of imino proton in the first position and that of H8 proton in the second position. Cross-peaks between thymine imino proton and adenine H2 proton, and between guanine imino proton and cytosine amino protons, are framed in magenta and labeled with the residue number of thymine/guanine in the first position and that of adenine/cytosine in the second position. g, NOESY spectrum (mixing time, 300 ms) showing the H8/H6-H1' connectivity of Construct III. Intraresidue H8/H6-H1' NOE cross-peaks are labeled with residue numbers. h, NOEs from thymine imino proton to adenine H2 proton that establish the A13•T19 and A14•T18 base pairs. i, NOEs from guanine imino proton to cytosine amino protons that establish the G23•C9, G10•C22, G21•C11 and G12•C20 base pairs. j, Characteristic guanine imino-H8 NOE connectivity patterns around a $G_\alpha$•$G_\beta$•$G_\gamma$•$G_\delta$ tetrad as indicated with arrows, with the connectivities observed for the G2•G6•G29•G26 and G1•G25•G30•G7 tetrads shown below. k, Schematic diagram of Construct III. Quadruplex and hairpin segments are colored in cyan and magenta, respectively. The 5'- and 3'-termini are shown as red circles. Non-canonical base pairs are shown as dotted lines. l,m, Stereo views of ten superimposed refined structures (l) and a representative structure in ribbon representation (m). Structures are aligned based on the tetrad core.
Figure 9:
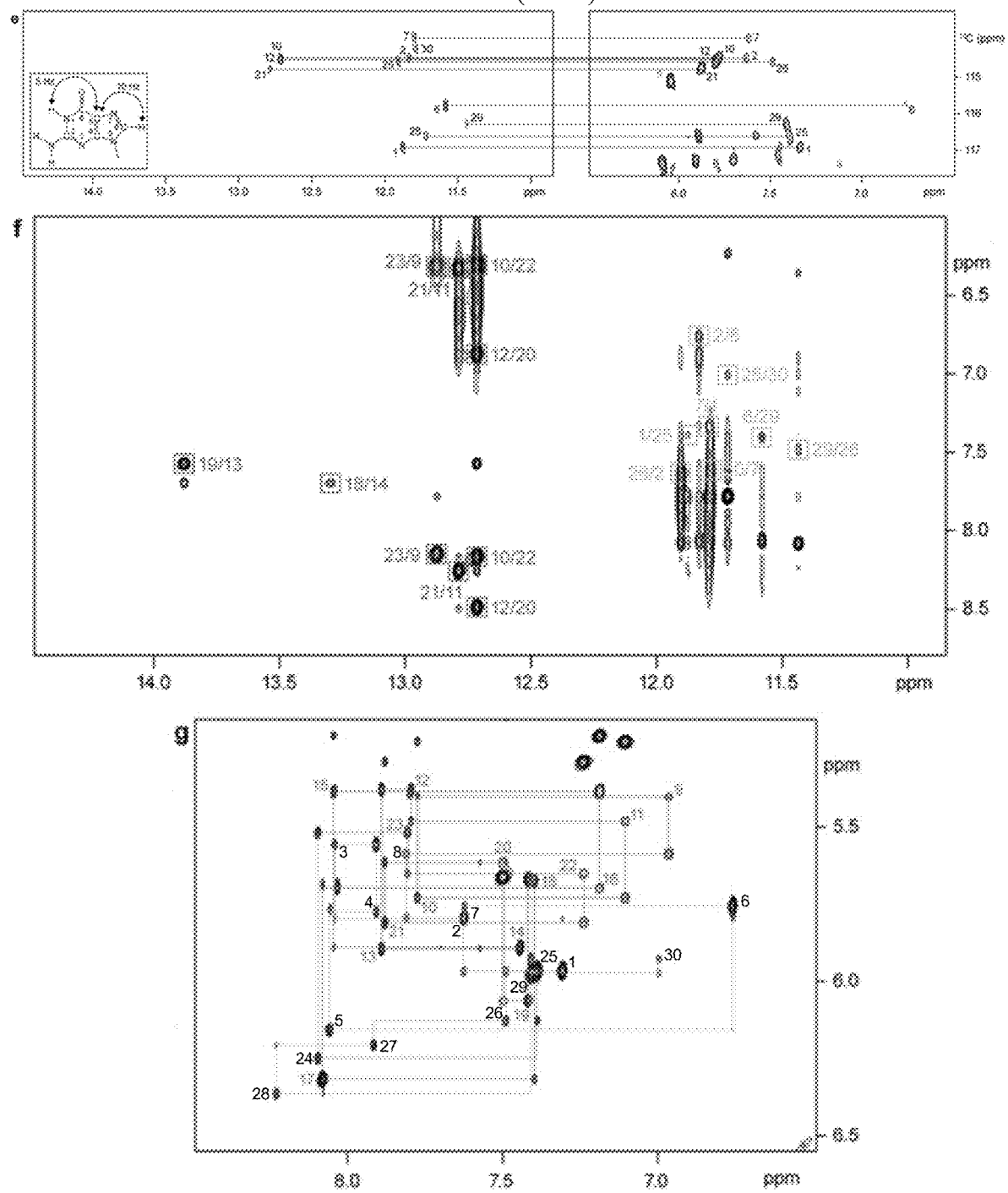
Figure 9:
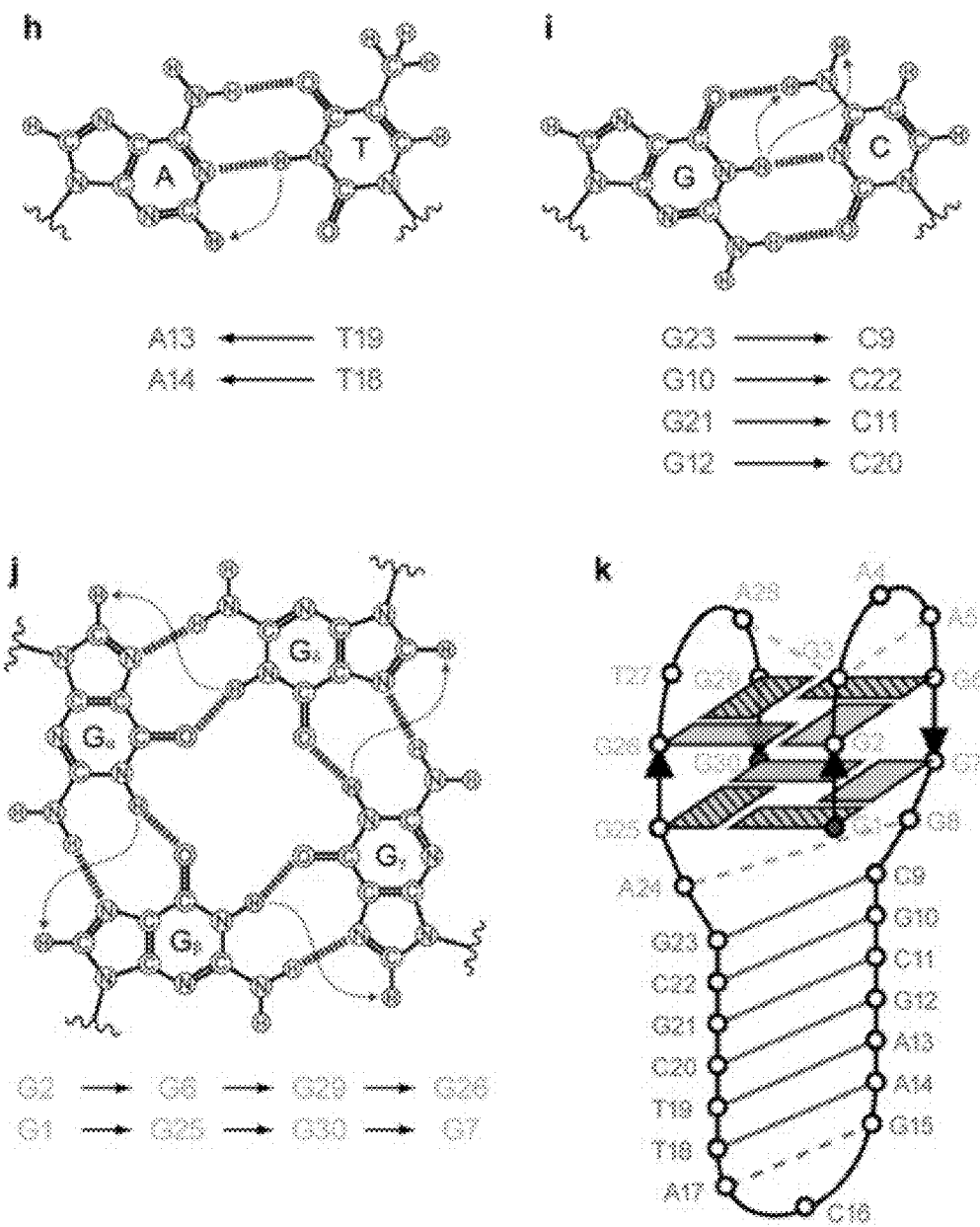
Figure 9:
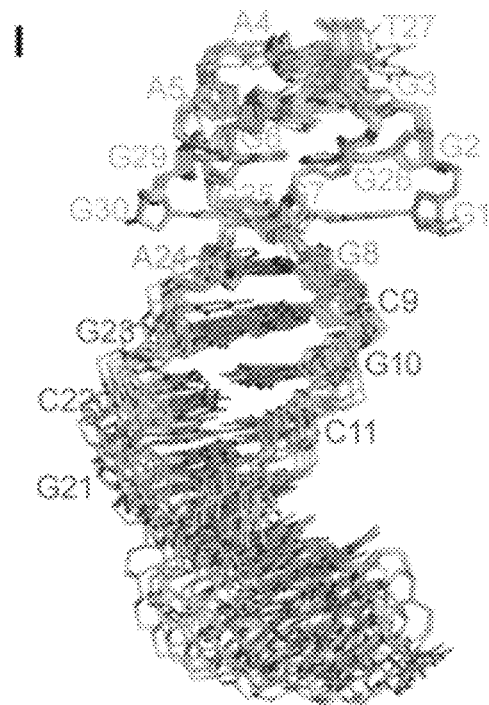
Figure 9:
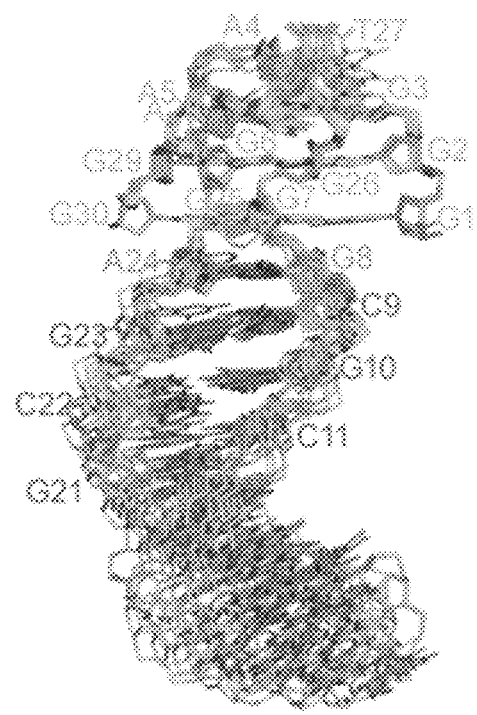
Figure 9:
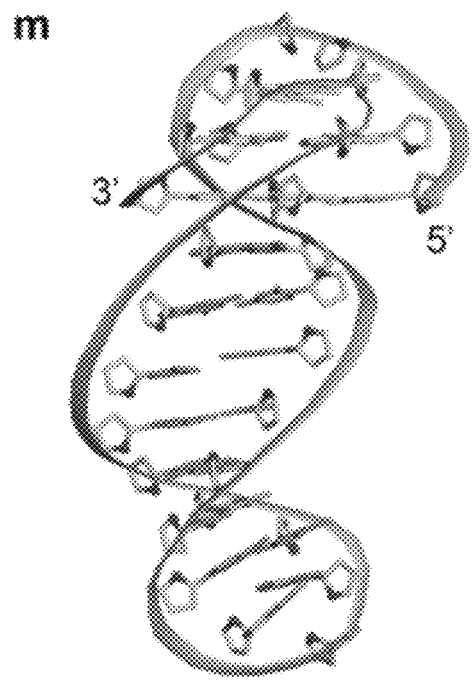
Figure 9:
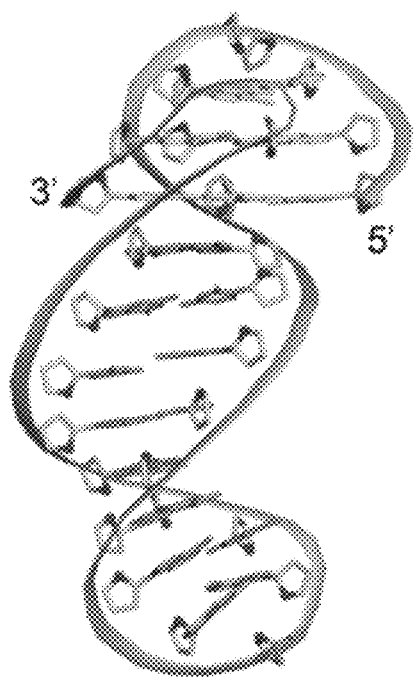

To connect a duplex across the diagonal corners of a tetrad (the phosphate groups would have to span a distance of >20 Å), an adaptor G•A Watson-Crick mismatch base pair could be placed at the junction to ease the transition between the two segments with different dimensions (Construct III, "JDC"—junction across diagonal corners with two continuous strands; FIG. 4c and FIG. 9). There is an associated displacement of the helical axis of the duplex with respect to that of the quadruplex.

Figure 10:
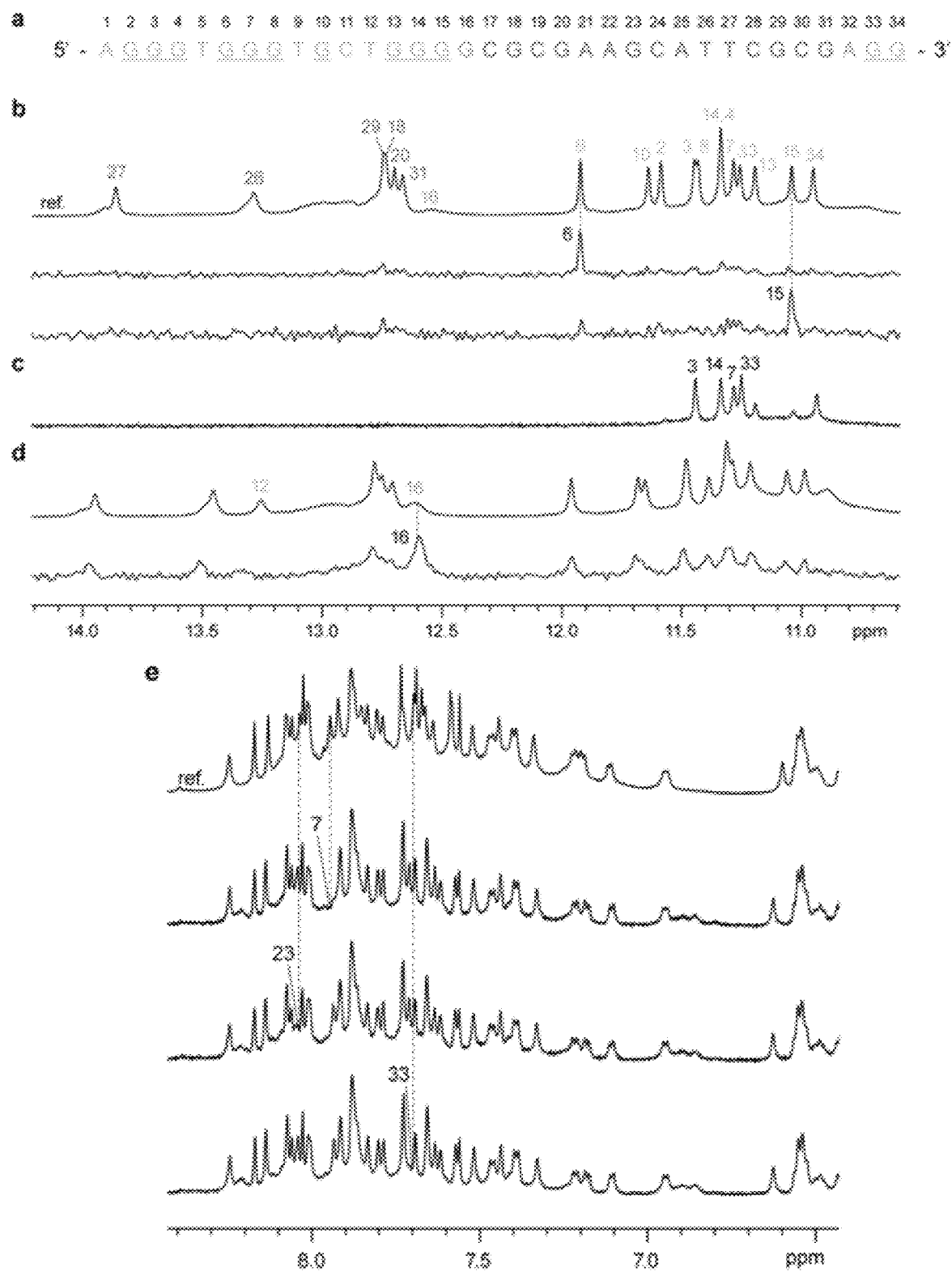
FIG. 10: NMR structural characterization of Construct IV. a, Sequence of Construct IV. b, Examples of imino proton assignments in $^{15}$N-filtered spectra of samples, 2% $^{15}$N-labeled at the indicated positions. The reference spectrum (ref.) is shown at the top. c, Imino proton spectrum after 2 h in D$_2$O at 25° C. d, Imino proton assignment of G16 in $^{15}$N-filtered spectrum of sample, 2% $^{15}$N-labeled at G16, at 5° C. The reference spectrum (ref.) is shown at the top. e, Examples of H8 proton assignments by site-specific $^2$H labeling at the indicated positions. The reference spectrum (ref.) is shown at the top. f, Through-bond correlations between guanine imino and H8 protons via $^{13}$C5 at natural abundance, using long-range J-couplings shown in the inset. Assignments are labeled with residue numbers. Different threshold levels are displayed for the left and right panes. g, NOESY spectrum (mixing time, 200 ms) showing the cross-peaks that identify the arrangement of the three G-tetrads and the Watson-Crick base pairs. Cross-peaks arising from imino-H8 connectivity around the three G-tetrads are framed in cyan and labeled with the residue number of imino proton in the first position and that of H8 proton in the second position. Cross-peaks between thymine imino proton and adenine H2 proton, and between guanine imino proton and cytosine amino protons, are framed in magenta and labeled with the residue number of thymine/guanine in the first position and that of adenine/cytosine in the second position. h, NOESY spectrum (mixing time, 300 ms) showing the H8/H6-H1' connectivity of Construct IV. Intraresidue H8/H6-H1' NOE cross-peaks are labeled with residue numbers. i, NOEs from thymine imino proton to adenine H2 proton that establish the A21•T27 and A22•T26 base pairs. j, NOEs from guanine imino proton to cytosine amino protons that establish the G31•C17, G18•C30, G29•C19 and G20•C28 base pairs. k, Characteristic guanine imino-H8 NOE connectivity patterns around a $G_\alpha$•$G_\beta$•$G_\gamma$•$G_\delta$ tetrad as indicated with arrows, with the connectivities observed for the G2•G6•G10•G13, G3•G7•G33•G14 and G4•G8•G34•G15 tetrads shown below. l, Schematic diagram of Construct IV. Quadruplex and hairpin segments are colored in cyan and magenta, respectively. The 5'- and 3'-termini are shown as red circles. Non-canonical base pairs are shown as dotted lines. m,n, Stereo views of ten superimposed refined structures (m) and a representative structure in ribbon representation (n). Structures are aligned based on the tetrad core.
Figure 10:
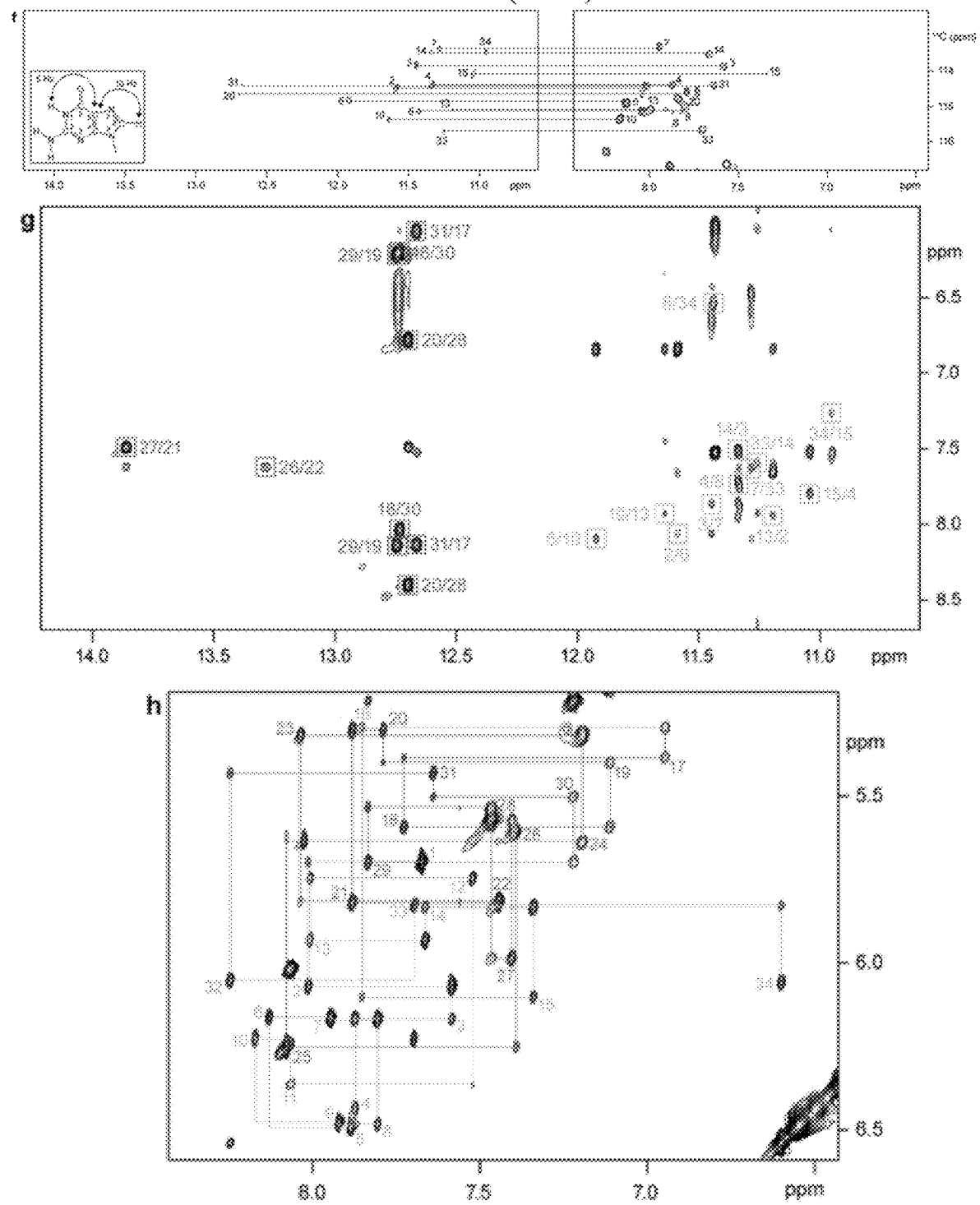
Figure 10:
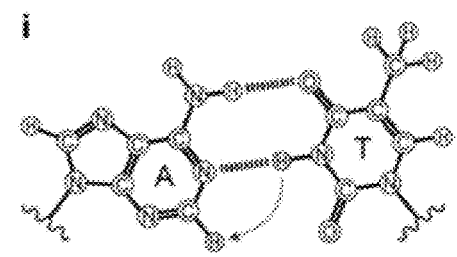
Figure 10:
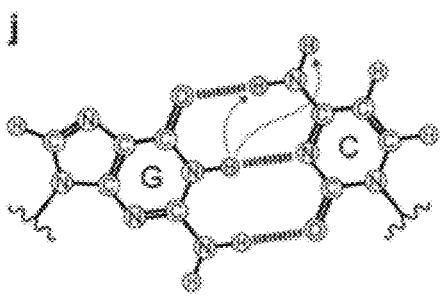
Figure 10:
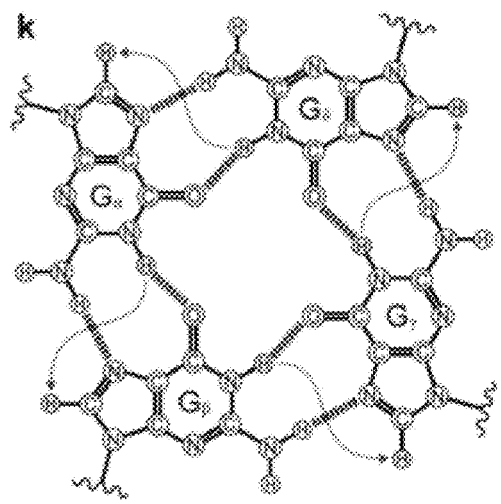
Figure 10:
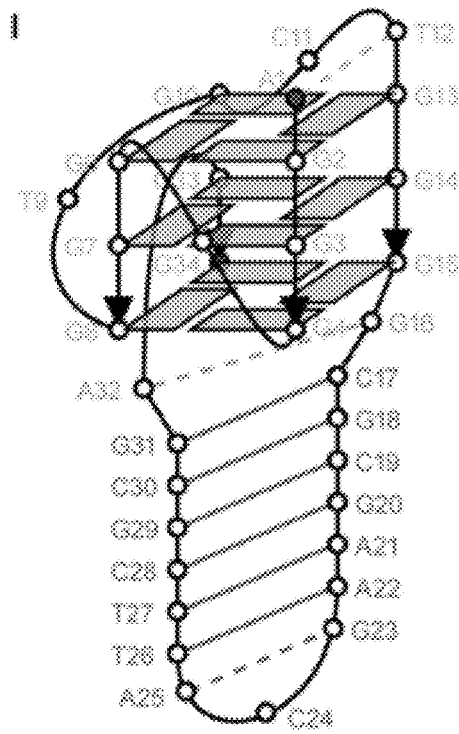
Figure 10:
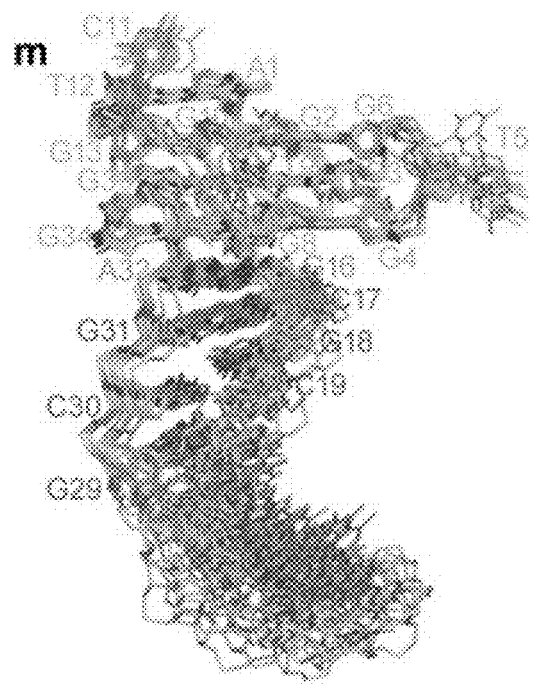
Figure 10:
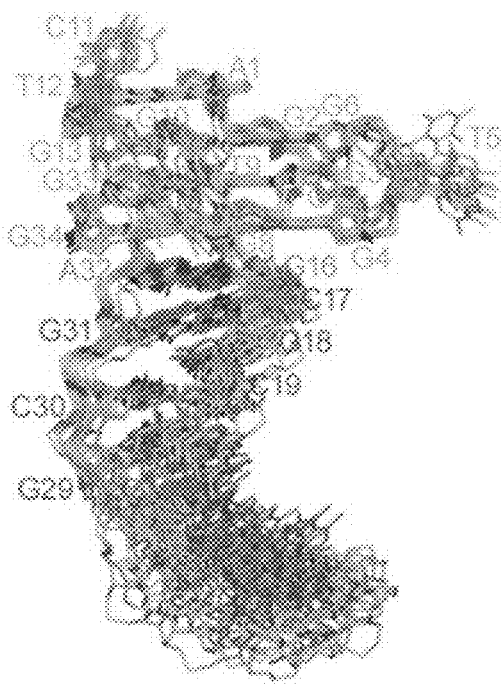
Figure 10:
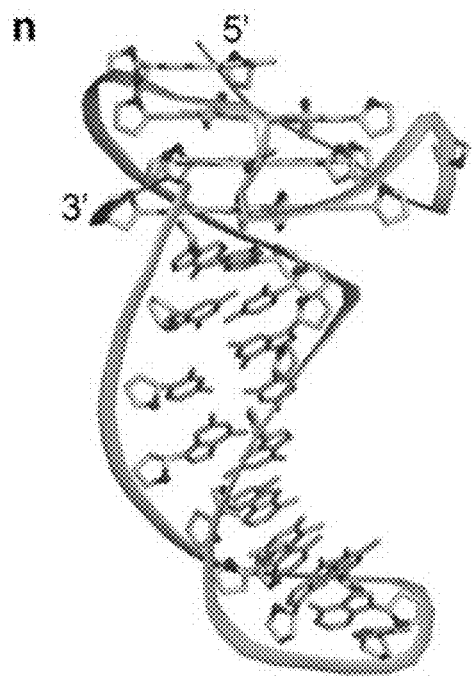
Figure 10:
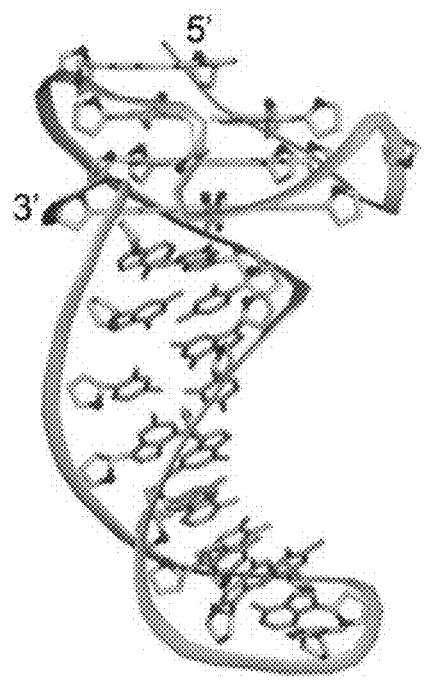

In contrast to the wide groove, continual stacking of a duplex over the narrow groove of a. quadruplex would not be favorable; the two strands would have to shrink from ~18 Å apart to ~12 Å at a single step. Instead, a snapback approach, previously observed in a promoter G-quadruplex and an RNA duplex-quadruplex junction, could be adapted to bridge a duplex across this edge of the tetrad core (Construct IV, "$JD_NS$"—junction across narrow groove-made-diagonal corners via a snapback; FIG. 4d and FIG. 10).

Figure 11:
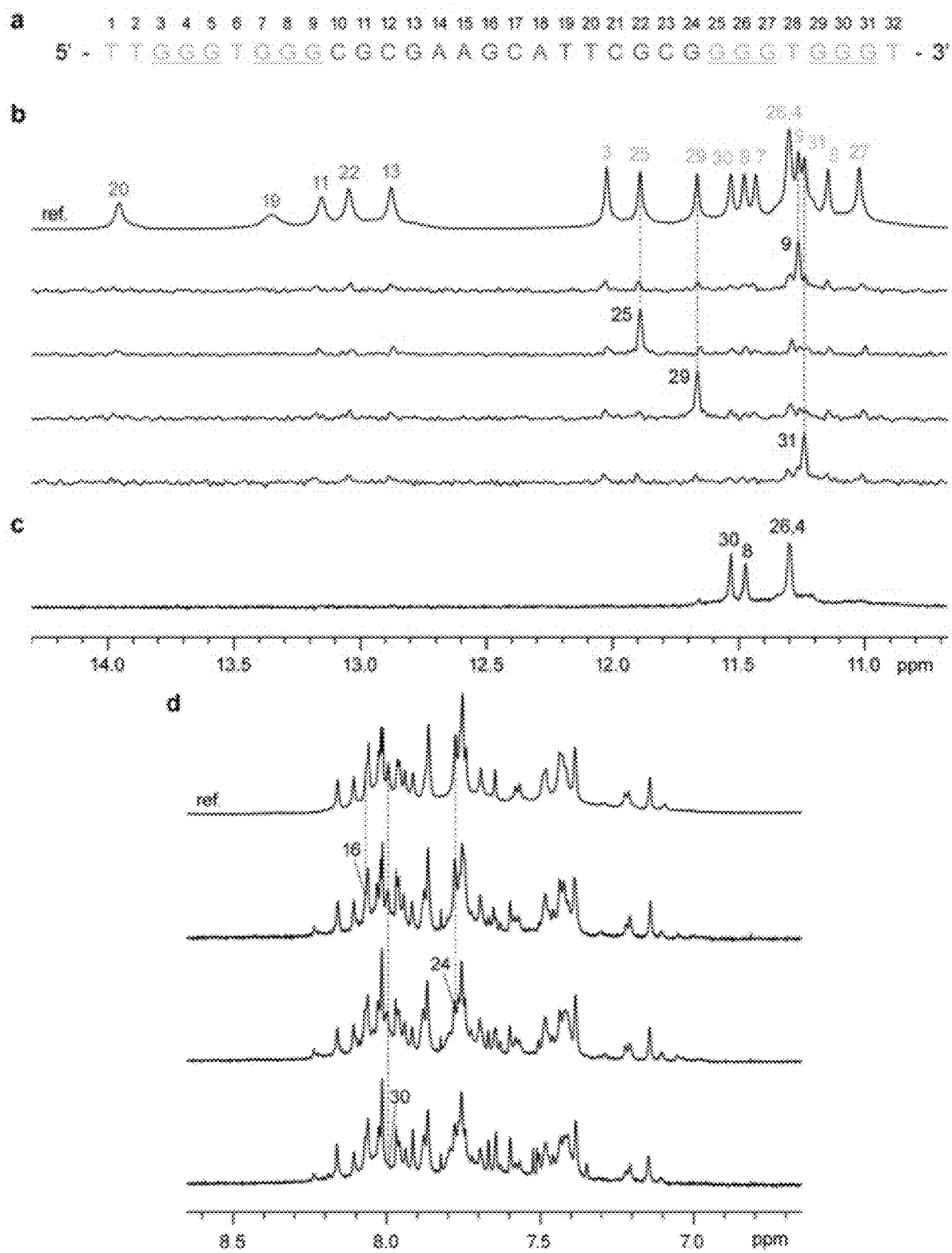
FIG. 11: NMR structural characterization of Construct V. a, Sequence of Construct V. b, Examples of imino proton assignments in $^{15}$N-filtered spectra of samples, 2% $^{15}$N-labeled at the indicated positions. The reference spectrum (ref.) is shown at the top. c, Imino proton spectrum after 2 h in D$_2$O at 25° C. d, Examples of H8 proton assignments by site-specific $^2$H labeling at the indicated positions. The reference spectrum (ref.) is shown at the top. Note the presence of peaks from minor compounds. e, Through-bond correlations between guanine imino and H8 protons via $^{13}$C5 at natural abundance, using long-range J-couplings shown in the inset. Assignments are labeled, with residue numbers. Different threshold levels are displayed for the left and right panes. f, NOESY spectrum (mixing time, 200 ms) showing the cross-peaks that identify the arrangement of the three G-tetrads and the Watson-Crick base pairs. Cross-peaks arising from imino-H8 connectivity around the three G-tetrads are framed in cyan and labeled with the residue number of imino proton in the first position and that of H8 proton in the second position. Cross-peaks between thymine imino proton and adenine H2 proton, and between guanine imino proton and cytosine amino protons, are framed in magenta and labeled with the residue number of thymine/guanine in the first position and that of adenine/cytosine in the second position. Weak peaks are marked with asterisks. g, NOESY spectrum (mixing time, 300 ms) showing the H8/H6-H1' connectivity of Construct V. Intraresidue H8/H6-H1' NOE cross-peaks are labeled with residue numbers. h, NOEs from thymine imino proton to adenine H2 proton that establish the A14•T20 and A15•T19 base pairs. i, NOEs from guanine imino proton to cytosine amino protons that establish the G11•C23, G22•C12 and G13•C21 base pairs. j, Characteristic guanine imino-H8 NOE connectivity patterns around a $G_\alpha$•$G_\beta$•$G_\gamma$•$G_\delta$ tetrad as indicated with arrows, with the connectivities observed for the G3•G7•G25•G29, G4•G8•G26•G30 and G5•G9•G27•G31 tetrads shown below. k, Schematic diagram of Construct V. Quadruplex and hairpin segments are colored in cyan and magenta, respectively. The 5'- and 3'-termini are shown as red circles. Non-canonical base pairs are shown as dotted lines. l,m, Stereo views of ten superimposed refined structures (l) and a representative structure in ribbon representation (m). Structures are aligned based on the tetrad core.
Figure 11:
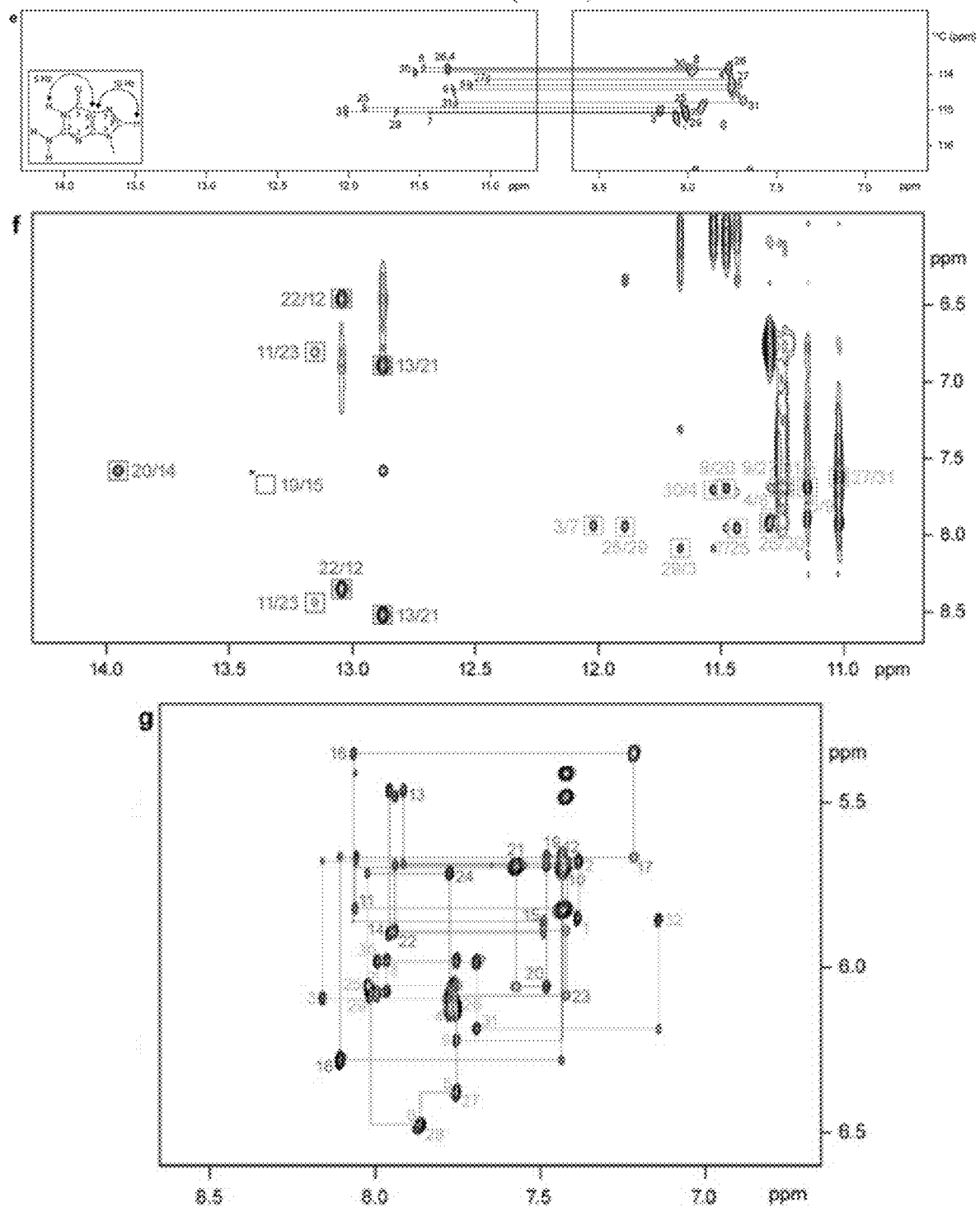
Figure 11:
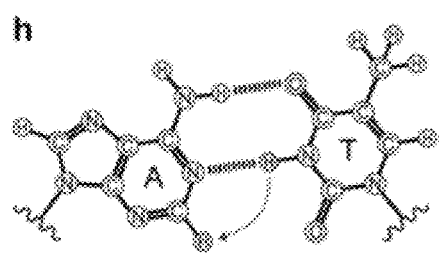
Figure 11:
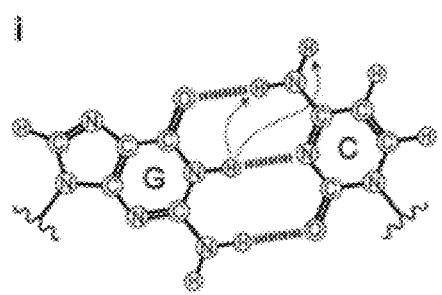
Figure 11:
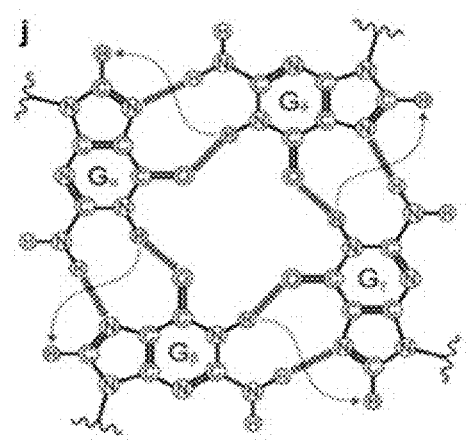
Figure 11:
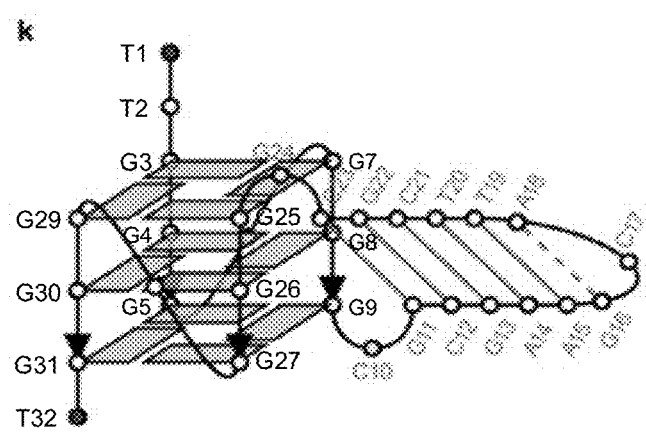
Figure 11:
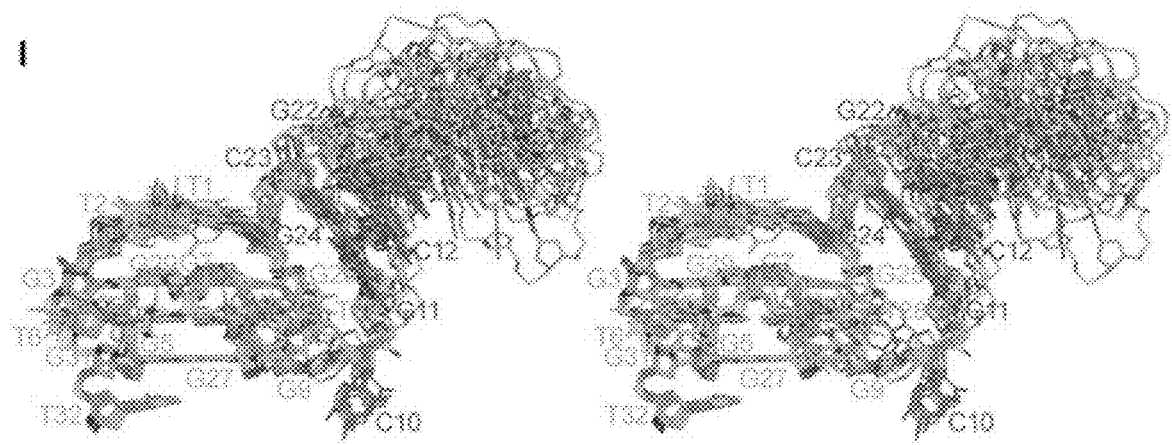
Figure 11:
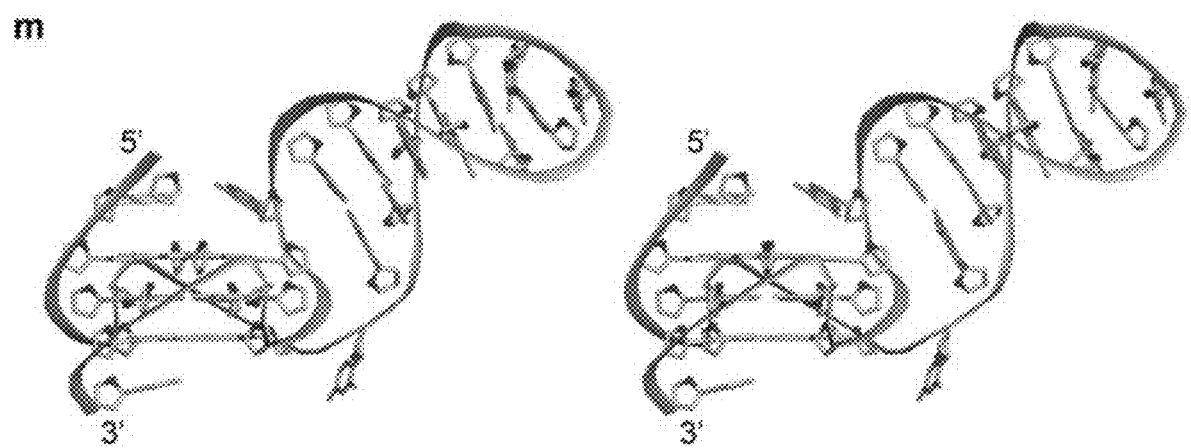

We also investigated the possibility of orthogonal orientation of duplex and quadruplex helices by integrating the hairpin as the middle propeller loop of an all-parallel-stranded G-quadruplex (Construct V, "JMC"—junction across medium groove with two continuous strands; FIG. 4e and FIG. 11). A robust structure is formed with the breaking of a base pair at the duplex-quadruplex junction. The extrusion of the two bases is somewhat akin to the B-Z junction, reflecting perhaps a general mechanism to mediate helical components having different handedness/axial orientation. In the B-Z junction, this permits the continual stacking of bases between two segments with different handedness (right-handed B-DNA onto left-handed Z-DNA). Here, local geometry at the junction necessitates the disruption of the base pair in order to achieve maximal base stacking separately at the duplex and quadruplex ends.

Note that even though the sequences were arbitrarily conceived, the five quadruplex-duplex constructs (FIG. 4) were designed to cover the fundamental aspects of the connectivity between a duplex and a quadruplex (or the incorporation of a duplex as a quadruplex loop). Junction variants can be rationalized as an adaptation or composite of the junctions presented. However, we should not discard the possibility that more exotic junction types may yet exist. Additionally, these "continuous" quadruplex-duplex junctions (in which there are no strand breaks at the points of connection between the duplex and the quadruplex) should be distinguished from "discontinuous" duplex-quadruplex junctions/interfaces (in which there is at least one strand break where the duplex and quadruplex abut), which could arise for instance at the beginning of the single-stranded overhang of telomeric DNA. Nevertheless, the junction types presented could still provide valuable structural insights for the latter cases.

Figure 12:
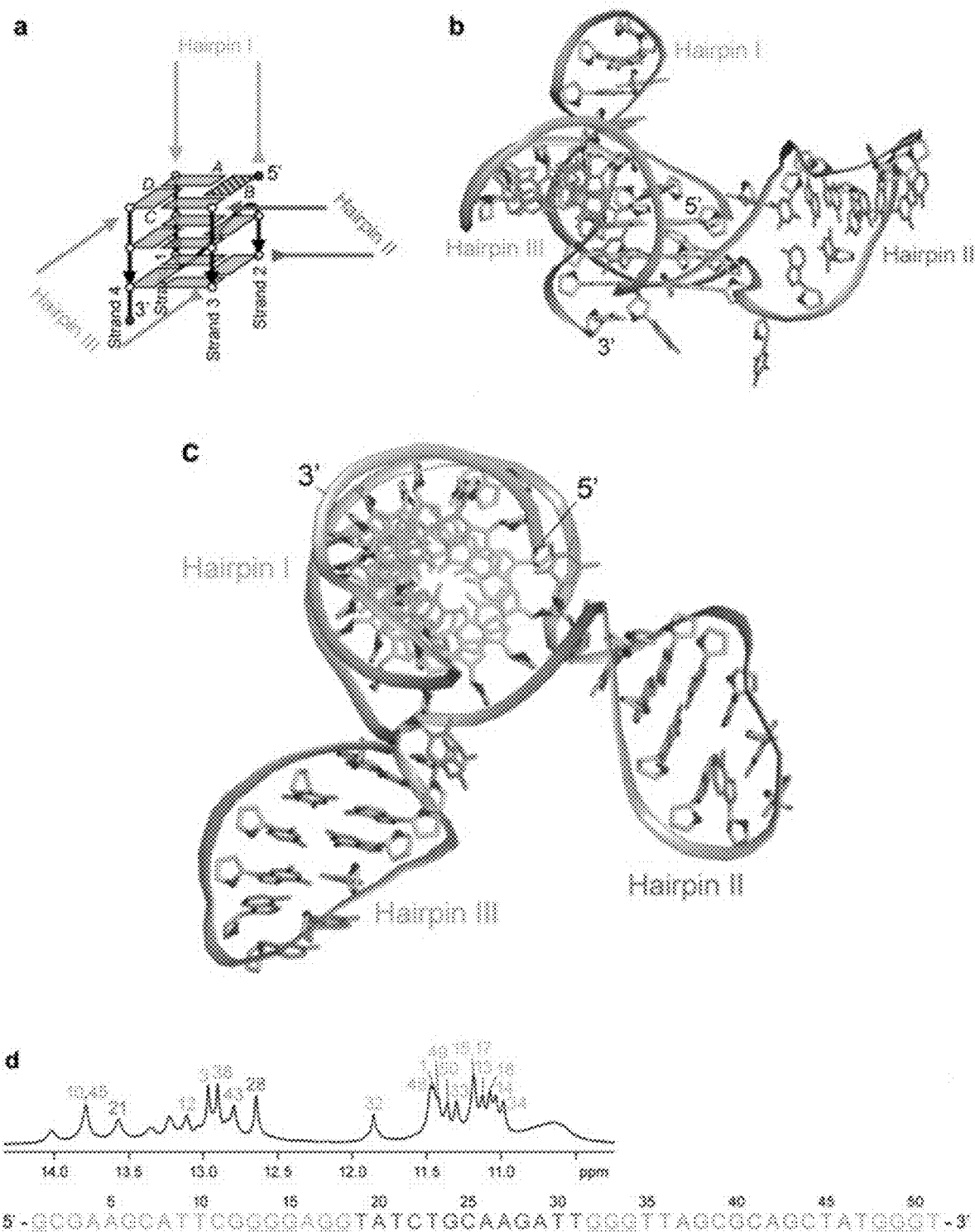
FIG. 12: Rational design of a G-junction bridging three duplex stems. Starting from a G-tetrad core, duplex stems can be incrementally incorporated across its various edges by utilizing attachment strategies that are applicable at each of the resultant quadruplex-duplex junctions. a, Illustration of the duplex attachment strategies that led to the generation of the G-junction construct. Introduction of a nick on Strand 2 allows the coaxial attachment of Hairpin I (green) onto the all-parallel-stranded G-tetrad core (cyan) through the "WMD" junction. Hairpin II (magenta) and Hairpin III (orange) are connected across medium grooves (Edge B and Edge C, respectively) and project laterally from the core. The 5'- and 3'-termini are shown as red circles. b,c, Side (b) and top-down (c) views of the G-junction model in ribbon representation. d, Sequence and 1D imino proton NMR spectrum (assignments listed over the peaks) of the G-junction construct.

We further contemplated the conglomeration of multiple duplexes via a single G-quadruplex hub. This would involve the grafting of each individual duplex stem onto the quadruplex core utilizing a complementary set of attachment strategies appropriate at each of these junctions. We demonstrated this with the successful attachment of three hairpin stems onto a G-quadruplex scaffold, generating a G-junction (FIG. 12; basis of design detailed in figure captions). Overall, the structure comprises three orthogonally-oriented duplex arms, brought together by the complement of twelve guanine residues constituting the tetrad-core. Owing to the diverse G-quadruplex folding topologies available, a multitude of G-junction motifs could be conceived in principle.

The facile yet stable incorporation of duplex hairpin elements within the loops of G-quadruplexes calls for a consideration of G-quadruplexes with longer loop lengths in the evaluation of potential G-quadruplex-forming sequences in the human genome. On the other hand, an understanding on the compatibility between duplex and quadruplex DNA should help with the design of quadruplex-binding ligands with improved specificity, instead of focusing on the discrimination between G-tetrads and canonical Watson-Crick base pairs. In addition, alternative targeting strategies can be apprehended in light of this understanding, ranging from antigene/antisense targeting as described herein to quadruplex-duplex junction binder.

This study presents a paradigm to exact control over the folding topology of a G-quadruplex by the strategic placement of duplex components and auxiliary structural elements. Whereas short G-rich sequences generally lack specificity, judicious introduction of duplex segments drives the core topology towards the desired fold, while eventual formation of the G-quadruplex dictates the orientation of the duplex arm. Such cooperativity between duplex and quadruplex components could be exploited in the makeup of dynamic DNA assembly. Previously, DNA aptamers and DNA enzymes containing G-rich elements were isolated from combinatorial pools of random-sequence DNAs, (R. R. Breaker, Curr. Opin. Chem. Biol. 1997, 1, 26-31.) suggesting an organizational role of G-tetrad motifs in these oligonucleotides. A thorough reconciliation of duplex and quadruplex DNA could pave the way towards the rational design of such complexes based on G-junction motifs.

With a stable core that can potentially serve as an immobile junction, the G-junction is well-poised for integration in DNA nanotechnology. The orthogonal orientation of the three duplex arms in the G-junction motif presented (FIG. 12) suggests an immediate route towards the assembly of three-dimensional DNA nanoarchitectures. Furthermore, G-rich functional elements (e.g. DNA aptamers, enzymes, sensors and nanowires) should now be adaptable with an unprecedented level of control. The dependence of G-quadruplex formation on the presence of cations could also grant an additional layer of control over the assembly of DNA nanomaterials.

Illustration of Targeting Approach: Sequence Design for Target Nucleic Acid and Isolated Oligonucleotide Molecules Arbitrary template sequences 4R and 3R were conceived, comprising four and three G-rich segments, respectively, with about 15-20 nucleotides to the 5'-end (Table 1). 4R and 3R represent the target nucleic acid molecule. In actual cases, the target sequence can be identified from the genomic databases (e.g. Genbank). The isolated oligonucleotide targeting 3R comprises the first nucleotide sequence (TACTTTCGATTAGAGCGA) (SEQ ID NO: 17) complementary to the first 18 nucleotides on 3R and the second nucleotide sequence(TGGG) comprising the G-rich segment GGG.

DNA Polymerase Stop Assays

To demonstrate the feasibility of this approach, we began with DNA polymerase stop assays. Briefly, the targeting oligonucleotide containing one G-tract (designated AGO-3R, Table 1) was allowed to bind to the template strand comprising three G-tracts (designated 3R, Table 1) for the induction of G-quadruplex structure (FIG. 3a, center), and this was compared against quadruplex formation from a complete quadruplex-forming sequence (designated 4R, Table 1; FIG. 3a, left) in terms of their ability to disrupt the progression of DNA polymerase during the extension of a primer. A pause site was observed at the same position in both cases (FIG. 3b, Lane 3 and 6-8), indicating a blockage at the same locus. Furthermore, the extent of this blockage was $K^+$-dependent (FIG. 3b, Lane 2-3 and 5-8), in accordance with quadruplex formation. As a control, neither 3R alone nor binding of a complementary oligonucleotide without G-tract insert (designated AGO-0R, Table 1) onto 3R (FIG. 3a, right) exhibited a comparable blockage (FIG. 3b, Lane 4 and 9, respectively).

TABLE 1

Representative Oligonucleotides Used in This Study

| Name | Sequence[a,b] |
|---|---|
| P | 5'-(6-FAM)TCTCGTGACAGCGTCATTGTACGTC-3' (SEQ ID NO: 11) |
| 4R | 5'-CTCTAATCGAAAGTAGGGTGGGTGGGTGGGTAGTA AGACGTACAATGATGCTGTCACGAGA-3' (SEQ ID NO: 12) |
| 3R | 5'-TCGCTCTAATCGAAAGTAGGGTGGGTGGGTAGTAA GACGTACAATGATGCTGTCACGAGA-3' (SEQ ID NO: 13) |

TABLE 1-continued

Representative Oligonucleotides
Used in This Study

| Name | Sequence[a,b] |
|---|---|
| AGO-3R | 5'-TGGGTACTTTCGATTAGAGCGA-3' (SEQ ID NO: 14) |
| AGO-0R | 5'-CCCTACTTTCGATTAGAGCGA-3' (SEQ ID NO: 15) |

[a]G-quadruplex-forming sequences are underlined.
[b]Primer binding sites are in boldface.

By "comprising" it is meant including, but not limited to, whatever follows the word "comprising". Thus, use of the term "comprising" indicates that the listed elements are required or mandatory, but that other elements are optional and may or may not be present.

By "consisting of" it is meant including, and limited to, whatever follows the phrase "consisting of". Thus, the phrase "consisting of" indicates that the listed elements are required or mandatory, and that no other elements may be present.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

By "about" in relation to a given numerical value, such as for temperature and period of time, it is meant to include numerical values within 10% of the specified value.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

The invention claimed is:

1. A synthetic oligonucleotide molecule comprising or consisting of:
   (i) a first nucleotide sequence substantially complementary to a segment of a target nucleic acid to allow hybridization of the oligonucleotide molecule to said target; and
   (ii) a second nucleotide sequence comprising 1, 2, 3 or 4 G-rich segment/s or partial G-rich segment/s; wherein the second nucleotide sequence comprises or consists of one or more sequences $GxN_yG_x$ (SEQ ID NO:2); $GxN_yGxN_yGx$ (SEQ ID NO:3); or $GxN_yGxN_yGxN_yGx$ (SEQ ID NO:4), $N_yGxN_y$ (SEQ ID NO:5); $N_yGxN_yGxN_y$ (SEQ ID NO:6); $N_yGxN_yGxN_yGxN_y$ (SEQ ID NO:7); or $N_yGxN_yGxN_yGxN_yGxN_y$ (SEQ ID NO:8), the sequence GGGTGGGTGGG (SEQ ID NO:16), and the sequence GGTTGG; wherein each x independently is an integer from 1 to 6 and each y is independently 0 or an integer from 1 to 50, wherein in one or more of the $N_y$ sequence segment/s in any one of SEQ ID NOS: 2-8, y is 5 to 50, and at least one of said one or more $N_y$ sequence segments is at least partially self-complementary and capable of forming a duplex stem-loop structure;
   wherein the synthetic oligonucleotide is configured to form a G-tetrad-duplex hybrid in the presence of a target strand comprising a DNA strand or a target RNA strand and not able to form a stable G-tetrad-duplex hybrid on its own; wherein the synthetic oligonucleotide exhibits a stronger affinity for the target strand as compared to a naturally occurring version of the synthetic oligonucleotide.

2. The synthetic oligonucleotide molecule according to claim 1, wherein the G-rich segment/s that are capable of forming the G-tetrad-duplex hybrid with the target nucleic acid molecule are guanine or tandem guanine sequence/s.

3. The synthetic oligonucleotide molecule according to claim 1, wherein the second nucleotide sequence comprises or consists of the sequence $GxN_yGx$ (SEQ ID NO:2); $GxN_yGxN_yGx$ (SEQ ID NO:3); or $GxN_yGxN_yGxN_yGx$ (SEQ ID NO:4).

4. The synthetic oligonucleotide molecule according to claim 1, wherein said second nucleotide sequence comprises or consists of the nucleic acid sequence $N_yGxN_y$ (SEQ ID NO:5); $N_yGxN_yGxN_y$ (SEQ ID NO:6); $N_yGxN_yGxN_yGxN_y$ (SEQ ID NO:7); or $N_yGxN_yGxN_yGxN_yGxN_y$ (SEQ ID NO:8).

5. The synthetic oligonucleotide molecule according to claim 1, wherein the second nucleotide sequence further comprises the sequence $GxT_yGx$ (SEQ ID NO:9) or $GxTyGxTyGx$ (SEQ ID NO:10), wherein x is an integer of 2 to 6 and y is 1, 2 or 3.

6. The synthetic oligonucleotide according to claim 1, wherein said second nucleotide sequence comprises the sequence GGG, GGGTGGG, GGGTGGGTGGG (SEQ ID NO:16), or GGTTGG.

7. A method of controlling the topography of a target nucleic acid molecule comprising;
(a) contacting the target nucleotide sequence with a synthetic oligonucleotide molecule according to claim 1, wherein the synthetic oligonucleotide molecule and the target nucleic acid molecule each comprises 1, 2, 3 or 4 G-rich segment/s or partial G-rich segment/s that can take part in the formation of a G-tetrad core and wherein the synthetic oligonucleotide molecule and the target nucleic acid molecule combined comprise four segments with a total of 8, 12, 16, 20 or 24 guanine bases that are capable of forming a G-tetrad core between the synthetic oligonucleotide molecule and the target nucleic acid molecule.

8. The method according to claim 7, wherein the target nucleic acid is DNA.

9. The method according to claim 8, wherein the synthetic oligonucleotide molecule is targeted to form a G-quadruplex on the template strand of a functional gene coding for a protein of interest thereby inhibiting transcription of the target nucleic acid molecule.

10. The method according to claim 7, wherein the target nucleic acid is RNA.

11. The method according to claim 10, wherein the target nucleic acid is mRNA, and wherein the synthetic oligonucleotide molecule is targeted to form a G-quadruplex on the mRNA coding for a protein of interest thereby inhibiting translation of the target nucleic acid molecule.

12. A method of identifying a target nucleic acid molecule capable of forming a G-quadruplex with a synthetic oligonucleotide molecule according to claim 1, comprising the steps of:
(a) searching for a nucleic acid sequence in a sequence database, wherein said sequence comprises 1, 2, 3 or 4 G-rich segment/s or partial G-rich segment/s that are capable of forming a G-tetrad core in conjunction with the synthetic oligonucleotide molecule;
(b) contacting the synthetic oligonucleotide molecule with the nucleic acid identified in (a); and
(c) observing whether the nucleic acid sequence identified in (a) is able to form a G-tetrad core in conjunction with the synthetic oligonucleotide of (b).

13. The method according to claim 12, wherein the target nucleic acid comprises a deoxyribonucleic acid or a ribonucleic acid.

14. The method according to claim 12, wherein the G-rich segment/s capable of forming the G-tetrad core in conjunction with the synthetic oligonucleotide are guanine or tandem guanine sequence/s.

15. The method according to claim 12, wherein the G-rich segment/s of the target nucleic acid comprise or consist of the sequence Gx (SEQ ID NO:1), $GxN_yGx$ (SEQ ID NO:2); $GxN_yGxN_yGx$ (SEQ ID NO:3); or $GxN_yGxN_yGxN_yGx$ (SEQ ID NO:4), wherein each x independently is an integer from 1-6 and each y independently is an integer from 0-50.

16. The method according to claim 15, wherein the G-rich segment/s comprise or consist of the nucleic acid sequence $N_yGxN_y$ (SEQ ID NO:5);
$N_yGxN_yGxN_y$ (SEQ ID NO:6); $N_yGxN_yGxN_yGxN_y$ (SEQ ID NO:7); or $N_yGxN_yGxN_yGxN_yGxN_y$ (SEQ ID NO:8).

17. The method according to claim 15, wherein in one or more of the $N_y$ sequence segments in any one of SEQ ID NOS:1-8, y is 5 to 50 and said one or more $N_y$ sequence segments are self-complementary and capable of forming a duplex stem-loop structure.

18. The method according to claim 12, wherein the G-rich segment/s of the target nucleic acid comprise or consist of the sequence $GxT_yGx$ (SEQ ID NO:9) or $GxT_yGxT_yGx$ (SEQ ID NO:10), wherein x is an integer of 2-6 and y is 1, 2 or 3.

19. The method according to claim 12, wherein the G-rich segment/s of the target nucleic acid comprise the sequence GGG, GGGTGGG, GGGTGGGTGGG (SEQ ID NO:16), or GGTTGG.

20. The synthetic oligonucleotide molecule according to claim 1, wherein the synthetic oligonucleotide constitutes 1, 2 or 3 column(s) of the G-tetrad core and the target molecule constitutes the remaining column(s), or the synthetic oligonucleotide constitutes 3 complete columns and 1 incomplete column and the target molecule constitutes the remaining part of the incomplete column, or the target molecule constitutes 3 complete columns and 1 incomplete column and the synthetic oligonucleotide constitutes the remaining part of the incomplete column.

* * * * *